US012690595B2

(12) United States Patent
Breakfield et al.

(10) Patent No.: US 12,690,595 B2
(45) Date of Patent: Jul. 28, 2026

(54) METHYLOBACTERIUM STRAINS FOR MITIGATING METHANE AND METHODS RELATED THERETO

(71) Applicant: NewLeaf Symbiotics, Inc., St. Louis, MO (US)

(72) Inventors: Natalie Breakfield, St. Louis, MO (US); Desmond R. Jimenez, St. Louis, MO (US); David Flack, St. Louis, MO (US)

(73) Assignee: NewLeaf Symbiotecs, Inc., St. Louis, MO (US)

( * ) Notice: Subject to any disclaimer, the term of this patent is extended or adjusted under 35 U.S.C. 154(b) by 307 days.

(21) Appl. No.: 18/689,160

(22) PCT Filed: Sep. 8, 2022

(86) PCT No.: PCT/US2022/076129

§ 371 (c)(1),
(2) Date: Mar. 5, 2024

(87) PCT Pub. No.: WO2023/039481

PCT Pub. Date: Mar. 16, 2023

(65) Prior Publication Data

US 2025/0113827 A1 Apr. 10, 2025

Related U.S. Application Data

(60) Provisional application No. 63/388,461, filed on Jul. 12, 2022, provisional application No. 63/289,475, filed on Dec. 14, 2021, provisional application No. 63/241,818, filed on Sep. 8, 2021.

(51) Int. Cl.
| | |
|---|---|
| *A01N 63/20* | (2020.01) |
| *A01C 1/06* | (2006.01) |
| *A01P 21/00* | (2006.01) |
| *C12N 1/20* | (2026.01) |
| *C12R 1/20* | (2006.01) |
| *C12R 1/01* | (2006.01) |

(52) U.S. Cl.
CPC .............. *A01N 63/20* (2020.01); *A01C 1/06* (2013.01); *A01P 21/00* (2021.08); *C12N 1/20* (2013.01); *C12Y 114/13025* (2013.01); *C12R 2001/01* (2021.05)

(58) Field of Classification Search
CPC ........... A01N 63/20; A01C 1/06; A01P 21/00; C12N 1/20; C12Y 114/13025; C12R 2001/01
See application file for complete search history.

(56) References Cited

U.S. PATENT DOCUMENTS

| | | |
|---|---|---|
| 2002/0067953 A1 | 6/2002 | Ankeny et al. |
| 2015/0104854 A1 | 4/2015 | Singh et al. |
| 2016/0369311 A1 | 12/2016 | Singh et al. |
| 2019/0116803 A1 | 4/2019 | DiDonato et al. |
| 2019/0364905 A1 * | 12/2019 | Rioux .................... A01N 63/20 |
| 2020/0095611 A1 | 3/2020 | Galazka et al. |
| 2020/0102457 A1 | 4/2020 | Goldstein et al. |
| 2020/0190544 A1 | 6/2020 | Herrema et al. |
| 2020/0263212 A1 | 8/2020 | Herrema |

FOREIGN PATENT DOCUMENTS

| | | |
|---|---|---|
| WO | 2013181610 A1 | 12/2013 |
| WO | 2014194189 A1 | 12/2014 |
| WO | 2015085063 A1 | 6/2015 |
| WO | 2015085115 A1 | 6/2015 |
| WO | 2015085116 A1 | 6/2015 |
| WO | 2015085117 A1 | 6/2015 |
| WO | 2015142393 A1 | 9/2015 |
| WO | 2016069564 A1 | 5/2016 |
| WO | 2016201284 A1 | 12/2016 |
| WO | 2018106899 A1 | 6/2018 |
| WO | 2019232049 A1 | 12/2019 |
| WO | 2020117689 A1 | 6/2020 |
| WO | 2020117690 A1 | 6/2020 |
| WO | 2020163027 A1 | 8/2020 |
| WO | 2021007516 A1 | 1/2021 |
| WO | 2021025751 A1 | 2/2021 |
| WO | 2021163148 A1 | 8/2021 |

OTHER PUBLICATIONS

Hara, Shintaro et al., In Vivo Evidence of Single 13C and 15N Isotope-Labeled Methanotrophic Nitrogen-Fixing Bacterial Cells in Rice Roots, American Society for Microbiology, (May/Jun. 2022) vol. 13, Issue 3, pp. 1-6.
Malyan, Sandeep K. et al., Mitigation of yield-scaled greenhouse gas emissions from irrigated rice through Azolla, Blue-green algae, and plant growth-promoting bacteria, Environmental Science and Pollution Research 28, 51425-51439 (2021).
Rani, Vijaya et al., Inoculation of plant growth promoting-methane utilizing bacteria in different N-fertilizer regime influences methane emission and crop growth of flooded paddy, Science of the Total Environment 775 (2021) 145826, pp. 1-12.
Strobel, Scott et al., Industrially-Scalable Microencapsulation of Plant Beneficial Bacteria in Dry Cross-Linked Alginate Matrix, Industrial Biotechnology, vol. 14, No. 3 (Jun. 2018) pp. 138-147.
International Search Report and Written Opinion dated Feb. 1, 2023 relating to PCT/US2022/076129, 25 pages.
International Search Report and Written Opinion dated Feb. 16, 2024, issued in PCT Patent Application No. PCT/US2023/070041. 21 pages.

* cited by examiner

*Primary Examiner* — Trevor Love
(74) *Attorney, Agent, or Firm* — Stinson LLP

(57) ABSTRACT

*Methylobacterium* strains that enhance early growth of plants, improve propagation/transplant vigor, increase nutrient uptake, improve stand establishment, improve stress tolerance and/or increase a plant's ability to utilize nutrients are provided herein. Also provided are methods to reduce green-house gas emission and convert methane to methanole with *Methylobacterium* strains.

18 Claims, No Drawings

Specification includes a Sequence Listing.

1

METHYLOBACTERIUM STRAINS FOR MITIGATING METHANE AND METHODS RELATED THERETO

CROSS-REFERENCE TO RELATED APPLICATIONS

This patent application claims the benefit of PCT Application No. PCT/US2022/076129, filed Sep. 8, 2022, which claims benefit of U.S. Provisional Patent Application No. 63/241,818, filed Sep. 8, 2021, U.S. Provisional Patent Application No. 63/289,475, filed Dec. 14, 2021, and U.S. Provisional Patent Application No. 63/388,461, filed Jul. 12, 2022, the entire disclosures of which are incorporated herein by reference.

SEQUENCE LISTING STATEMENT

A Sequence Listing XML containing the file named "NLSYM7003.WO Sequence Listing.xml" which is 268,780 bytes (measured in MS-Windows®) and created on Sep. 13, 2022, contains 53 nucleic acid sequences and 22 amino acid sequences is provided herewith, and is incorporated herein by reference in its entirety.

BACKGROUND

Plants require certain macronutrients and micronutrients for growth and metabolism. These elements are generally found in the soil as salts and can be consumed by plants as ions. In agriculture, soil can become depleted of one or more of these nutrients requiring the addition of fertilizers to provide sufficient quantities of the nutrients for crop growth. In hydroponic systems, all nutrients must be supplied to the growing plants and are often the greatest cost for a hydroponic plant production system. Methods of enhancing plant production by improving growth and/or increasing nutrient utilization are desired.

One-carbon organic compounds such as methane and methanol are found extensively in nature, and may be utilized as carbon sources by bacteria. Methanotrophic bacteria include species in the genera *Methylobacter, Methylorubrum, Methylomonas, Methylomicrobium, Methylococcus, Methylosinus, Methylocystis, Methylosphaera, Methylocaldum,* and *Methylocella* (Lidstrom, 2006). Methanotrophs possess the enzyme methane monooxygenase which incorporates an atom of oxygen from 02 into methane, forming methanol. All methanotrophs are obligate one-carbon utilizers that are unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium, Hyphomicrobium, Methylophilus, Methylobacillus, Methylophaga, Aminobacter, Methylorhabdus, Methylopila, Methylosulfonomonas, Marinosulfonomonas, Paracoccus, Xanthobacter, Ancylobacter* (also known as *Microcyclus*), *Thiobacillus, Rhodopseudomonas, Rhodobacter, Acetobacter, Bacillus, Mycobacterium, Arthobacter,* and *Nocardia* (Lidstrom, 2006).

Some methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium,* specifically *M. aminovorans, M. chloromethanicum, M. dichloromethani-*

2

*cum, M. extorquens, M. fujisawaense, M. mesophilicum, M. organophilum, M. radiotolerans, M. rhodesianum, M. rhodinum, M. thiocyanatum,* and *M. zatmanii.* However, *M. nodulans* is a nitrogen-fixing *Methylobacterium* that is not a PPFM (Sy et al., 2001). Some publications have reported that other *Methylobacterium* species are capable of fixing nitrogen (Madhaiyan et al. (2015) Biotechnol. Biofuels: 8:222; WO2020245675) although nitrogen fixation pathway genes have not been reported to be present in those species.

All nations have tried to frame a global regime to control green-house gas emissions and to assist with adaptation and yet emissions have continued to increase. Methane is a critical component of Earth's carbon cycle and contributes global warming. Agriculture (e.g., enteric fermentation in livestock, manure management, and rice cultivation) is a contributor to global $CH_4$ emission. Implementation of a biological methane oxidizing technology has the potential for mitigation of atmospheric methane levels and reduction of green-house gas emissions.

SUMMARY

Provided herein are *Methylobacterium* strains and compositions comprising one or more *Methylobacterium* strains, wherein the strains mitigate methane gas, enhance early growth of plants, improve yield of a crop and/or crop product, improve propagation/transplant vigor, increase nutrient uptake, improve stand establishment, improve stress tolerance, and/or increase a plant's ability to utilize nutrients, such as nitrogen, potassium, sulfur, cobalt, copper, zinc, phosphorus, boron, iron, and manganese, and/or that have ability fixate nitrogen. In certain embodiments, the *Methylobacterium* mitigates methane by oxidation by a soluble methane monooxygenase (sMMO) encoded by genetic elements in the genome of the *Methylobacterium* strain. In some embodiments, sMMO encoding genetic elements are present on a plasmid in a methane mitigating *Methylobacterium* strain. In some embodiments, a *Methylobacterium* strain capable of mitigating methane comprises genetic elements encoding SEQ ID NOS: 1-4. In some embodiments, a *Methylobacterium* strain capable of mitigating methane comprises genetic elements encoding SEQ ID NOS: 5-8. In some embodiments, a *Methylobacterium* strain capable of mitigating methane comprises genetic elements encoding sMMO components having at least 65% identity to SEQ ID NOS: 1-4 or 5-8. In some embodiments, the genetic elements comprise SEQ ID NOS: 9-12. In some embodiments, the genetic elements comprise SEQ ID NOS: 13-16. In some embodiments, the genetic elements have at least 65% identity to SEQ ID NOS: 9-12 or 13-16. In some embodiments, a *Methylobacterium* strain capable of mitigating methane is selected from the group consisting of NLS0770 (NRRL B-68075), NLS0737 (NRRL B-68074), NLS5278 (NRRL-B-68186), NLS5334 (NRRL-B-68187), NLS5480 (NRRL-B-68188), NLS5549 (NRRL-B-68189) and variants thereof. In certain embodiments, a *Methylobacterium* capable of mitigating methane also provides for at least one plant benefit selected from the group consisting of enhanced early growth of plants, improved yield, improved propagation/transplant vigor, increased nutrient uptake, improved stand establishment, improved stress tolerance, and/or increased ability of the plant to utilize nutrients, such as nitrogen, potassium, sulfur, cobalt, copper, zinc, phosphorus, boron, iron, and manganese. In some embodiments, a *Methylobacterium* capable of mitigating methane fixates nitrogen.

In some embodiments, compositions comprising a *Methylobacterium* capable of mitigating methane further comprise one or more *Methylobacterium* strains that provide for at least one plant benefit selected from the group consisting of enhanced early growth of plants, improved yield of a crop and/or crop product, improved propagation/transplant vigor, increased nutrient uptake, improved stand establishment, improved stress tolerance, improved pest resistance, improved pathogen resistance, fruit ripening and/or increased ability of the plant to utilize nutrients, such as nitrogen, potassium, sulfur, cobalt, copper, zinc, phosphorus, boron, iron, and manganese. In some embodiments, such compositions comprise a *Methylobacterium* that fixates nitrogen. In some embodiments, an additional *Methylobacterium* strain in a composition is selected from the group consisting of LGP2000 (NRRL B-50929), LGP2001 (NRRL B-50930), LGP2002 (NRRL B-50931), LGP2003 (NRRL B-50932), LGP2004 (NRRL B-50933), LGP2005 (NRRL B-50934), LGP2006 (NRRL B-50935), LGP2007 (NRRL B-50936), LGP2008 (NRRL B-50937), LGP2009 (NRRL B-50938), LGP2010 (NRRL B-50939), LGP2011 (NRRL B-50940), LGP2012 (NRRL B-50941), LGP2013 (NRRL B-50942), LGP2014 (NRRL B-67339), LGP2015 (NRRL B-67340), LGP2016 (NRRL B-67341), LGP2017 (NRRL B-67741), LGP2018 (NRRL B-67742), LGP2019 (NRRL B-67743), NLS0497 (NRRL B-67925), NLS0693 (NRRL B-67926), NLS1179 (NRRL B-67929), LGP2167 (NRRL B-67927), LGP2020 (NRRL-B-67892), LGP2021 (NRRL-B-68032), LGP2022 (NRRL-B-68033), LGP2023 (NRRL-B-68034), LGP2029 (NRRL B-68065), LGP2030 (NRRL B-68066), LGP2031 (NRRL B-68067), LGP2033 (NRRL B-68068), LGP2034 (NRRL B-68069), and variants thereof. In certain embodiments, a variant of an additional *Methylobacterium* or variant thereof is identified by the presence of one or more of SEQ ID NOs: 33-75. In certain embodiments, the compositions provided herein enhance uptake and/or utilization of one or more nutrients and/or enhances nitrogen use efficiency of a treated plant or a plant grown in treated soil, and a *Methylobacterium* in the composition is selected from the group consisting of LGP2001 (NRRL B-50930), LGP2002 (NRRL B-50931), LGP2009 (NRRL B-50938), LGP2015 (NRRL B-67340), LGP2016 (NRRL B-67341), LGP2017 (NRRL B-67741), LGP2018 (NRRL B-67742), LGP2019 (NRRL B-67743), NLS0693 (NRRL B-67926), LGP2167 (NRRL B-67927), LGP2020 (NRRL-B-67892), LGP2021 (NRRL-B-68032), LGP2022 (NRRL-B-68033), LGP2023 (NRRL-B-68034), LGP2029 (NRRL B-68065), LGP2030 (NRRL B-68066), LGP2031 (NRRL B-68067), LGP2033 (NRRL B-68068), LGP2034 (NRRL B-68069), and variants thereof. In certain embodiments, a *Methylobacterium* or variant thereof that increases uptake and/or utilization of one or more nutrients and/or enhances nitrogen use efficiency is identified by the presence of one or more of SEQ ID NOs: 33-39, 46-60, 64-66, or 70-75. In certain embodiments, the *Methylobacterium* in the compositions provided herein comprise one or more genetic elements associated with the ability to enhance early plant growth, wherein the one or more genetic elements (i) is recD2_2 or pinR; or (ii) the one or more genetic elements encode a protein having a consensus amino acid sequence of SEQ ID NO: 17 to SEQ ID NO: 23. In some embodiments, *Methylobacterium* in the compositions provided herein that improve early plant growth also impart one or more additional beneficial traits to treated plants or plants grown from treated plant parts or seeds, wherein the trait is enhanced uptake of nutrients, enhanced assimilation of nutrients, and/or enhanced nutrient use efficiency. In some embodiments, plants treated with *Methylobacterium* isolates provided herein demonstrate enhanced nitrogen use efficiency. In certain embodiments, the compositions provided herein enhance yield of a treated crop or crop product of a treated crop plant or a crop plant grown in treated soil. In certain embodiments, the crop is rice, and the compositions comprise a *Methylobacterium* capable of mitigating methane selected from the group consisting of NLS0770 (NRRL-B-68075), NLS5278 (NRRL-B-68186), NLS5334 (NRRL-B-68187), NLS5480 (NRRL-B-68188), NLS5549 (NRRL-B-68189), and variants thereof, and an additional *Methylobacterium* providing for enhanced yield of rice. In some embodiments, the additional *Methylobacterium* is selected from the group consisting of LGP2016 (NRRL B-67341), LGP2017 (NRRL B-67741), LGP2019 (NRRL B-67743), and variants thereof. Also provided are isolated *Methylobacterium* selected from NLS0770 (NRRL-B-68075), NLS5278 (NRRL-B-68186), NLS5334 (NRRL-B-68187), NLS5480 (NRRL-B-68188), NLS5549 (NRRL-B-68189), and variants thereof, compositions comprising such *Methylobacterium* isolates or variants thereof, and plants, plant parts, or seeds that are at least partially coated with compositions comprising NLS0770 (NRRL-B-68075), NLS5278 (NRRL-B-68186), NLS5334 (NRRL-B-68187), NLS5480 (NRRL-B-68188), NLS5549 (NRRL-B-68189), and variants thereof. Variants of NLS0737 or NLS0770 can be identified, for example, by the presence of SEQ ID NO:31 in the genome of a methane mitigating *Methylobacterium*. Variants of NLS5278, NLS5334, NLS5480, or NLS5549 can be identified, for example, by the presence of SEQ ID NO:32 in the genome of a methane mitigating *Methylobacterium*. In some embodiments, the plant is rice. In some embodiments, the plant is a crop grown for feeding livestock, for example grasses in a pasture where livestock feed. In some embodiments, the coated plant or plant part comprises plant material harvested for livestock feed, wherein the *Methylobacterium* is applied to a seed or to a growing a plant, and wherein harvested plant material comprises methane mitigating *Methylobacterium*. In some embodiments, *Methylobacterium* is added directly to livestock feed.

Also provided are compositions comprising a fermentation product comprising a *Methylobacterium* strain that is essentially free of contaminating microorganisms. In certain embodiments, the *Methylobacterium* strain is selected from the group consisting of NLS0770 (NRRL-B-68075), NLS5278 (NRRL-B-68186), NLS5334 (NRRL-B-68187), NLS5480 (NRRL-B-68188), NLS5549 (NRRL-B-68189), and variants thereof. In certain embodiments, the composition further comprises one or more additional components including one or more agriculturally acceptable adjuvants or excipients, and/or an additional active component, for example a pesticide or a second biological. In certain embodiments, the pesticide can be, for example, an insecticide, a fungicide, an herbicide, or a nematicide. The second biological can be a strain that improves yield or controls an insect, pest, fungi, weed, or nematode. In some embodiments, a second biological is a second *Methylobacterium* strain.

Also provided herein are plants, plant parts or seeds that are treated with *Methylobacterium* strains and compositions provided herein. Such plants can be without limitation, agricultural crop plants, fruits and vegetables, leafy green plants, herbs, ornamentals, turf grasses and trees.

Also provided herein are methods of mitigating methane using *Methylobacterium* strains and compositions provided herein. Methane mitigation methods provided herein include methods to decrease methane levels by reducing methane emissions or by enhancing removal of methane from sources of the gas, such as agricultural soil, wetlands, landfills, waste facilities, animal feed, water or air. In one embodiment, a method for mitigating methane gas in an agricultural field that comprise applying a composition to a field, plant, plant part or seed, wherein the composition comprises at least one *Methylobacterium* selected from the group consisting of NLS0737, NLS0770, NLS5278, NLS5334, NLS5480, NLS5549, and variants thereof, and growing the *Methylobacterium* whereby the *Methylobacterium* uses methane as a carbon source, and said utilization of the methane as the carbon source oxidizes methane and reduces methane emissions in the field. In some embodiments, the *Methylobacterium* composition is applied to an irrigated field, a flooded field, or a field that will be irrigated or will become flooded. In some embodiments, the *Methylobacterium* is applied to a rice plant, plant part or seed. In some embodiments, the *Methylobacterium* is applied to a flooded or irrigated rice field.

In some embodiments, a method for mitigating methane comprises treating a pasture, wasteland, a landfill or waste with a composition comprising at least one *Methylobacterium* isolate; and growing the *Methylobacterium* in the pasture, wasteland, a landfill or waste thereby mitigating methane. In some embodiments, the *Methylobacterium* is selected from the group consisting of NLS0737, NLS0770, NLS5278, NLS5334, NLS5480, NLS5549, and variants thereof.

In some embodiments, a method for mitigating methane comprises mitigation of methane production by livestock, wherein said method comprises treating land where livestock feed or will feed, with at least one *Methylobacterium* thereby reducing methane from livestock feed. In some embodiments, the *Methylobacterium* is selected from the group consisting of NLS0737, NLS0770, NLS5278, NLS5334, NLS5480, NLS5549, and variants thereof.

Also, methods for reducing methane emissions from a methane emitting source are disclosed. These methods comprise applying a composition comprising at least one *Methylobacterium* isolate to the methane emitting source.

In some embodiments, a method for mitigating methane comprises reducing methane concentration in a methane-containing media (e.g., manure or livestock waste) or fluid (e.g., any methane-containing gas or liquid such as methane-contaminated groundwater), the method comprising applying a composition comprising at least one *Methylobacterium* isolate to the media or fluid. In some embodiments, the *Methylobacterium* is selected from the group consisting of NLS0737, NLS0770, NLS5278, NLS5334, NLS5480, NLS5549, and variants thereof.

In some embodiments, a method for mitigating methane comprises reducing methane emissions (e.g., in a landfill), the method comprising applying a first coating of a composition comprising at least one *Methylobacterium* isolate to a first layer of material (e.g., overburden/soil or waste); at least partially covering the first layer and first coating with a second layer of material (e.g., overburden/soil or additional waste); applying a second coating of the composition comprising the at least one *Methylobacterium* isolate to a second layer; and growing the *Methylobacterium*. In some embodiments, the *Methylobacterium* is selected from the group consisting of NLS0737, NLS0770, NLS5278, NLS5334, NLS5480, NLS5549, and variants thereof.

Also disclosed is a method for selecting a *Methylobacterium* isolate capable of utilizing methanol as a food source, wherein the method comprises (a) detecting in the genome of a *Methylobacterium* isolate, a genetic element, wherein the genetic element comprises a component of a soluble methane monooxygenase; and (b) treating a field, water, plant, plant part or seed with the *Methylobacterium* isolate, and measuring green-house gas emissions.

Also provided herein are recombinant constructs for expression of an sMMO component protein, or modification thereof, wherein said construct comprises a genetic element encoding any one or more of SEQ ID NO: 1-8 or a modification thereof.

DETAILED DESCRIPTION

Definitions

The term "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "include," "includes," and "including" are to be construed as at least having the features or encompassing the items to which they refer while not excluding any additional unspecified features or unspecified items.

As used herein, the term "biological" refers to a component of a composition for treatment of plants or plant parts comprised of or derived from a microorganism. Biologicals include biocontrol agents, other beneficial microorganisms, microbial extracts, plant extracts, yeast extracts, vegetal chitosan, natural products, plant growth activators or plant defense agents. Non-limiting examples of biocontrol agents include bacteria, fungi, beneficial nematodes, and viruses. In certain compositions, a biological can comprise a mono-culture or co-culture of *Methylobacterium*, or a combination of *Methylobacterium* strains or isolates that have been separately cultured.

As used herein "mitigate methane" refers to decreasing methane levels by reducing methane emissions or by enhancing removal of methane from sources of the gas, such as agricultural soil, wetlands, landfills, waste facilities, animal feed, water or air. Mitigation of methane may be the result of methane oxidation by the activity of sMMO in the *Methylobacterium* strains provided herein, or may be the result of secondary effects of the provided *Methylobacterium* strains on the microbiome of a treated plant or plant part.

As used herein, the term "*Methylobacterium*" refers to genera and species in the methylobacteriaceae family, including bacterial species in the *Methylobacterium* genus and proposed *Methylorubrum* genus (Green and Ardley (2018)). *Methylobacterium* includes pink-pigmented facultative methylotrophic bacteria (PPFM) and also encompasses the non-pink-pigmented *Methylobacterium nodulans*, as well as colorless mutants of *Methylobacterium* isolates. For example, and not by way of limitation, "*Methylobacterium*" refers to bacteria of the species listed below as well as any new *Methylobacterium* species that have not yet been reported or described that can be characterized as *Methylobacterium* or *Methylorubrum* based on phylogenetic analysis: *Methylobacterium adhaesivum; Methylobacterium oryzae; Methylobacterium aerolatum; Methylobacterium oxalidis; Methylobacterium aquaticum; Methylobacterium*

*persicinum; Methylobacterium brachiatum; Methylobacterium phyllosphaerae; Methylobacterium brachythecii; Methylobacterium phyllostachyos; Methylobacterium bullatum; Methylobacterium platani; Methylobacterium cerastii; Methylobacterium pseudosasicola; Methylobacterium currus; Methylobacterium radiotolerans; Methylobacterium dankookense; Methylobacterium soli; Methylobacterium frigidaeris; Methylobacterium specialis; Methylobacterium fujisawaense; Methylobacterium tardum; Methylobacterium gnaphalii; Methylobacterium tarhaniae; Methylobacterium goesingense; Methylobacterium thuringiense; Methylobacterium gossipiicola; Methylobacterium trifolii; Methylobacterium gregans; Methylobacterium variabile; Methylobacterium haplocladii; Methylobacterium aminovorans (Methylorubrum aminovorans); Methylobacterium hispanicum; Methylobacterium extorquens (Methylorubrum extorquens); Methylobacterium indicum; Methylobacterium podarium (Methylorubrum podarium); Methylobacterium iners; Methylobacterium populi (Methylorubrum populi); Methylobacterium isbiliense; Methylobacterium pseudosasae (Methylorubrum pseudosasae); Methylobacterium jeotgali; Methylobacterium rhodesianum (Methylorubrum rhodesianum); Methylobacterium komagatae; Methylobacterium rhodinum (Methylorubrum rhodinum); Methylobacterium longum; Methylobacterium salsuginis (Methylorubrum salsuginis); Methylobacterium marchantiae; Methylobacterium suomiense (Methylorubrum suomiense; Methylobacterium mesophilicum; Methylobacterium thiocyanatum (Methylorubrum thiocyanatum); Methylobacterium nodulans; Methylobacterium zatmanii (Methylorubrum zatmanii); Methylobacterium symbiota; or Methylobacterium organophilum.*

"Colonization efficiency" as used herein refers to the relative ability of a given microbial strain to colonize a plant host cell or tissue as compared to non-colonizing control samples or other microbial strains. Colonization efficiency can be assessed, for example and without limitation, by determining colonization density, reported for example as colony forming units (CFU) per mg of plant tissue, or by quantification of nucleic acids specific for a strain in a colonization screen, for example using qPCR.

As used herein "mineral nutrients" (also sometime referred to simply as "nutrients") are micronutrients or macronutrients required or useful for plants or plant parts including for example, but not limited to, nitrogen (N), potassium (K), calcium (Ca), magnesium (Mg), phosphorus (P), and sulfur (S), and the micronutrients chlorine (Cl), Iron (Fe), Boron (B), manganese (Mn), zinc (Z), cobalt (Co), copper (Cu), molybdenum (Mo) and nickel (Ni).

As used herein, "vitamins" are organic compounds required in small amounts for normal growth and metabolism. Vitamins are important for human and/or animal growth and some vitamins have been reported to be beneficial to plants. Vitamins include but are not limited to vitamin A (including but not limited to all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones).

As used herein "fertilizer" can be a single nutrient nitrogen fertilizer, such as urea, ammonia or ammonia solutions (including ammonium nitrate, ammonium sulfate, calcium ammonium nitrate, and urea ammonium nitrate). In certain embodiments, the fertilizer can be a single nutrient phosphate fertilizer, such as a superphosphate or triple superphosphate or mixtures thereof, including double superphosphate. In certain embodiments, the fertilizer can be a single nutrient potassium-based fertilizer, such as muriate of potash. In certain embodiments, the compositions comprise multinutrient fertilizers including binary fertilizers (NP, NK, PK), including, for example monoammonium phosphate, diammonium phosphate, potassium nitrate and potassium chloride. In further embodiments, three-component fertilizers (NPK) providing nitrogen, phosphorus, and potassium are present in the aqueous compositions. In still further embodiments, the fertilizer comprises micronutrients, which may be chelated or non-chelated. In some embodiments, combinations of various fertilizers can be present in the aqueous solution, including combinations of nitrogen, phosphorus and/or micronutrient fertilizers. Nutrient solutions provided in hydroponic plant growth systems are also considered "fertilizers" in methods and compositions described herein.

As used herein, the term "strain" shall include all isolates of such strain.

As used herein, "variant" when used in the context of a *Methylobacterium* isolate, refers to any isolate that has chromosomal genomic DNA with at least 99%, 99.9, 99.8, 99.7, 99.6%, or 99.5% sequence identity to chromosomal genomic DNA of a reference *Methylobacterium* isolate, such as, for example, a deposited *Methylobacterium* isolate provided herein. A variant of an isolate can be obtained from various sources including soil, plants or plant material, and water, particularly water associated with plants and/or agriculture. Variants include derivatives obtained from deposited isolates. *Methylobacterium* isolates or strains can be sequenced (for example as taught by Sanger et al. (1977), Bentley et al. (2008) or Caporaso et al. (2012)) and genome-scale comparison of the sequences conducted (Konstantinidis et al. (2005)) using sequence analysis tools, such as BLAST, as taught by Altschul et al. (1990) or clustalw (www.ebi.ac.uk/Tools/msa/clustalw2/).

As used herein, "derivative" when used in the context of a *Methylobacterium* isolate, refers to any *Methylobacterium* that is obtained from a deposited *Methylobacterium* isolate provided herein. Derivatives of a *Methylobacterium* isolate include, but are not limited to, derivatives obtained by selection, derivatives selected by mutagenesis and selection, and genetically transformed *Methylobacterium* obtained from a *Methylobacterium* isolate. A "derivative" can be identified, for example based on genetic identity to the strain or isolate from which it was obtained and will generally exhibit chromosomal genomic DNA with at least 99%, 99.9, 99.8, 99.7, 99.6%, or 99.5% sequence identity to chromosomal genomic DNA of the strain or isolate from which it was derived.

As used herein, "sequence identity" when used to evaluate whether a particular *Methylobacterium* strain is a variant or derivative of a *Methylobacterium* strain provided herein refers to a measure of nucleotide-level genomic similarity between the coding regions of two genomes. Sequence identity between the coding regions of bacterial genomes can be calculated, for example, by determining the Average Nucleotide Identity (ANI) score using FastANI (Jain et al. "High throughput ANI analysis of 90K prokaryotic genomes reveals clear species boundaries", Nat Communications 9, 5114 (2018)) and Han et al. ("ANI tools web: a web tool for fast genome comparison within multiple bacterial strains"; Database, 2016, 1-5).

As used herein, a "correlation" is a statistical measure that indicates the extent to which two or more variables, here plant growth enhancement and identified genetic elements, occur together. A positive correlation indicates that a microbial strain containing a given genetic element is likely to enhance plant growth.

As used herein, a "pan-genome" is the entire set of genes for the microbial population being screened in a plant colonization efficiency screen. Thus, a pan-genome may represent the entire set of genes for a particular species, or the entire set of genes in multiple different species of the same genus or even the entire set of genes for multiple species classified in more than a single genus, where the strains in the population are from closely related genera.

As used herein a "genetic element" refers to an element in a DNA or RNA molecule that comprises a series of adjacent nucleotides at least 20 nucleotides in length and up to 50, 100, 1,000, or 10,000 or more, nucleic acids in length. A genetic element may comprise different groups of adjacent nucleic acids, for example, where the genome of a plant-associated microorganism contains introns and exons. The genetic element may be present on a chromosome or on an extrachromosomal element, such as a plasmid. In eukaryotic plant-associated microorganisms, the genetic element may be present in the nucleus or in the mitochondria. In some embodiments, the genetic element is a functional genetic element (e.g., a gene) that encodes a protein.

As used herein, the terms "homologous" or "homologue" or "ortholog" refer to related genetic elements or proteins encoded by the genetic elements that are determined based on the degree of sequence identity. These terms describe the relationship between a genetic element or encoded protein found in one isolate, species or strain and the corresponding or equivalent genetic element or protein in another isolate, species or strain. As used herein, a particular genetic element in a first isolate, species or strain is considered equivalent to a genetic element present in a second isolate, species or strain when the proteins encoded by the genetic element in the isolates, species or strains have at least 50 percent identity. Percent identity can be determined using a number of software programs available in the art including BLASTP, ClustalW, ALLALIGN, DNASTAR, SIM, SEQALN, NEEDLE, SSEARCH and the like.

As used herein, the term "cultivate" means to grow a plant. A cultivated plant can be one grown and raised on a large agricultural scale or on a smaller scale, including for example a single plant.

As used herein, the term "hydroponic", "hydroponics" or "hydroponically" refers to a method of cultivating plants in the absence of soil.

As used herein, the term "mitigating", "mitigate", or "mitigation" refers to a reduction of something or a combination of things.

Where a term is provided in the singular, other embodiments described by the plural of that term are also provided.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Further Description

Isolated *Methylobacterium* strains that mitigate methane directly and/or by impacting the microbiome in a plant environment, are provided herein. Also provided are compositions comprising *Methylobacterium* strains that mitigate methane and one or more additional *Methylobacterium* strains that enhance early growth of plants, improve propagation/transplant vigor, increase nutrient uptake, improve stand establishment, improve stress tolerance, increase yield, and/or increase a plant's ability to utilize nutrients, and compositions useful for treatment of fields, wasteland, animal feed, wetlands, landfills, waste, plants, seeds, or plant parts with such strains are provided herein.

*Methylobacterium* strains that mitigate methane provided herein also provide benefits to a treated plant or a plant grown in treated soil, wherein such benefits include, but are not limited to enhanced early growth of plants, improved propagation/transplant vigor, increased nutrient uptake, improved stand establishment, improved stress tolerance, increased yield, and/or increased ability to utilize nutrients. In some embodiments, methane mitigation by *Methylobacterium* strains provided herein is the result of enzymatic oxidation of methane by the activity of soluble methane monooxygenase enzyme components encoded by genetic elements present in the *Methylobacterium* strains. In some embodiments, *Methylobacterium* strains mitigate methane by impacting other microbial populations or the activity of other microbial populations in the plant environment, for example by increasing activity or populations of methanotrophs, or decreasing the activity or populations of methanogens. In some embodiments, early growth enhancement results in increased yield at harvest, for example increased harvested seed yield.

In certain embodiments, the *Methylobacterium* in the composition is selected from the group consisting of NLS0737, NLS0770, NLS5278, NLS5334, NLS5480, NLS5549, and variants thereof. In certain embodiments, the composition further comprises one or more *Methylobacterium* selected from the group consisting of LGP2000 (NRRL B-50929), LGP2001 (NRRL B-50930), LGP2002 (NRRL B-50931), LGP2003 (NRRL B-50932), LGP2004 (NRRL B-50933), LGP2005 (NRRL B-50934), LGP2006 (NRRL B-50935), LGP2007 (NRRL B-50936), LGP2008 (NRRL B-50937), LGP2009 (NRRL B-50938), LGP2010 (NRRL B-50939), LGP2011 (NRRL B-50940), LGP2012 (NRRL B-50941), LGP2013 (NRRL B-50942), LGP2014 (NRRL B-67339), LGP2015 (NRRL B-67340), LGP2016 (NRRL B-67341), LGP2017 (NRRL B-67341), LGP2018 (NRRL B-67742), LGP2019 (NRRL B-67743), NLS0497 (NRRL B-67925), NLS0693 (NRRL B-67926), NLS1179 (NRRL B-67929), LGP2167 (NRRL B-67927), LGP2020 (NRRL-B-67892), LGP2021 (NRRL-B-68032), LGP2022 (NRRL-B-68033), LGP2023 (NRRL-B-68034), LGP2029 (NRRL B-68065), LGP2030 (NRRL B-68066), LGP2031 (NRRL B-68067), LGP2033 (NRRL B-68068), LGP2034 (NRRL B-68069), and variants thereof.

In certain embodiments, the plants are grown in a field, an irrigated or flooded field, hydroponically or in an aeroponic plant cultivation system. In certain embodiments, the *Methylobacterium* in the composition is selected from the group consisting of NLS0737, NLS0770, NLS5278, NLS5334, NLS5480, NLS5549, and variants thereof, and used to treat wetlands, landfills, or waste.

Also provided is an isolated *Methylobacterium* NLS0737, NLS0770, NLS5278, NLS5334, NLS5480, or NLS5549. In certain embodiments the *Methylobacterium* in the composition has the ability to mitigate methane directly by oxidation of methane by sMMO. In some embodiments, *Methylobacterium* strains facilitate oxidization of $CH_4$ into methanol ($CH_3OH$) followed by the incorporation of that carbon into bacterial biomass, or its oxidation to $CO_2$ and $H_2O$.

In certain embodiments, the *Methylobacterium* in the composition is NLS0737, NLS0770, NLS5278, NLS5334, NLS5480, NLS5549, or variants thereof. In certain embodiments, the *Methylobacterium* in the composition has the ability to use methane as a carbon source for growth. Such strains find use as described herein for mitigating methane production, for example in agricultural applications, including plant production in flooded fields, for reducing methane produced in animal production, such as cattle or dairy industries, or for reducing natural methane sources such as exist in wetlands or other natural water sources, (including but not limited to lakes, rivers, mangroves, marshes, bogs and streams), in geological sources, or in gases produced as the result of wildfires, wild animals, or insects. Such strains find use as described herein for mitigating methane production, for example in wetland, landfill, or waste applications for reducing methane produced in animal production, such as cattle or dairy industries, or for reducing natural methane sources such as exist in wetlands or other natural water sources, (including but not limited to lakes, rivers, marshes, bogs and streams), in geological sources, or in gases produced as the result of wildfires, wild animals, or insects. By reducing methane resulting from such practices or present in such sources, the concentration of atmospheric greenhouse gases can be reduced and decrease the potential for methane to have detrimental effects, particularly in contributing to global warming. In some embodiments, *Methylobacterium* strains provided herein not only mitigate atmospheric methane levels associated with agricultural crop production, but also provide additional benefits to a treated plant.

Further provided are methods of improving production of plants including rice, by treatment with one or more *Methylobacterium* strains provided herein. In certain embodiments, a *Methylobacterium* in the composition is NLS0737, NLS0770, NLS5278, NLS5334, NLS5480, or NLS5549. In certain embodiments, the composition is applied to rice or a field or paddy where rice is grown, and the composition further comprises one of more of LGP2016, LGP2017, and LGP2019. In some embodiments, treatment with *Methylobacterium* NLS0737, NLS0770, NLS5278, NLS5334, NLS5480, or NLS5549 improves plant production, for example by enhanced early growth of treated plants or plants grown from treated seeds in comparison to an untreated control plant or in comparison to a control plant grown from an untreated seed. Such enhanced early growth is measured, for example, by an increase in biomass of treated plants, including increased shoot, leaf, root, or whole seedling biomass. Increased early growth can result in various improvements in plant production, including for example increased biomass production or yield of harvested plants, increased and/or more uniform fruit production, faster seed set, earlier maturation, increased rate of leaf growth, increased rate of root growth, increased seed yield, and decreased cycle time in comparison to an untreated control plant or in comparison to a control plant grown from an untreated seed. In certain embodiments, application of *Methylobacterium* strains as provided herein provides for a 1%, 2%, 3%, 4%, 5%, 6%, 7%, 8%, 9%, 10%, 12%, 15%, 17%, 20%, 30% or 40% increase in any of the aforementioned traits in comparison to an untreated control plant or in comparison to a control plant grown from an untreated seed. In some embodiments, production is enhanced by increased rooting, for example of plant cuttings, where such increased rooting can result in decreased cycling time and/or increased biomass or yield of the treated plants.

In some embodiments, compositions comprising a *Methylobacterium* capable of mitigating methane further comprise one or more *Methylobacterium* strains that provide for at least one plant benefit selected from the group consisting of enhanced early growth of plants, improved yield of a crop and/or crop product, improved propagation/transplant vigor, increased nutrient uptake, improved stand establishment, improved stress tolerance, improved pest resistance, improved pathogen resistance, fruit ripening and/or increased ability of the plant to utilize nutrients, such as nitrogen, potassium, sulfur, cobalt, copper, zinc, phosphorus, boron, iron, and manganese. In some embodiments, such compositions comprise a *Methylobacterium* that fixates nitrogen.

In some embodiments, an additional *Methylobacterium* strain in a composition is selected from the group consisting of LGP2000 (NRRL B-50929), LGP2001 (NRRL B-50930), LGP2002 (NRRL B-50931), LGP2003 (NRRL B-50932), LGP2004 (NRRL B-50933), LGP2005 (NRRL B-50934), LGP2006 (NRRL B-50935), LGP2007 (NRRL B-50936), LGP2008 (NRRL B-50937), LGP2009 (NRRL B-50938), LGP2010 (NRRL B-50939), LGP2011 (NRRL B-50940), LGP2012 (NRRL B-50941), LGP2013 (NRRL B-50942), LGP2014 (NRRL B-67339), LGP2015 (NRRL B-67340), LGP2016 (NRRL B-67341), LGP2017 (NRRL B-67741), LGP2018 (NRRL B-67742), LGP2019 (NRRL B-67743), NLS0497 (NRRL B-67925), NLS0693 (NRRL B-67926), NLS1179 (NRRL B-67929), LGP2167 (NRRL B-67927), LGP2020 (NRRL-B-67892), LGP2021 (NRRL-B-68032), LGP2022 (NRRL-B-68033), LGP2023 (NRRL-B-68034), LGP2029 (NRRL B-68065), LGP2030 (NRRL B-68066), LGP2031 (NRRL B-68067), LGP2033 (NRRL B-68068), LGP2034 (NRRL B-68069), and variants thereof.

In certain embodiments, the compositions provided herein enhance uptake and/or utilization of one or more nutrients and/or enhances nitrogen use efficiency of a treated plant or a plant grown in treated soil, and a *Methylobacterium* in the composition is selected from the group consisting of LGP2001 (NRRL B-50930), LGP2002 (NRRL B-50931), LGP2009 (NRRL B-50938), LGP2015 (NRRL B-67340), LGP2016 (NRRL B-67341), LGP2017 (NRRL B-67741), LGP2018 (NRRL B-67742), LGP2019 (NRRL B-67743), NLS0693 (NRRL B-67926), LGP2167 (NRRL B-67927), LGP2020 (NRRL-B-67892), LGP2021 (NRRL-B-68032), LGP2022 (NRRL-B-68033), LGP2023 (NRRL-B-68034), LGP2029 (NRRL B-68065), LGP2030 (NRRL B-68066), LGP2031 (NRRL B-68067), LGP2033 (NRRL B-68068), LGP2034 (NRRL B-68069), and variants thereof.

In certain embodiments, the *Methylobacterium* in the compositions provided herein comprise one or more genetic elements associated with the ability to enhance early plant growth, wherein the one or more genetic elements (i) is recD2_2 or pinR; or (ii) the one or more genetic elements encode a protein having a consensus amino acid sequence of SEQ ID NO: 17 to SEQ ID NO: 23. In some embodiments, *Methylobacterium* in the compositions provided herein that improve early plant growth also impart one or more additional beneficial traits to treated plants or plants grown from treated plant parts or seeds, wherein the trait is enhanced uptake of nutrients, enhanced assimilation of nutrients, and/or enhanced nutrient use efficiency. In some embodiments, plants treated with *Methylobacterium* isolates provided herein demonstrate enhanced nitrogen use efficiency. In certain embodiments, the compositions provided herein enhance yield of a treated crop or crop product of a treated crop plant or a crop plant grown in treated soil. In certain embodiments, the crop is rice, and the compositions comprise a *Methylobacterium* capable of mitigating methane selected from the group consisting of NLS0770 (NRRL-B-

68075), NLS5278 (NRRL-B-68186), NLS5334 (NRRL-B-68187), NLS5480 (NRRL-B-68188), NLS5549 (NRRL-B-68189), and variants thereof, and an additional *Methylobacterium* providing for enhanced yield of rice. In some embodiments, the additional *Methylobacterium* is selected from the group consisting of LGP2016 (NRRL B-67341), LGP2017 (NRRL B-67741), LGP2019 (NRRL B-67743), and variants thereof.

Various methods for identifying a *Methylobacterium* strain that mitigate methane are also provided herein. In one method, a wetland, field, plant, plant part or seed is treated with at least a first *Methylobacterium* strain and methane emissions measured and compared to emissions from control strains and/or other tested strains to identify strains that mitigate methane. In some embodiments, *Methylobacterium* isolates selected for testing in such methods comprise one or more genetic elements encoding protein components of soluble methane monooxygenase.

Methane utilizing strains for use in the methods described herein may be identified by the presence of one or more genes encoding a protein component of soluble methane monooxygenase (sMMO). Soluble MMO typically contains multiple protein components: a reductase "C" component, a regulatory "B" component and a hydroxylase "A" component containing alpha and beta chains. In some embodiments, a *Methylobacterium* strain capable of mitigating methene is identified by the presence of a gene encoding a methane monooxygenase component protein having an amino acid sequence that has 65% to 100% identity to an sMMO component protein amino acid sequence of SEQ ID NOS: 1-8. Strains NLS0737 and NLS0770 have sequences encoding proteins with amino acid sequences SEQ ID NOS: 1-4. Strains NLS5278, NLS5334, NLS5480, and NLS5549 have sequences encoding proteins with SEQ ID NOS: 5-8. In some embodiments, a *Methylobacterium* strain having the ability to use methane as a carbon source for growth is identified using an assay to demonstrate growth of the *Methylobacterium* strain on methane as the sole carbon source. In some embodiments, a *Methylobacterium* strain for use in mitigating methane emissions is NLS0737, NLS0770, NLS5278, NLS5334, NLS5480, or NLS5549, or variants thereof.

Genetic elements and encoded proteins correlated with methane oxidation described herein were identified by screening a population of *Methylobacterium* strains and identifying strains that contain a methane monooxygenase (hits) and strains which lack a methane monooxygenase (non-hits). Genetic elements encoding methane monooxygenase component proteins are provided herein as SEQ ID NOS: 9-16. Additional *Methylobacterium* strains capable of mitigating methane can be identified by the presence of one or more encoding sequences of SEQ ID NOs:9-16, or encoding sequences having from 65-100% identify to SEQ ID NOs:9-16. Strains NLS0737 and NLS0770 comprise sequences with high identity to SEQ ID NOs: 5-8. Strains NLS5278, NLS5334, NLS5480, and NLS5549 comprises sequences high identity to SEQ ID NOS: 13-16. Such genetic elements can be used, for example to generate modifications of sMMO component proteins having improved activity, to transform *Methylobacterium* strains which lack sMMO genes to generate additional methane oxidizing strains, and to provide or improve methane oxidation capability in non-*Methylobacterium* microbes. Recombinant expression constructs can be generated for expression of one or more of the proteins encoded by SEQ ID NOS: 1-8 or improved modifications thereof in a microbial cell. SEQ ID NOS: 9-16 or variations thereof having from 65-100% identify to SEQ ID NOs:9-16 find use in such constructs.

In some embodiments, sMMO protein component encoding genetic elements are encoded on one or more plasmids present in a *Methylobacterium* strain capable of oxidizing methane. In such embodiments, sMMO encoding sequences can be transferred using mobilized plasmids to *Methylobacterium* strains which lack sMMO genes to generate transconjugant methane oxidizing *Methylobacterium* strains. Synthetic vector systems or native mobilizable plasmids are useful in generation of transformed microbial strains. In one embodiment, a synthetic vector system will include ColE1 for high-copy maintenance and cloning in *E. Coli*, an antibiotic selection marker, oriV for *Methylobacterium* compatible origin of replication, oriT for mobilization and conjugative transfer between bacterial hosts, and a module providing for expression of sMMO protein components expressed by native or heterologous expression elements. Heterologous expression elements that find use in such synthetic vector systems include promoters from phage such as the phage PR, T5 and Sp6 promoters, promoters from lac and trp operons and native *Methylobacterium* promoters, including the promoter for methanol dehydrogenase mxaF1 and others, such as described by Zhang and Lidstrom (2003). Transconjugation and other methods for genetically modifying microbial genomes with sMMO encoding sequences provided herein are described, for example in US20210171961, the content of which is incorporated herein by reference in its entirety.

Also provided herein are methods of mitigating methane, enhancing growth and/or yield of a plant, comprising treating a plant or soil where said a plant is growing or will be grown, with a *Methylobacterium* isolate that uses methane as a carbon source selected from the group consisting of NLS0770 (NRRL B-68075), NLS0737 (NRRL B-68074), NLS5278, NLS5334, NLS5480, NLS5549, and variants thereof, and/or a *Methylobacterium* isolate that enhances uptake and/or utilization of one or more nutrient components of a fertilizer that is applied to improve cultivation of said plant. In some embodiments the one or more nutrient components is selected from the group consisting of nitrogen, phosphorus, potassium and iron. In some embodiments, the *Methylobacterium* isolate is selected from the group consisting of LGP2001 (NRRL B-50930), LGP2002 (NRRL B-50931), LGP2009 (NRRL B-50938), LGP2015 (NRRL B-67340), LGP2016 (NRRL B-67341), LGP2017 (NRRL B-67741), LGP2018 (NRRL B-67742), LGP2019 (NRRL B-67743), NLS0693 (NRRL B-67926), LGP2167 (NRRL B-67927), LGP2020 (NRRL-B-67892), LGP2021 (NRRL-B-68032), LGP2022 (NRRL-B-68033), LGP2023 (NRRL-B-68034), LGP2029 (NRRL B-68065), LGP2030 (NRRL B-68066), LGP2031 (NRRL B-68067), LGP2033 (NRRL B-68068), LGP2034 (NRRL B-68069), and variants thereof.

In some embodiments, treatment with said *Methylobacterium* isolates allows for reduced levels of fertilizer or various fertilizer components during cultivation of said plant. In some embodiments, the plant is an agricultural row crop. In some embodiments, a *Methylobacterium* treated plant can be cultivated using reduced rates of fertilizer as compared to standard application rates for said plant. In some embodiments, fertilizer application can be reduced by 5%, 10%, 15%, 20%, 25%, 30%, 35%, 40% or more. In certain embodiments, application of fertilizer can be reduced by at least 25%. In some embodiments the amount of one or more components of said fertilizer is reduced. In some embodiments levels of nitrogen, phosphorus, potassium and/or iron are reduced by 5%, 10%, 15%, 20%, 25%, 30%, 35%, 40% or more. Optimal fertilizer and/or fertilizer components may vary depending on the crop, soil, geographical location. Optimal fertilizer levels can also be determined experimentally, for example by measuring yield at increasing amounts of fertilizer, where the optimal fertilizer concentration is identified by determining the level after which no further yield advantage is observed. An example of determining the optimal nitrogen level for growth is described in Sharma et al. (Indian J. Genet. (2018) 78:292-301).

In some embodiments, methods for enhancing growth and/or yield of a plant comprise application of a composition comprising one or more *Methylobacterium* isolates that mitigate methane, selected from the group consisting of NLS0770 (NRRL B-68075), NLS0737 (NRRL B-68074), NLS5278, NLS5334, NLS5480, and NLS5549, and optionally, one or more *Methylobacterium* isolates selected from the group consisting of LGP2001 (NRRL B-50930), LGP2002 (NRRL B-50931), LGP2009 (NRRL B-50938), LGP2015 (NRRL B-67340), LGP2016 (NRRL B-67341), LGP2017 (NRRL B-67741), LGP2018 (NRRL B-67742), LGP2019 (NRRL B-67743), NLS0693 (NRRL B-67926), LGP2167 (NRRL B-67927), LGP2020 (NRRL-B-67892), LGP2021 (NRRL-B-68032), LGP2022 (NRRL-B-68033), LGP2023 (NRRL-B-68034), LGP2029 (NRRL B-68065), LGP2030 (NRRL B-68066), LGP2031 (NRRL B-68067), LGP2033 (NRRL B-68068), LGP2034 (NRRL B-68069), and variants thereof and a fertilizer. In some embodiments, the plant is an agricultural row crop. In some embodiments, the plant is a leafy green plant. In some embodiments, a leafy green plant is treated, and the leafy green plant is cultivated in a hydroponic or aeroponic plant growth environment. In some embodiments, the fertilizer, or component of the fertilizer are present at a reduced rate compared to the optimal level for the plant. In some embodiments, the nitrogen level is reduced by 5%, 10%, 15%, 20%, 25%, 30%, 35%, 40% or more.

In some embodiments of methods provided herein, a pasture, wasteland or field is treated. In some embodiments of methods provided herein, treatment is done in a waste facility. In some embodiments of method provided herein, the field is flooded or irrigated. In some embodiments of the method provided herein, a plant seed is treated. In certain other embodiments, a plant seedling or part thereof is treated. In some embodiments, a plant shoot or seedling is treated. In some embodiments, the treated plant is cultivated to the second true leaf stage (V2) and harvested to determine root and shoot biomass and nitrogen levels. In some embodiments, the treated plant is cultivated for 10 to 14 days. In some embodiments, the treated plant is cultivated for 14 to 28 days. In some embodiments, the treated plant is cultivated for 28 or more days prior to harvest and analysis of tissue samples to determine levels of nitrogen and other mineral nutrients. In some embodiments, treated plant seeds or seedlings are cultivated in a hydroponic system or an aeroponic plant growth system. A hydroponics system can be a water culture system, a nutrient film technique, an ebb and flow system, a drip system, or a wick system. In an aeroponic system, plants are grown in an air or mist environment without the use of soil. In some embodiments, the hydroponic or aeroponic system can be a variation of any of these types or a combination of one or more systems. In some embodiments, a hydroponic or aeroponic system is advantageous over a soil based cultivation system for determining effects of *Methylobacterium* strains due to the presence of fewer background microorganisms. Various inert substrates can be used to support the plants, seedlings and root systems in hydroponic or aeroponic growth, including but not limited to perlite, rockwool, clay pellets, foam cubes, rock, peat moss, or vermiculite.

In some embodiments, a *Methylobacterium* strain that enhances plant growth or nitrogen use efficiency, is more efficient at colonizing a plant host cell or tissue, as compared to other *Methylobacterium* strains. Methods for identifying microbial strains having enhanced colonization efficiency are described in WO2020163027 (PCT/US2020/012041), which is incorporated herein by reference in its entirety. In some embodiments, a *Methylobacterium* strain that mitigates or decreases methane from agriculture lands, also imparts a trait improvement to said plant selected from increased biomass production, decreased cycle time, increased rate of leaf growth, decreased time to develop two true leaves, increased rate of root growth, and increased seed yield.

Various methods of using *Methylobacterium* strains to mitigate methane, enhance early growth or rooting, improve propagation/transplant vigor, increase nutrient uptake, improve stand establishment, improve stress tolerance and/or increase a plant's ability to uptake and/or utilize nutrients, such as nitrogen, potassium, sulfur, cobalt, copper, zinc, phosphorus, boron, iron and manganese in plants, such as leafy green plants, row crops, *cannabis* and other specialty crops are provided herein. In certain embodiments, *Methylobacterium* treatment of a row crop, including but not limited to corn, soybean, rice, canola, and wheat, results in enhanced plant growth and yield. In certain embodiments, the crop is rice and the *Methylobacterium* is one or more isolates selected from the group consisting of NLS0770, NLS0737, NLS5278, NLS5334, NLS5480, NLS5549, LGP2016 (ISO17), LGP2017 (ISO18), LGP2019 (ISO20) and variants thereof. In certain embodiments, *Methylobacterium* treatment of soil, agriculture land, including a field or a flooded and irrigated field, a seed, a leaf, a stem, a root, or a shoot can enhance early growth, propagation/transplant vigor, stand establishment, and/or stress tolerance as well as or alternatively enhance nutrient use efficiency.

Alternatively, such *Methylobacterium* may be applied to soil or other growth medium where plants are grown. *Methylobacterium* soil treatments or applications can include, but are not limited to, fields (e.g. flooded or irrigated fields), in-furrow applications (e.g., before, during, and/or after seed deposition), soil drenches, distribution of granular or other dried formulations to the soil (e.g., before, during, and/or after seed deposition or plant growth). *Methylobacterium* treatments for plants grown in hydroponic systems can include seed treatments prior to germination, foliar applications to germinated plants or parts thereof, and applications in a liquid solution used in the hydroponic system. In certain embodiments, *Methylobacterium* treatment of a plant can include application to the seed, plant, and/or a part of the plant and can thus comprise any *Methylobacterium* treatment or application resulting in colonization of the plant by the *Methylobacterium*. In some embodiments, application of *Methylobacterium* to crops that are propagated by cutting can enhance growth and/or rooting of such plants. Field transplants of such treated and rooted cuttings may demonstrate decreased cycling time, and/or improved biomass and/or yield as a result of such treatments.

Treatments or applications to plants described herein can include, but are not limited to, spraying, coating, partially coating, immersing, and/or imbibing the field, seed, plant or plant parts with the *Methylobacterium* strains and compositions comprising the same provided herein. In certain embodiments, soil, a seed, a leaf, a stem, a root, a tuber, or a shoot can be sprayed, immersed and/or imbibed with a liquid, semi-liquid, emulsion, or slurry of a composition provided herein.

Also disclosed are a plant, a plant part or a seed at least partially coated with the compositions described herein. In particular, the plant is a rice plant.

In certain embodiments, methane oxidizing *Methylobacterium*, such as NLS0737, NLS0770, NLS5278, NLS5334, NLS5480, or NLS5549 described herein are applied as foliar sprays to row crops. In some embodiments, the crop is rice, and plants are treated with an initial foliar application at a flooded stage. In some embodiments, foliar applications are made when a rice paddy is at full flood stage. In some embodiments, additional foliar applications of *Methylobacterium* are made. In some embodiments, a second foliar application of *Methylobacterium* is made from 20-40 days following the initial application. In some embodiments, *Methylobacterium* is also applied as a foliar spray prior to the booting stage of development (characterized by swelling of the flag leaf sheath caused by an increase in the size of the panicle). In some embodiments, a foliar spray is applied 14 days prior to booting stage. In some embodiments, *Methylobacterium* is applied initially as a foliar spray at full flood stage, followed by a second foliar application approximately 4-6 weeks later, for example around 30 days later. In some embodiments, a third foliar application of *Methylobacterium* is made not later than 14 days prior to booting stage.

Such treatments, applications, seed immersion, or imbibition can be sufficient to provide for mitigation of greenhouse gas emissions, enhanced early growth and/or increased levels of one or more mineral nutrients and/or vitamins content in harvestable tissue from a treated plant or plant grown from a treated seed in comparison to an untreated plant or plant grown from an untreated seed. Enhanced early growth can lead to further improvements in plant production including an increase in biomass of treated plants, such as increased shoot, root, or whole seedling biomass. Enhanced early growth can result in various additional improvements in plant production, including for example increased yield of harvested plants or harvested plant parts, increased and/or more uniform fruit production, faster seed set, earlier maturation, increased rate of leaf growth, increased rate of root growth, increased seed yield, and decreased cycle time. In certain embodiments, plant seeds or cuttings can be immersed and/or imbibed for at least 1, 2, 3, 4, 5, or 6 hours. Such immersion and/or imbibition can, in certain embodiments, be conducted at temperatures that are not deleterious to the plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation. Seed treatments can be effected with both continuous and/or batch seed treaters.

In certain embodiments, the coated seeds can be prepared by slurrying seeds with a coating composition comprising a *Methylobacterium* strain that increases the levels of one or more mineral nutrients and/or vitamins and air-drying the resulting product. Air-drying can be accomplished at any temperature that is not deleterious to the seed or the *Methylobacterium*, but will typically not be greater than 30 degrees Centigrade. The proportion of coating that comprises the *Methylobacterium* strain includes, but is not limited to, a range of 0.1 to 25% by weight of the seed or other plant part, 0.5 to 5% by weight of the seed or other plant part, and 0.5 to 2.5% by weight of the seed or other plant part.

In certain embodiments, a solid substance used in the seed coating or treatment will have a *Methylobacterium* strain that increases mineral nutrient and or vitamin content adhered to a solid substance as a result of being grown in biphasic media comprising the *Methylobacterium* strain, solid substance, and liquid media. Methods for growing *Methylobacterium* in biphasic media include those described in U.S. Pat. No. 9,181,541, which is specifically incorporated herein by reference in its entirety. In certain embodiments, compositions suitable for treatment of a seed or plant part can be obtained by the methods provided in U.S. Pat. No. 10,287,544, which is specifically incorporated herein by reference in its entirety. Various seed treatment compositions and methods for seed treatment disclosed in U.S. Pat. Nos. 5,106,648, 5,512,069, and 8,181,388 are incorporated herein by reference in their entireties and can be adapted for treating seeds with compositions comprising a *Methylobacterium* strain.

In certain embodiments where plant seeds are treated with *Methylobacterium* compositions provided herein, the compositions further comprise one or more lubricants to ensure smooth flow and separation (singulation) of seeds in the seeding mechanism, for example a planter box. Lubricants for use in such compositions include talc, graphite, polyethylene wax based powders (such as Fluency Agent), protein powders, for example soybean protein powders, or a combination of protein powders and a lipid, for example lecithin or a vegetable oil. Lubricants can be applied to seeds simultaneously with application of *Methylobacterium*, or may be mixed with *Methylobacterium* prior to application of the compositions to the seeds.

In certain embodiments, treated plants are cultivated in a hydroponic system. In some embodiments, plant seeds are treated and plants are grown from the treated seeds continuously in the same cultivation system. In some embodiments, plant seeds are treated and cultivated in a hydroponic nursery to produce seedlings. The seedlings transferred to a different hydroponic system, for example for commercial production of leafy greens. In some embodiments, a *Methylobacterium* strain that enhances early growth or increases the levels of one or more mineral nutrients and/or vitamins persists in the seedlings transferred to a greenhouse production system and continues to provide advantages such as improved micronutrient and/or vitamin content and/or biomass production, through the further growth of the leafy green plant. In some embodiments, plant seedlings transferred to a greenhouse production system may be further treated with one or more other *Methylobacterium* strains that increase the levels of one or more mineral nutrients and/or vitamins prior to, during or after transfer to the production system.

In certain embodiments, the composition used to treat the pasture, wasteland, field, seed, plant, or plant part can contain a *Methylobacterium* strain and an agriculturally acceptable excipient. Agriculturally acceptable excipients include, but are not limited to, woodflours, clays, activated carbon, diatomaceous earth, fine-grain inorganic solids, calcium carbonate and the like. Clays and inorganic solids that can be used with the include, but are not limited to, calcium bentonite, kaolin, china clay, talc, perlite, mica, vermiculite, silicas, quartz powder, montmorillonite and mixtures thereof. Agriculturally acceptable excipients also include various lubricants (which can provide for smooth flow and separation (singulation) of seeds) such as talc, graphite, polyethylene wax based powders (such as Fluency Agent), protein powders, for example soybean protein powders, or a combination of protein powders and a lipid, for example lecithin or a vegetable oil.

Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethyl-propylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethyl-cellulose, chitosan, polyethylene oxide, acrylamide polymers and copolymers, polyhydroxyethyl acrylate, methyl-acrylamide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with compositions comprising a suitable *Methylobacterium* strain. In certain embodiments, the seed and/or seedling is exposed to the composition by providing the *Methylobacterium* strain in soil in which the plant or a plant arising from the seed are grown, or other plant growth media in which the plant or a plant arising from the seed are grown. Examples of methods where the *Methylobacterium* strain is provided in the field and soil include in furrow applications, soil drenches, and the like.

In certain embodiments, NLS0737, NLS0770, NLS5278, NLS5334, NLS5480, NLS5549, LGP2022, LGP2023, LGP2021 or variants or combinations thereof will also find use in treatment of other plant species to mitigate methane and/or enhance early growth, including, for example field crops, leafy greens, herbs, ornamentals, turf grasses and trees grown in commercial production, such as conifer trees. Without limitation, such additional plant species include corn, soybean, cruciferous or *Brassica* sp. vegetables (e.g., *B. napus, B. rapa, B. juncea*), alfalfa, rice, rye, wheat, barley, oats, sorghum, millet (e.g., pearl millet (*Pennisetum glaucum*), proso millet (*Panicum miliaceum*), foxtail millet (*Setaria italica*), and finger millet (*Eleusine coracana*)), sunflower, safflower, tobacco, potato, peanuts, cotton, species in the genus *Cannabis* (including, but not limited to, *Cannabis sativa* and industrial hemp varieties), alfalfa, clover, cover-crops, sweet potato (*Ipomoea batatus*), cassava, coffee, coconut, ornamentals (including, but not limited to, azalea, hydrangea, hibiscus, roses, tulips, daffodils, petunias, carnation, poinsettia, and chrysanthemum), conifers (including, but not limited to pines such as loblolly pine, slash pine, ponderosa pine, lodge pole pine, and Monterey pine; Douglas-fir; Western hemlock; Sitka spruce; redwood; true firs such as silver fir and balsam fir; cedars such as Western red cedar and Alaska yellow-cedar) and turfgrass (including, but are not limited to, annual bluegrass, annual ryegrass, Canada bluegrass, fescue, bentgrass, wheatgrass, Kentucky bluegrass, orchard grass, ryegrass, redtop, Bermuda grass, St. Augustine grass, and zoysia grass); fruit (including but not limited to citrus, pome, and tropical fruit); nuts; and tea.

Leafy green plants that can be treated include vegetable crop with edible leaves, for example, spinach, kale, lettuce (including but not limited to romaine, butterhead, iceberg and loose leaf lettuces), collard greens, cabbage, beet greens, watercress, swiss chard, arugula, escarole, endive, bok choy and turnip greens. Leafy green plants as used herein also refers to plants grown for harvest of microgreens and/or herbs, including but not limited to lettuce, cauliflower, broccoli, cabbage, watercress, arugula, garlic, onion, leek, amaranth, swill chard, been, spinach, melon, cucumber, squash, basil, celery, cilantro, radish, radicchio, chicory, dill, rosemary, French tarragon, basil, *Pennisetum*, carrot, fennel, beans, peas, chickpeas, and lentils.

In certain embodiments, a *Methylobacterium* strain used to treat a given cultivar or variety of plant seed, plant or plant part can be a *Methylobacterium* strain that was isolated from a different plant species, or a different cultivar or variety of the plant species being treated, and is thus heterologous or non-resident to the treated plant or plant part.

In certain embodiments, a manufactured combination composition comprising two or more *Methylobacterium* strains can be used to treat a field, seed or plant part in any of the methods provided herein. Such manufactured combination compositions can be made by methods that include harvesting monocultures of each *Methylobacterium* strain and mixing the harvested monocultures to obtain the manufactured combination composition of *Methylobacterium*. In certain embodiments, the manufactured combination composition of *Methylobacterium* can comprise *Methylobacterium* isolated from different plant species or from different cultivars or varieties of a given plant.

In certain embodiments, a manufactured combination composition comprising one or more *Methylobacterium* strains and a second biological can be used to treat a field, seed or plant part in any of the methods provided herein. Such manufactured combination compositions can be made by methods that include harvesting monocultures of each strain and mixing the harvested monocultures to obtain the manufactured combination composition of *Methylobacterium*. In certain embodiments, the manufactured combination composition of *Methylobacterium* and the second biological can comprise isolates from different plant species or from different cultivars or varieties of a given plant.

In certain embodiments, an effective amount of the *Methylobacterium* strain or strains used in treatment of plants, seeds or plant parts is a composition having a *Methylobacterium* titer of at least about $1\times10^6$ colony-forming units per milliliter, at least about $5\times10^6$ colony-forming units per milliliter, at least about $1\times10^7$ colony-forming units per milliliter, at least about $5\times10^8$ colony-forming units per milliliter, at least about $1\times10^9$ colony-forming units per milliliter, at least about $1\times10^{10}$ colony-forming units per milliliter, or at least about $3\times10^{10}$ colony-forming units per milliliter. In certain embodiments, an effective amount of the *Methylobacterium* strain or strains is a composition with the *Methylobacterium* at a titer of about least about $1\times10^6$ colony-forming units per milliliter, at least about $5\times10^6$ colony-forming units per milliliter, at least about $1\times10^7$ colony-forming units per milliliter, or at least about $5\times10^8$ colony-forming units per milliliter to at least about $6\times10^{10}$ colony-forming units per milliliter of a liquid or an emulsion. In certain embodiments, an effective amount of the *Methylobacterium* strain or strains is a composition with the *Methylobacterium* at least about $1\times10^6$ colony-forming units per gram, at least about $5\times10^6$ colony-forming units per gram, at least about $1\times10^7$ colony-forming units per gram, or at least about $5\times10^8$ colony-forming units per gram to at least about $6\times10^{10}$ colony-forming units of *Methylobacterium* per gram of the composition. In certain embodiments, an effective amount of a composition provided herein can be a composition with a *Methylobacterium* titer of at least about $1\times10^6$ colony-forming units per gram, at least about $5\times10^6$ colony-forming units per gram, at least about $1\times10^7$ colony-forming units per gram, or at least about $5\times10^8$ colony-forming units per gram to at least about $6\times10^{10}$ colony-forming units of *Methylobacterium* per gram of particles in the composition containing the particles that comprise a solid substance wherein a mono-culture or co-culture of *Methylobacterium* strain or strains is adhered thereto. In certain embodiments, an effective amount of a composition provided herein to a plant or plant part can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL in a composition comprising an emulsion wherein a mono-culture or co-culture of a *Methylobacterium* strain or strains adhered to a solid substance is provided therein or grown therein. In certain embodiments, an effective amount of a composition provided herein can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL in a composition comprising an emulsion wherein a mono-culture or co-culture of a *Methylobacterium* strain or strains is provided therein or grown therein.

In certain embodiments, an effective amount of a *Methylobacterium* strain or strains that provides for mitigation of green-house gas emissions is at least about $10^3$, $10^4$, $10^5$, or $10^6$ CFU per seed or treated plant part. In certain embodiments, an effective amount of *Methylobacterium* provided in a treatment of a seed or plant part is at least about $10^3$, $10^4$, $10^5$, or $10^6$ CFU to about $10^7$, $10^8$, $10^9$, or $10^{10}$ CFU per seed or treated plant part. In certain embodiments, the effective amount of *Methylobacterium* provided in a treatment of a seed or plant part is an amount where the CFU per seed or treated plant part will exceed the number of CFU of any resident naturally occurring *Methylobacterium* strain by at least 5-, 10-, 100-, or 1000-fold. In certain embodiments, the effective amount of *Methylobacterium* provided in a treatment of a seed or plant part is an amount where the CFU per seed or treated plant part will exceed the number of CFU of any resident naturally occurring *Methylobacterium* by at least 2-, 3-, 5-, 8-, 10-, 20-, 50-, 100-, or 1000-fold. In certain embodiments where the treated plant is cultivated in a hydroponic system, populations of naturally occurring *Methylobacterium* or other soil microbes will be minimal.

Non-limiting examples of *Methylobacterium* strains that can be used in methods provided herein are disclosed in Table 1. Other *Methylobacterium* strains useful in certain methods provided herein include variants of the *Methylobacterium* strains disclosed in Table 1. Also of use are various combinations of two or more strains or variants of *Methylobacterium* strains disclosed in Table 1 for treatment of plants or parts thereof.

TABLE 1

| *Methylobacterium* sp. strain | | | | |
|---|---|---|---|---|
| Deposit Identifier | Isolate No. | LGP NO. | USDA ARS NRRL No.[1] | Strain Source: Obtained from: |
| *Methylobacterium* sp. #1 | ISO01 | LGP2000 | NRRL B-50929 | a soybean plant grown in Saint Louis County, Missouri, USA |
| *Methylobacterium* sp. #2 | ISO02 | LGP2001 | NRRL B-50930 | a weed grown in Saint Louis County, Missouri, USA |
| *Methylobacterium* sp. #3 | ISO03 | LGP2002 | NRRL B-50931 | a mint plant grown in Saint Louis County, Missouri, USA |
| *Methylobacterium* sp. #4 | ISO04 | LGP2003 | NRRL B-50932 | a soybean plant grown in Saint Louis County, Missouri, USA |
| *Methylobacterium* sp. #5 | ISO05 | LGP2004 | NRRL B-50933 | a broccoli plant grown in Saint Louis County, Missouri, USA |
| *Methylobacterium* sp. #6 | ISO06 | LGP2005 | NRRL B-50934 | a corn plant grown in Saint Louis County, Missouri, USA |
| *Methylobacterium* sp. #7 | ISO07 | LGP2006 | NRRL B-50935 | a corn plant grown in Saint Louis County, Missouri, USA |
| *Methylobacterium* sp. #8 | ISO08 | LGP2007 | NRRL B-50936 | a corn plant grown in Saint Louis County, Missouri, USA |
| *Methylobacterium* sp. #9 | ISO09 | LGP2008 | NRRL B-50937 | a corn plant grown in Saint Louis County, Missouri, USA |
| *Methylobacterium* sp. #10 | ISO10 | LGP2009 | NRRL B-50938 | a corn plant grown in Saint Louis County, Missouri, USA |
| *Methylobacterium* sp. #11 | ISO11 | LGP2010 | NRRL B-50939 | a lettuce plant grown in Saint Louis County, Missouri, USA |

TABLE 1-continued

| | Isolate No. | LGP NO. | USDA ARS NRRL No.[1] | Strain Source: Obtained from: |
|---|---|---|---|---|
| Deposit Identifier | | | | |
| *Methylobacterium* sp. #12 | ISO12 | LGP2011 | NRRL B-50940 | a corn plant grown in Saint Louis County, Missouri, USA |
| *Methylobacterium* sp. #13 | ISO13 | LGP2012 | NRRL B-50941 | a tomato plant grown in Saint Louis County, Missouri, USA |
| *Methylobacterium* sp. #14 | ISO14 | LGP2013 | NRRL B-50942 | a tomato plant grown in Saint Louis County, Missouri, USA |
| *Methylobacterium* sp. #15 | ISO15 | LGP2014 | NRRL B-67339 | a soybean plant grown in Saint Louis County, Missouri, USA |
| *Methylobacterium* sp. #16 | ISO16 | LGP2015 | NRRL B-67340 | a yucca plant grown in Saint Louis County, Missouri, USA |
| *Methylobacterium* sp. #17 | ISO17 | LGP2016 | NRRL B-67341 | a soybean plant grown in Saint Louis County, Missouri, USA |
| *Methylobacterium* sp. #18 | ISO18 | LGP2017 | NRRL B-67741 | a *Dionaea muscipula* plant (Venus fly trap) grown in St. Charles, MO. |
| *Methylobacterium* sp. #19 | ISO19 | LGP2018 | NRRL B-67742 | an *Orchidaceae* spp. plant (orchid) grown in Saint Louis County, Missouri, USA |
| *Methylobacterium* sp. #20 | ISO20 | LGP2019 | NRRL B-67743 | a tomato plant grown in Saint Louis County, Missouri, USA Saint Louis County, Missouri, USA |
| *Methylobacterium* sp. #22 | ISO22 | NLS0497 | NRRL B-67925 | A cup plant (*Silphium perfoliatum* in5 |
| *Methylobacterium* sp. #23 | ISO23 | NLS0693 | NRRL B-67926 | a vinca vine (*Vinca minor*) in Saint Louis County, Missouri, USA |
| *Methylobacterium* sp. #24 | ISO24 | NLS1179 | NRRL B-67929 | Rainwater collected in Saint Louis County, Missouri, USA |
| *Methylobacterium* sp. #25 | ISO25 | LGP2167 | NRRL B-67927 | An *Acer ginnala* (Amur maple) grown in Saint Louis County, Missouri, USA |
| *Methylobacterium* sp. #26 | ISO26 | LGP2020 | NRRL-B-67892 | A *Lagerstroemia indica* (crape myrtle) plant grown in Saint Louis County, Missouri, USA |
| *Methylobacterium* sp. #28 | ISO28 | LGP2021 | NRRL-B-68032 | A *Cichorium intybus* (chicory) plant growing in Saint Louis County, Missouri, USA |
| *Methylobacterium* sp. #29 | ISO29 | LGP2022 | NRRL-B-68033 | A *Coronilla vario* (crown vetch) plant growing in Saint Louis County, Missouri, USA |
| *Methylobacterium* sp. #30 | ISO30 | LGP2023 | NRRL-B-68034 | A *Catharanthus roseus* (periwinkle) growing in Fort Myers, Florida, USA |
| *Methylobacterium* sp. #31 | ISO31 | LGP2028 | NRRL-B-68064 | A *Nasturtium* spp. growing in Saint Louis County, Missouri, USA |
| *Methylobacterium* sp #32 | ISO32 | LGP2029 | NRRL B-68065 | A *Salvia officinalis* (sage) growing in Saint Louis County, Missouri, USA |
| *Methylobacterium* sp #33 | IS033 | LGP2030 | NRRL B-68066 | A *Prunus persica* (peach, 'Hale Haven'), growing in Dudley, Missouri, USA |
| *Methylobacterium* sp #34 | ISO34 | LGP2031 | NRRL B-68067 | An *Acer* spp. (maple) growing in Dudley, Missouri, USA |
| *Methylobacterium* sp #35 | ISO35 | LGP2033 | NRRL B-68068 | A *Rosa rugosa* (Japanese rose) growing in Camden, Maine, USA |
| *Methylobacterium* sp #36 | IS036 | LGP2034 | NRRL B-68069 | A *Solidago* sp. (goldenrod) growing in Camden, Maine, USA |
| *Methylobacterium* sp. #37 | ISO37 | NLS0737 | NRRL-B-68074 | A lettuce plant growing in San Luis Obispo, CA |

TABLE 1-continued

| | | | | Methylobacterium sp. strain |
|---|---|---|---|---|
| Deposit Identifier | Isolate No. | LGP NO. | USDA ARS NRRL No.[1] | Strain Source: Obtained from: |
| Methylobacterium sp. #38 | ISO38 | NLS0770 | NRRL-B-68075 | A lettuce plant growing in San Luis Obispo, CA |
| Methylobacterium sp. #39 | ISO39 | NLS5278 | NRRL-B-68186 | An unidentified non-crop plant growing in Durham, North Carolina, USA |
| Methylobacterium sp. #40 | ISO40 | NLS5334 | NRRL-B-68187 | An unidentified non-crop plant growing in Durham, North Carolina, USA |
| Methylobacterium sp. #41 | ISO41 | NLS5480 | NRRL-B-68188 | An unidentified non-crop plant growing in Waxhaw, North Carolina, USA |
| Methylobacterium sp. #42 | ISO42 | NLS5549 | NRRL-B-68189 | An unidentified non-crop plant growing in Waxhaw, North Carolina, USA |

[1]Deposit number for strain deposited with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Illinois 61604 U.S.A. under the terms of the Budapest Treaty on the International Recognition of the Deposit of Microorganisms for the Purposes of Patent Procedure. Subject to 37 CFR §1.808(b), all restrictions imposed by the depositor on the availability to the public of the deposited material will be irrevocably removed upon the granting of any patent from this patent application.

Variants of a *Methylobacterium* isolate listed in Table 1 include isolates obtained therefrom by genetic transformation, mutagenesis and/or insertion of a heterologous sequence. In some embodiments, such variants are identified by the presence of chromosomal genomic DNA with at least 99%, 99.9, 99.8, 99.7, 99.6%, or 99.5% sequence identity to chromosomal genomic DNA of the strain from which it was derived. Variants of NLS0737 or NLS0770 can be identified, for example, by the presence of SEQ ID NO: 31 in the genome of a methane mitigating *Methylobacterium*. Variants of NLS5278, NLS5334, NLS5480, or NLS5549 can be identified, for example, by the presence of SEQ ID NO: 32 in the genome of a methane mitigating *Methylobacterium*.

In certain embodiments of the methods provided herein, the *Methylobacterium* strain or strains used to treat a plant seed and/or a plant part are selected from the group consisting of ISO01 (NRRL B-50929), ISO02 (NRRL B-50930), ISO03 (NRRL B-50931), ISO04 (NRRL B-50932), ISO05 (NRRL B-50933), ISO06 (NRRL B-50934), ISO07 (NRRL B-50935), ISO08 (NRRL B-50936), ISO09 (NRRL B-50937), ISO10 (NRRL B-50938), ISO11 (NRRL B-50939), ISO12 (NRRL B-50940), ISO13 (NRRL B-50941), ISO14 (NRRL B-50942), ISO15 (NRRL B-67339), ISO16 (NRRL B-67340), ISO17 (NRRL B-67341), ISO18 (NRRL B-67741), ISO19 (NRRL B-67742), ISO20 (NRRL B-67743), ISO21 (NRRL B-67892), NLS0770, NLS0737, NLS5278, NLS5334, NLS5480, NLS5549, variants thereof, or any combination thereof. In certain embodiments, one or more of the *Methylobacterium* strains used in the methods can comprise total genomic DNA (chromosomal and plasmid DNA) or average nucleotide identity (ANI) with at least 99%, 99.9, 99.8, 99.7, 99.6%, or 99.5% sequence identity or ANI to total genomic DNA of ISO01 (NRRL B-50929), ISO02 (NRRL B-50930), ISO03 (NRRL B-50931), ISO04 (NRRL B-50932), ISO05 (NRRL B-50933), ISO06 (NRRL B-50934), ISO07 (NRRL B-50935), ISO08 (NRRL B-50936), ISO09 (NRRL B-50937), ISO10 (NRRL B-50938), ISO11 (NRRL B-50939), ISO12 (NRRL B-50940), ISO13 (NRRL B-50941), ISO14 (NRRL B-50942), ISO15 (NRRL B-67339), ISO16 (NRRL B-67340), ISO17 (NRRL B-67341), ISO18 (NRRL B-67741), ISO19 (NRRL B-67742), ISO20 (NRRL B-67743), ISO21 (NRRL B-67892), NLS0770, NLS0737, NLS5278, NLS5334, NLS5480, NLS5549. In certain embodiments, the percent ANI can be determined as disclosed by Konstantinidis et al., 2006. In certain embodiments of the methods provided herein, the *Methylobacterium* strain or strains used to treat a seed and/or a plant part is NLS0737, NLS0770, NLS5278, NLS5334, NLS5480, or NLS5549 which were deposited under the NRRL accession Nos. NRRL-B-68074, NRRL-B-68075, NRRL-B-68186, NRRL-B-68187, NRRL-B-68188, and NRRL-B-68189 respectively.

In certain embodiments of the methods provided herein, plants, plant seeds and/or plant parts are treated with both a *Methylobacterium* strain and at least one additional component. In some embodiments an additional component can be an additional active ingredient, for example, a pesticide or a second biological. In certain embodiments, the pesticide can be an insecticide, a fungicide, an herbicide, a nematicide or other biocide. The second biological could be a strain that improves yield or controls an insect, pest, fungi, weed, or nematode. In some embodiments, a second biological is a second *Methylobacterium* strain.

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In particular embodiments insecticides and nematicides include abamectin, aldicarb, aldoxycarb, bifenthrin, carbofuran, chlorantraniliporle, chlothianidin, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, tioxazafen, spinetoram, spinosad, spirodichlofen, spirotetramat, tefluthrin, thiacloprid, thiamethoxam, and thiodicarb.

Non-limiting examples of useful fungicides include aromatic hydrocarbons, benzimidazoles, benzothiadiazole, carboxamides, carboxylic acid amides, morpholines, phenylamides, phosphonates, quinone outside inhibitors (e.g. strobilurins), thiazolidines, thiophanates, thiophene carboxamides, and triazoles. Particular examples of fungicides include acibenzolar-S-methyl, azoxystrobin, benalaxyl, bixafen, boscalid, carbendazim, cyproconazole, dimethomorph, epoxiconazole, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thifluzamide, thiophanate, tolclofos-methyl, trifloxystrobin, and triticonazole. Non-limiting examples of other biocides, include isothiazolinones, for example 1,2 Benzothiazolin-3-one (BIT), 5-Chloro-2-methyl-4-isothiazolin-3-one (CIT), 2-Methyl-4-isothiazolin-3-one (MIT), octylisothiazolinone (OIT), dichlorooctylisothiazolinone (DCOIT), and butylbenzisothiazolinone (BBIT); 2-Bromo-2-nitro-propane-1,3-diol (Bronopol), 5-bromo-5-nitro-1,3-dioxane (Bronidox), Tris(hydroxymethyl)nitromethane, 2,2-Dibromo-3-nitrilopropionamide (DBNPA), and alkyl dimethyl benzyl ammonium chlorides.

Non-limiting examples of herbicides include ACCase inhibitors, acetanilides, AHAS inhibitors, carotenoid biosynthesis inhibitors, EPSPS inhibitors, glutamine synthetase inhibitors, PPO inhibitors, PS II inhibitors, and synthetic auxins, Particular examples of herbicides include acetochlor, clethodim, dicamba, flumioxazin, fomesafen, glyphosate, glufosinate, mesotrione, quizalofop, saflufenacil, sulcotrione, and 2,4-D.

In some embodiments, the composition or method disclosed herein may comprise a *Methylobacterium* strain and an additional active ingredient selected from the group consisting of clothianidin, ipconazole, imidacloprid, metalaxyl, mefenoxam, tioxazafen, azoxystrobin, thiamethoxam, fluopyram, prothioconazole, pyraclostrobin, and sedaxane.

In some embodiments, the composition or method disclosed herein may comprise an additional active ingredient, which may be a second biological. The second biological could be a biological control agent, other beneficial microorganisms, microbial extracts, plant extracts, yeast extracts, vegetal chitosan, natural products, plant growth activators or plant defense agent. Non-limiting examples of the second biological could include bacteria, fungi, beneficial nematodes, and viruses. In certain embodiments, the second biological can be a *Methylobacterium*. In certain embodiments, the second biological is a *Methylobacterium* listed in Table 1. In certain embodiments, the second biological can be a *Methylobacterium* selected from *M. gregans, M. radiotolerans, M. extorquens, M. populi, M. salsuginis, M. brachiatum*, and *M. komagatae*.

In certain embodiments, the second biological can be a bacterium of the genus *Actinomycetes, Agrobacterium, Arthrobacter, Alcaligenes, Aureobacterium, Azobacter, Azorhizobium, Azospirillum, Azotobacter, Beijerinckia, Bacillus, Brevibacillus, Burkholderia, Chromobacterium, Clostridium, Clavibacter, Comomonas, Corynebacterium, Curtobacterium, Enterobacter, Flavobacterium, Gluconacetobacter, Gluconobacter, Herbaspirillum, Hydrogenophage, Klebsiella, Luteibacter, Lysinibacillus, Mesorhizobium, Methylobacterium, Microbacterium, Ochrobactrum, Paenibacillus, Pantoea, Pasteuria, Phingobacterium, Photorhabdus, Phyllobacterium, Pseudomonas, Rhizobium, Rhodococcus, Bradyrhizobium, Serratia, Sinorhizobium, Sphingomonas, Streptomyces, Stenotrophomonas, Variovorax, Xanthomonas* and *Xenorhadbus*. In particular embodiments the bacteria is selected from the group consisting of *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Chromobacterium suttsuga, Pasteuria penetrans, Pasteuria usage*, and *Pseudomona fluorescens*.

In certain embodiments the second biological can be a fungus of the genus *Acremonium, Alternaria, Ampelomyces, Aspergillus, Aureobasidium, Beauveria, Botryosphaeria, Cladosporium, Cochliobolus, Colletotrichum, Coniothyrium, Embellisia, Epicoccum, Fusarium, Gigaspora, Gliocladium, Glomus, Laccaria, Metarhisium, Muscodor, Nigrospora, Paecilonyces, Paraglomus, Penicillium, Phoma, Pisolithus, Podospora, Rhizopogon, Scleroderma, Trichoderma, Typhula, Ulocladium*, and *Verticilium*. In particular embodiments, the fungus is *Beauveria bassiana, Coniothyrium minitans, Gliocladium vixens, Muscodor albus, Paecilomyces lilacinus*, or *Trichoderma polysporum*.

In certain embodiments, compositions comprise multiple additional biological ingredients, including consortia comprising combinations of any of the above bacterial or fungal genera or species.

In further embodiments the second biological can be a biostimulant, including but not limited to seaweed extract or hummates, plant growth activators or plant defense agents including, but not limited to harpin, *Reynoutria sachalinensis*, jasmonate, lipochitooligosaccharides, and isoflavones.

In further embodiments, the second biological can include, but are not limited to, various *Bacillus* sp., *Pseudomonas* sp., *Coniothyrium* sp., *Pantoea* sp., *Streptomyces* sp., and *Trichoderma* sp. Microbial biopesticides can be a bacterium, fungus, virus, or protozoan. Particularly useful biopesticidal microorganisms include various *Bacillus subtilis, Bacillus thuringiensis, Bacillus pumilis, Pseudomonas syringae, Trichoderma harzianum, Trichoderma virens*, and *Streptomyces lydicus* strains. Other microorganisms that are added can be genetically engineered or wild-type isolates that are available as pure cultures. In certain embodiments, it is anticipated that the second biological can be provided in the composition in the form of a spore.

Fields, plants or harvested plant parts having mitigated methane in comparison to a control field, plant, or plant part are provided, as are methods for obtaining and using such plants and plant parts. In certain embodiments, the content of at least mitigated methane is decreased by at least about 0.1%, 5%, 1%, or 2% to about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%.

Additionally, disclosed are recombinant constructs for expression of an sMMO component protein, or modification thereof, wherein said construct comprises a genetic element encoding any one or more of SEQ ID NO: 1-8 or a modification thereof.

Further, the recombinant constructs described herein can have the genetic element further comprise a genetic element having a sequence any one of SEQ ID NOS: 9-16, or a modification thereof.

The recombinant constructs disclosed above, can also have the genetic element encodes SEQ ID No. 1-4 or SEQ ID No. 5-8.

DEPOSIT INFORMATION

Samples of the following *Methylobacterium* sp. strains have been deposited with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Illinois 61604 U.S.A. under the terms of the Budapest Treaty on the International Recognition of the Deposit of Microorganisms for the Purposes of Patent Procedure. *Methylobacterium* sp. NRRL B-50929, NRRL B-50930, NRRL B-50931, NRRL B-50932, NRRL B-50933, NRRL B-50934, NRRL B-50935, NRRL B-50936, NRRL B-50937, NRRL B-50938, NRRL B-50939, NRRL B-50940, NRRL B-50941 and NRRL B-50942 were deposited with NRRL on Mar. 12, 2014. *Methylobacterium* sp. NRRL B-67339, NRRL B-67340, and NRRL B-67341 were deposited with NRRL on Nov. 18, 2016. *Methylobacterium* sp. NRRL B-67741, NRRL B-67742, and NRRL B-67743 were deposited with NRRL on Dec. 20, 2018. *Methylobacterium* sp. NRRL B-67892 was deposited with NRRL on Nov. 26, 2019. *Methylobacterium* sp. NRRL B-67925, NRRL B-67926 and NRRL B-67927 were deposited with NRRL on Feb. 21, 2020. *Methylobacterium* sp. NRRL B-67929 was deposited with NRRL on Mar. 3, 2020. *Methylobacterium* sp. NRRL B-68032, NRRL B-68033 and NRRL B-68034 were deposited with NRRL on May 20, 2021. *Methylobacterium* sp. NRRL B-68064, NRRL B-68065, NRRL B-68066, NRRL B-68067, NRRL B-68068, and NRRL B-68069 were deposited with NRRL on Sep. 9, 2021. NRRL B-68074 and NRRL B-68075 were deposited with NRRL on Oct. 6, 2021. NRRL B-68186, NRRL B-68187, NRRL B-68188 and NRRL B-68189 were deposited with NRRL on Aug. 3, 2022.

Subject to 37 CFR § 1.808(b), all restrictions imposed by the depositor on the availability to the public of the deposited material will be irrevocably removed upon the granting of any patent from this patent application.

EXAMPLES

The following examples are given for purely illustrative and non-limiting purposes of the present invention.

Example 1 *Methylobacterium* Inoculation Effect on Promotion of Early Rice Growth

*Methylobacterium* isolates were tested for their ability to enhance early growth of rice seedlings. A randomized complete block design was used, with 12 treatments in each run; 10 unique *Methylobacterium* isolates, a *Methylobacterium* positive control, LGP2018, that demonstrated consistent root growth promotion of rice seedlings during assay development and increased yield levels in corn field trials (WO2020117690). The untreated control sample (UTC) was *Methylobacterium* growth medium applied in the same amount as used for the *Methylobacterium* isolates. Each treatment level had an n of 10. All 10 blocks were grown in the same growth chamber, and on the same shelf.

Procedure:

Media:
0.5× Murashige and Skoog MS agar plates with 0.5% sucrose

Pre-Planting:
Rice seeds were de-husked. Average 100 seed count is 2018 mg with approximately 21 g of husked rice per run.

Planting:
Seeds were sterilized in ~3% sodium hypochlorite+0.05% Tween 20.
Seeds were washed to remove bleach solution and placed on a sterile plate lid to begin drying.
Seeds were plated using a randomized complete block design with each complete block having similarly sized seeds.
Using sterile techniques 8 sterile seeds were evenly spaced in a horizontal line (~40% above the bottom of the plate, using a pre-marked lid as a guide). Seeds were placed with the embryo toward the bottom of the plate and gently pushed into media.

Inoculation:
Each *Methylobacterium* isolate or the culture medium control was applied as an 80 uL streak to the bottom portion of the plate (one isolate per plate) and spread by gently tilting the plate back and forth. A target concentration of $1 \times 10^6$ CFU per seed was applied.
Plates were allowed to dry for at least one hour and placed in a randomized layout in a Percival growth chamber set to 25° C. and 16 hour days.
Seeds were allowed to grow undisturbed for 8 days.

Harvest:
At 8 days after plating the plates were removed from the growth chambers, and the plants (approximately V2 stage) were measured as follows.
Plants that were not impeded from growing normally (by physical surroundings unrelated to presence of *Methylobacterium*) were removed from plates, and the number of seedlings for that plate recorded.
Seedlings were scanned using WinRhizo and the images analyzed to determine root length for each plant.
The results of this experiment are shown below in Table 2.

TABLE 2

| Experiment Number | Treatment ID | Treatment | Absolute Root Length (cm) | Normalized Root Length |
|---|---|---|---|---|
| 264PB | 264PB LGP2018 | LGP2018 | 18.82978 | 100 |
| 264PB | 264PB Strain 1 | LGP2025 | 17.39133 | 73.325898 |
| 264PB | 264PB Strain 2 | LGP2073 | 17.19 | 69.59247 |
| 264PB | 264PB Strain 3 | LGP2047 | 16.37316 | 54.44538 |
| 264PB | 264PB Strain 4 | LGP2045 | 15.96066 | 46.796074 |
| 264PB | 264PB Strain 5 | LGP2151 | 15.39851 | 36.371618 |
| 264PB | 264PB Strain 6 | LGP2103 | 15.04489 | 29.814374 |
| 264PB | 264PB Strain 7 | LGP2125 | 14.84019 | 26.018352 |
| 264PB | 264PB Strain 8 | LGP2017 | 14.54892 | 20.61718 |
| 264PB | 264PB Strain 9 | LGP2120 | 13.84252 | 7.517937 |
| 264PB | 264PB Strain 10 | LGP2124 | 13.18279 | −4.715877 |
| 265PB | 265PB Strain 1 | LGP2071 | 14.117796 | 100.010863 |
| 265PB | 265PB LGP2018 | LGP2018 | 14.117132 | 100 |
| 265PB | 265PB Strain 2 | LGP2061 | 12.535499 | 74.124179 |
| 265PB | 265PB Strain 3 | LGP2107 | 11.83976 | 62.741755 |
| 265PB | 265PB Strain 4 | LGP2065 | 9.992807 | 32.52525 |
| 265PB | 265PB Strain 5 | LGP2051 | 9.743358 | 28.444232 |
| 265PB | 265PB Strain 6 | LGP2054 | 8.960485 | 15.636268 |
| 265PB | 265PB Strain 7 | LGP2092 | 8.856461 | 13.934427 |
| 265PB | 265PB Strain 8 | LGP2079 | 8.610079 | 9.903568 |
| 265PB | 265PB Strain 9 | LGP2052 | 7.916505 | −1.443435 |
| 266PB | 266PB Strain 1 | LGP2059 | 15.569966 | 123.451522 |
| 266PB | 266PB Strain 2 | LGP2016 | 14.587924 | 108.443799 |
| 266PB | 266PB LGP2018 | LGP2018 | 14.035398 | 100 |
| 266PB | 266PB Strain 3 | LGP2158 | 13.207394 | 87.346316 |
| 266PB | 266PB Strain 4 | LGP2066 | 12.900975 | 82.663567 |
| 266PB | 266PB Strain 5 | LGP2141 | 11.897894 | 67.334339 |
| 266PB | 266PB Strain 6 | LGP2078 | 10.298694 | 42.8951 |
| 266PB | 266PB Strain 7 | LGP2050 | 10.041706 | 38.967777 |
| 266PB | 266PB Strain 8 | LGP2080 | 9.462625 | 30.118161 |
| 266PB | 266PB Strain 9 | LGP2048 | 9.284123 | 27.390276 |
| 266PB | 266PB Strain 10 | LGP2053 | 7.207347 | −4.347354 |
| 267PB | 267PB Strain 1 | LGP2046 | 14.419073 | 137.78678 |
| 267PB | 267PB LGP2018 | LGP2018 | 12.303465 | 100 |
| 267PB | 267PB Strain 2 | LGP2024 | 11.846345 | 91.835407 |
| 267PB | 267PB Strain 3 | LGP2148 | 10.620679 | 69.94383 |
| 267PB | 267PB Strain 4 | LGP2144 | 9.415631 | 48.420528 |
| 267PB | 267PB Strain 5 | LGP2150 | 9.382432 | 47.827557 |
| 267PB | 267PB Strain 6 | LGP2110 | 9.298016 | 46.319801 |
| 267PB | 267PB Strain 7 | LGP2176 | 8.103827 | 24.990443 |
| 267PB | 267PB Strain 8 | LGP2153 | 7.128328 | 7.567103 |
| 267PB | 267PB Strain 9 | LGP2082 | 6.373293 | −5.91855 |
| 268PB | 268PB Strain 1 | LGP2021 | 15.569966 | 123.451522 |

TABLE 2-continued

| Experiment Number | Treatment ID | Treatment | Absolute Root Length (cm) | Normalized Root Length |
|---|---|---|---|---|
| 268PB | 268PB Strain 2 | LGP2040 | 14.587924 | 108.443799 |
| 268PB | 268PB LGP2018 | LGP2018 | 14.035398 | 100 |
| 268PB | 268PB Strain 3 | LGP2138 | 13.207394 | 87.346316 |
| 268PB | 268PB Strain 4 | LGP2095 | 12.900975 | 82.663567 |
| 268PB | 268PB Strain 5 | LGP2130 | 11.897894 | 67.334339 |
| 268PB | 268PB Strain 6 | LGP2099 | 10.298694 | 42.8951 |
| 268PB | 268PB Strain 7 | LGP2077 | 10.041706 | 38.967777 |
| 268PB | 268PB Strain 8 | LGP2102 | 9.462625 | 30.118161 |
| 268PB | 268PB Strain 9 | LGP2072 | 9.284123 | 27.390276 |
| 268PB | 268PB Strain 10 | LGP2081 | 7.207347 | −4.347354 |
| 269PB | 269PB LGP2018 | LGP2018 | 16.079324 | 100 |
| 269PB | 269PB Strain 1 | LGP2094 | 15.70514 | 95.501874 |
| 269PB | 269PB Strain 2 | LGP2101 | 15.386634 | 91.673054 |
| 269PB | 269PB Strain 3 | LGP2090 | 14.624067 | 82.506105 |
| 269PB | 269PB Strain 4 | LGP2093 | 12.998755 | 62.967937 |
| 269PB | 269PB Strain 5 | LGP2084 | 12.830224 | 60.942001 |
| 269PB | 269PB Strain 6 | LGP2114 | 12.516872 | 57.175138 |
| 269PB | 269PB Strain 7 | LGP2100 | 11.343389 | 43.068489 |
| 269PB | 269PB Strain 8 | LGP2085 | 9.828333 | 24.855728 |
| 269PB | 269PB Strain 9 | LGP2075 | 7.587342 | −2.08362 |
| 269PB | 269PB Strain 10 | LGP2083 | 7.50976 | −3.016248 |
| 270PB | 270PB Strain 1 | LGP2029 | 14.570904 | 104.017951 |
| 270PB | 270PB LGP2018 | LGP2018 | 14.31934 | 100 |
| 270PB | 270PB Strain 2 | LGP2135 | 13.363759 | 84.737607 |
| 270PB | 270PB Strain 3 | LGP2129 | 12.594344 | 72.448632 |
| 270PB | 270PB Strain 4 | LGP2143 | 10.608781 | 40.735534 |
| 270PB | 270PB Strain 5 | LGP2137 | 10.04973 | 31.806444 |
| 270PB | 270PB Strain 6 | LGP2128 | 9.970479 | 30.540667 |
| 270PB | 270PB Strain 7 | LGP2123 | 9.933589 | 29.951459 |
| 270PB | 270PB Strain 8 | LGP2126 | 9.635704 | 25.193695 |
| 270PB | 270PB Strain 9 | LGP2136 | 9.506136 | 23.124249 |
| 270PB | 270PB Strain 10 | LGP2121 | 7.872883 | −2.961817 |
| 271PB | 271PB LGP2018 | LGP2018 | 18.545695 | 100 |
| 271PB | 271PB Strain 1 | LGP2069 | 16.856945 | 83.10707 |
| 271PB | 271PB Strain 2 | LGP2027 | 15.948911 | 74.02381 |
| 271PB | 271PB Strain 3 | LGP2056 | 14.750148 | 62.03233 |
| 271PB | 271PB Strain 4 | LGP2096 | 14.330543 | 57.83493 |
| 271PB | 271PB Strain 5 | LGP2060 | 13.874818 | 53.27622 |
| 271PB | 271PB Strain 6 | LGP2097 | 13.443795 | 48.9646 |
| 271PB | 271PB Strain 7 | LGP2067 | 13.24211 | 46.9471 |
| 271PB | 271PB Strain 8 | LGP2055 | 12.770669 | 42.23118 |
| 271PB | 271PB Strain 9 | LGP2086 | 12.549608 | 40.01986 |
| 271PB | 271PB Strain 10 | LGP2057 | 11.572393 | 30.24456 |
| 273PB | 273PB LGP2018 | LGP2018 | 13.216513 | 100 |
| 273PB | 273PB Strain 1 | LGP2028 | 11.289892 | 71.38989 |
| 273PB | 273PB Strain 2 | LGP2098 | 10.957287 | 66.45074 |
| 273PB | 273PB Strain 3 | LGP2116 | 10.552009 | 60.43241 |
| 273PB | 273PB Strain 4 | LGP2131 | 10.492209 | 59.54438 |
| 273PB | 273PB Strain 5 | LGP2117 | 9.92343 | 51.09808 |
| 273PB | 273PB Strain 6 | LGP2133 | 9.207299 | 40.46361 |
| 273PB | 273PB Strain 7 | LGP2140 | 9.188468 | 40.18397 |
| 273PB | 273PB Strain 8 | LGP2134 | 8.651127 | 32.20451 |
| 273PB | 273PB Strain 9 | LGP2109 | 7.244746 | 11.31992 |
| 273PB | 273PB Strain 10 | LGP2111 | 5.404409 | −16.0089 |
| 274PB | 274PB Strain 1 | LGP2033 | 17.459903 | 136.108331 |
| 274PB | 274PB Strain 2 | LGP2118 | 15.623786 | 106.167536 |
| 274PB | 274PB LGP2018 | LGP2018 | 15.245562 | 100 |
| 274PB | 274PB Strain 3 | LGP2145 | 14.631981 | 89.994584 |
| 274PB | 274PB Strain 4 | LGP2032 | 14.299443 | 84.572029 |
| 274PB | 274PB Strain 5 | LGP2152 | 13.881329 | 77.754029 |
| 274PB | 274PB Strain 6 | LGP2147 | 13.409769 | 70.064484 |
| 274PB | 274PB Strain 7 | LGP2157 | 11.306689 | 35.770445 |
| 274PB | 274PB Strain 8 | LGP2142 | 10.1196 | 16.413079 |
| 274PB | 274PB Strain 9 | LGP2159 | 9.361136 | 4.045128 |
| 274PB | 274PB Strain 10 | LGP2154 | 8.943802 | −2.760155 |
| 275PB | 275PB LGP2018 | LGP2018 | 18.826053 | 100 |
| 275PB | 275PB Strain 1 | LGP 2022 | 17.00802 | 80.576456 |
| 275PB | 275PB Strain 2 | LGP2023 | 16.310993 | 73.129541 |
| 275PB | 275PB Strain 3 | LGP2160 | 15.87016 | 68.41976 |
| 275PB | 275PB Strain 4 | LGP2163 | 15.337422 | 62.728087 |
| 275PB | 275PB Strain 5 | LGP2167 | 15.162438 | 60.858589 |
| 275PB | 275PB Strain 6 | LGP2166 | 14.298438 | 51.627764 |
| 275PB | 275PB Strain 7 | LGP2161 | 13.02194 | 37.989883 |
| 275PB | 275PB Strain 8 | LGP2162 | 11.85523 | 25.52496 |
| 275PB | 275PB Strain 9 | LGP2168 | 10.190812 | 7.742619 |
| 277PB | 277PB LGP2018 | LGP2018 | 15.854562 | 100 |

TABLE 2-continued

| Experiment Number | Treatment ID | Treatment | Absolute Root Length (cm) | Normalized Root Length |
|---|---|---|---|---|
| 277PB | 277PB Strain 1 | LGP2062 | 14.420103 | 81.45296 |
| 277PB | 277PB Strain 2 | LGP2185 | 14.124727 | 77.63385 |
| 277PB | 277PB Strain 3 | LGP2063 | 13.598758 | 70.83327 |
| 277PB | 277PB Strain 4 | LGP2074 | 12.56993 | 57.53088 |
| 277PB | 277PB Strain 5 | LGP2058 | 12.237293 | 53.23002 |
| 277PB | 277PB Strain 6 | LGP2064 | 11.790611 | 47.45458 |
| 277PB | 277PB Strain 7 | LGP2091 | 11.598483 | 44.97043 |
| 277PB | 277PB Strain 8 | LGP2186 | 10.193847 | 26.809 |
| 277PB | 277PB Strain 9 | LGP2105 | 10.166668 | 26.45758 |
| 277PB | 277PB Strain 10 | LGP2187 | 10.018778 | 24.54541 |
| 282PB | 282PB LGP2018 | LGP2018 | 17.115992 | 100 |
| 282PB | 282PB Strain 1 | LGP2087 | 15.150588 | 77.27183 |
| 282PB | 282PB Strain 2 | LGP2108 | 14.929319 | 74.71305 |
| 282PB | 282PB Strain 3 | LGP2076 | 14.913514 | 74.53028 |
| 282PB | 282PB Strain 4 | LGP2106 | 13.131888 | 53.92734 |
| 282PB | 282PB Strain 5 | LGP2113 | 12.547632 | 47.17093 |
| 282PB | 282PB Strain 6 | LGP2049 | 12.529399 | 46.96009 |
| 282PB | 282PB Strain 7 | LGP2068 | 12.507406 | 46.70576 |
| 282PB | 282PB Strain 8 | LGP2149 | 12.28271 | 44.10735 |
| 282PB | 282PB Strain 9 | LGP2005 | 11.888991 | 39.55433 |
| 282PB | 282PB Strain 10 | LGP2006 | 10.285192 | 21.00781 |
| 283PB | 283PB Strain 1 | LGP2182 | 14.59702 | 103.904114 |
| 283PB | 283PB LGP2018 | LGP2018 | 14.364828 | 100 |
| 283PB | 283PB Strain 2 | LGP2034 | 13.842152 | 91.211673 |
| 283PB | 283PB Strain 3 | LGP2146 | 12.351052 | 66.14017 |
| 283PB | 283PB Strain 4 | LGP2181 | 12.117376 | 62.211111 |
| 283PB | 283PB Strain 5 | LGP2089 | 11.13865 | 45.754717 |
| 283PB | 283PB Strain 6 | LGP2156 | 10.858914 | 41.051207 |
| 283PB | 283PB Strain 7 | LGP2170 | 10.110786 | 28.472101 |
| 283PB | 283PB Strain 8 | LGP2155 | 9.582397 | 19.587708 |
| 283PB | 283PB Strain 9 | LGP2127 | 8.857205 | 7.394253 |
| 283PB | 283PB Strain 10 | LGP2139 | 8.755959 | 5.691884 |
| 285PB | 285PB LGP2018 | LGP2018 | 12.031742 | 100 |
| 285PB | 285PB Strain 1 | LGP2173 | 11.21333 | 84.0138457 |
| 285PB | 285PB Strain 2 | LGP2172 | 10.228408 | 64.7752232 |
| 285PB | 285PB Strain 3 | LGP2164 | 9.964949 | 59.6290516 |
| 285PB | 285PB Strain 4 | LGP2165 | 9.033842 | 41.4416163 |
| 285PB | 285PB Strain 5 | LGP2008 | 7.982016 | 20.8961413 |
| 285PB | 285PB Strain 6 | LGP2112 | 7.609441 | 13.6186008 |
| 285PB | 285PB Strain 7 | LGP2169 | 7.485808 | 11.2036581 |
| 285PB | 285PB Strain 8 | LGP2044 | 7.402148 | 9.5695127 |
| 285PB | 285PB Strain 9 | LGP 2011 | 6.922695 | 0.2042973 |
| 285PB | 285PB Strain 10 | LGP2171 | 5.864521 | −20.4651746 |
| 286PB | 286PB Strain 1 | LGP2001 | 18.47052 | 102.4019 |
| 286PB | 286PB LGP2018 | LGP2018 | 18.29094 | 100 |
| 286PB | 286PB Strain 2 | LGP2012 | 17.23022 | 85.81258 |
| 286PB | 286PB Strain 3 | LGP2000 | 17.06282 | 83.57344 |
| 286PB | 286PB Strain 4 | LGP2015 | 16.97065 | 82.34073 |
| 286PB | 286PB Strain 5 | LGP2007 | 15.82329 | 66.99432 |
| 286PB | 286PB Strain 6 | LGP2003 | 14.07074 | 43.5534 |
| 286PB | 286PB Strain 7 | LGP2010 | 14.04739 | 43.24119 |
| 286PB | 286PB Strain 8 | LGP2013 | 13.72635 | 38.9471 |
| 286PB | 286PB Strain 9 | LGP2004 | 12.51197 | 22.7044 |
| 288PB | 288PB Strain 1 | LGP2031 | 11.73032 | 115.04974 |
| 288PB | 288PB LGP2018 | LGP2018 | 10.961572 | 100 |
| 288PB | 288PB Strain 2 | LGP2030 | 10.823393 | 97.29486 |
| 288PB | 288PB Strain 3 | LGP2184 | 10.428576 | 89.56555 |
| 288PB | 288PB Strain 4 | LGP2188 | 10.060309 | 82.35601 |
| 288PB | 288PB Strain 5 | LGP2132 | 10.004185 | 81.25727 |
| 288PB | 288PB Strain 6 | LGP2179 | 9.603427 | 73.41165 |
| 288PB | 288PB Strain 7 | LGP2183 | 9.371095 | 68.86329 |
| 288PB | 288PB Strain 8 | LGP2122 | 8.820766 | 58.08953 |
| 288PB | 288PB Strain 9 | LGP2009 | 7.664263 | 35.44871 |
| 288PB | 288PB Strain 10 | LGP2088 | 6.600541 | 14.62428 |
| 289PB | 289PB Strain 1 | LGP2002 | 16.64733 | 117.25169 |
| 289PB | 289PB LGP2018 | LGP2018 | 15.73919 | 100 |
| 289PB | 289PB Strain 2 | LGP2174 | 14.52193 | 76.87615 |
| 289PB | 289PB Strain 3 | LGP2178 | 14.47025 | 75.89433 |

TABLE 2-continued

| Experiment Number | Treatment ID | Treatment | Absolute Root Length (cm) | Normalized Root Length |
|---|---|---|---|---|
| 289PB | 289PB Strain 4 | LGP2119 | 14.41787 | 74.89923 |
| 289PB | 289PB Strain 5 | LGP2070 | 14.39551 | 74.47451 |
| 289PB | 289PB Strain 6 | LGP2104 | 14.2175 | 71.09291 |
| 289PB | 289PB Strain 7 | LGP2175 | 13.17078 | 51.20856 |
| 289PB | 289PB Strain 8 | LGP2115 | 13.15135 | 50.83953 |
| 289PB | 289PB Strain 9 | LGP2177 | 13.0369 | 48.66526 |
| 289PB | 289PB Strain 10 | LGP2180 | 13.00762 | 48.10911 |

Forty-eight *Methylobacterium* strains were selected for gene correlation analysis from the 176 strains tested, including 15 non-hits and 33 hits. The strains were selected from those having the highest and lowest normalized root scores, excluding any isolates that had any signs of any type of microbial contamination. The normalized score standardized each isolate's mean root length value to the UTC (a value of 0) and the positive control, LGP2018 (a value of 100).

Genomes of the selected isolates were assembled and putative genes identified. The genes were assigned a putative function by sequence analysis to databases of known genes and gene signatures. A pan-genome for *Methylobacterium* was constructed as described by Page et al. (Roary: rapid large-scale prokaryote pan genome analysis, Bioinformatics (2015) 31:3691-3693) except that genome sequences from greater than 1000 different species of *Methylobacterium*

(Rapid scoring of genes in microbial pan-genome-wide association studies with Scoary, *Genome Biology* (2016) 17:238).

The steps in the process were as follows. Correlated genetic elements were collapsed so that genes that are typically inherited together, for example genes on the same plasmid, were combined into a single unit. Each genetic element in the pan-genome received a null hypothesis of no association to the trait. A Fisher's exact test was performed on each genetic element with the assumption that all strains had a random and independently distributed probability for exhibiting each state, i.e. presence or absence of the genetic element. To control spurious associations due to population structure, the pairwise comparisons algorithm was applied using a phylogenetic tree of the *Methylobacterium* genus, constructed using the same genome sequences described above. Empirical p-value was computed using label-switching permutations, i.e. the test statistic was generated over random permutations of the phenotype data. The genetic elements that were significantly positively correlated with enhancing rice seedling root growth were identified based on p value using a threshold for statistical significance of p less than or equal to 0.05. Sensitivity and specificity cutoffs were also employed based on the number of hits and non-hits a gene was present in.

Gene elements that were positively correlated with *Methylobacterium* enhancement of growth in rice seedlings are shown in Table 3 below.

TABLE 3

| Gene name | Consensus Protein SEQ ID NO: | Representative protein sequences | Annotation | Sensitivity | Specificity | p-value |
|---|---|---|---|---|---|---|
| group_4403 | 17 | SEQ ID NO: 24 | hypothetical protein | 60.61 | 80.00 | 0.003 |
| group_9931 | 18 | SEQ ID NO: 25 | hypothetical protein | 57.58 | 86.67 | 0.025 |
| group_7199 | 19 | SEQ ID NO: 26 | hypothetical protein | 66.67 | 86.67 | 0.030 |
| recD2_2 | 20 | SEQ ID NO: 27 | ATP-dependent RecD-like DNA helicase | 45.45 | 93.33 | 0.035 |
| pinR | 21 | SEQ ID NO: 28 | Putative DNA-invertase from lambdoid prophage Rac | 69.70 | 80.00 | 0.039 |
| group_2780 | 22 | SEQ ID NO: 29 | hypothetical protein | 33.33 | 100.00 | 0.055 |
| group_5546 | 23 | SEQ ID NO: 30 | hypothetical protein | 60.61 | 80.00 | 0.057 | were assembled and used to construct the pan-genome as opposed to the single *Salmonella* species described by Page et al.

The genomes of strains identified as enhancing rice seedling growth, "hits", and strains identified as "non-hits", were compared to determine the presence or absence in each strain of each genetic element in the pan-genome. For this analysis, translated genes were clustered across strains using BLASTP with a sequence identity of at least 50% to identify homologous genetic elements across genomes. These results were used to determine which genetic elements are the same or different across strains, leading to a score for each genetic element as present or absent in a given strain. The presence/absence scores were used in a correlation analysis to identify genetic elements that correlate positively with enhancing rice seedling growth as described by Brynildsrud et al.

*Methylobacterium* consensus protein sequences for the above identified genes that positively correlate with enhanced growth or rice seedlings are provided as SEQ ID NO: 17 through SEQ ID NO: 23 below. Consensus sequences are generated by aligning the encoded protein sequences from all isolates from a comprehensive database of *Methylobacterium* genome sequences from public and internal databases. EMBOSS cons was used to generate consensus sequences from the multiple sequence alignment. Where no consensus was found at a position an 'x' character is used. An upper case letter for an amino acid residue indicates that most of the sequences have that amino acid at that position. In the consensus sequences, X can be any amino acid residue or can be absent.

SEQ ID NO: 17
xxxxxxxxxxxxxxxxxxxxxxxxxxxxxxxxxxxxxxxxxxxxxxxxxxxxMPTxLPxxxx xxxxRxxPVRRLSWPDTARFLILVARVRLLDxxxxxxxxxxxxxxxxxxxxxxxxxxxxxxLRLH AxxxxxxxxxxxxVxRxGSxxAGDxLLxLMRRWLAxHEAIxALLPGVPEPxHVAQVxxxxxxxx xxxxxxxxxxxxxxxxRAILQxxxxxxxxxxVPxSRxxxxxPxxxxxxxxxxxxxxxxxxxxxxxxxxxx xxxxx SEQ ID NO: 18
xxxxxxxMxxPLRRTVQVxEDGRMNLPADMRRVLGLTGAGRVILTQDEDGIxITTaEQA LKRVRSLAAPFxRGxGSVVDEFIAERRADAAREDxExxxxxxxxxxxxxxxxxxxxxxxxxxx xxxxxxxxxxxxxxxxxxxxxxxxxxxxxxx SEQ ID NO: 19
MxxxxxxxxxxxxxxxxxxxxxxxxxxxxxPQSYALQILAIAxAMSVLGLGGVWIASRIYDRNTR RLEAxxxxRRGDxxxxxxxxxxxxxxxxxxxxxxxxxxx SEQ ID NO: 20
xxxxxxxDTLExxxxxxxxxxxxxxxxxxRxxxxxxLACTVxDHxSIAxxQNxVPIIRDIxLxNxxDxDL ADVxLxIxAxPxLxRPLTLxxRIxAGxxxxxIDxPDLRIDxAILxxxxxxAGxxESxxxxxVTLxLxxS xxxxxxxxxExARExxDLRLLPPSHWGGxxAAPELLAAFVRPNDPAVDxILRxAAxILxRAx RxTAxxDGYxSGRKARAWEMAEAIxAxxxxxxAMAxxxxxxxxxxxxxxRIxxxxxxxYVLPPASFE RSGQKVRxPxxIVERRLxTCLDLTLLWAACxEQAGLNPLLVLTxxHAxLGLWLxDExxx xxxxDDxQxLRKRRDLQExxxxxxxxxxxxxLILIETTILTxxxxxxxxxxDPPxxFxxAxxxGAxxIDx DAxAxLEMxLDLRRxRxxGIxPLDxGExxxxxxxxxAPxxxxxxxxxLxxxQxLxxxxxxxxxxAPPSF xEDxxxxxxIDxxxxxxxPxxRLExWKxRLLDLTLRNKLLNFKPGKGSLTLDCxEPGAxEDxLx AGxxFRLxxRPxxxxxDxxxxxxxxxxxxxxxxxxxxxxxxxxxxxxAxxxRxEIxxxxxxxxxxxxxxxxxxxxE LExRLxDLFRLARxxFEEGGANVLFLAxGFLTWTRxxGxxxxxRAPLLLVPxALxRASVR AGFRLxxHDEExRLNPTLLEMLRQDFxLxMPDxxxxxLPxDxSGIDVExIWRIVRTHIRDLK GWEVxxEVVLSAFSFTKFLMWKDLxERxDLLKRSPVVRHLLDTPKAYGDGxxxTxFP xPxRLDxEHPPxxIFxxxxxxPLxADSSQLSAILAAASGKDFVLFGPPGTGKSxxxxxxxxxxQT IxNMIAQCLAxxGRTVLFVSQKSAALEVVxxRRRLxxVGLGxxCLEVHAxKAQKTxVIx QLREAWxxRxxxxxxxxWDxAxxDLxxxRExLNGVVxSLHxxRxNGLSAHxAxGRVIAxxxx GxxxxLxLxWPxxxxxxxxxxxxxSLxxxxxxRAxCxELxxxxxxLxxxVGxIxDHPLRGIxAxxWSPL WRxEMxxAIxxLxRTLxxxxxxSGQxxAEAMGLxxLxxTYxGxxRxLxxLxxxxLxRxEARxGLx FLxxGxxxLRQAVxARxxxQxxxARLxxRLxxxYxxPxVxxxDLxxLLAEWxxAKxSNFxLRG xRLxRVxxxLxPFAQGxxPxDIGPDLxxLxEIxxxxxxxxxxxxxxxxxxxxxVxExxxAxLGxxxPxx xxWSDPxxPAxxFxAxMAWAxRLxxVIxxMxPLxxxGxDxVRxxLxxxxxxxLDxExxxLxxxxxxx xxxxxGGxLAxAxxxxFxxxRxxAVKAIExLGRxxxxxxxxxxLAGRAxPDxxxxPVxxExxxxxxxxx xxxxxxxxxxxxxxxxxxxxxxxxxxxxxxxxxxxxxxxxxxxxxxxxxxxxxxxxxxxxxxxxx xxxxxxxxxxxxxxxxxxxxxxxxxxxxxxxxxxxxxxxxxDxWVxxTLAVAxRWxxxLxxxKAQxWxA WQxAAxxAxKAGLxPLVxAIExGxIxxDxxxxAFExAYARWWIDxxxTDDxxLRxxxxxxFMx QRHEEAIRxFxxADSRLSxLAxxxVRARxxxxxxxxIGGGVPxxxxxxxxAxAFGxDPEWGTLAx EIxxxxxxTKRxRHMPLRQLFxRMPNALTRLxxxTPCLMMSPLSIAQYxPxExKPFDIVIFDE ASQIAPWDAIGAIARGRQVVIVGDPEQLPPTNVGDRGVDEIxxxxxDGxDVADQESILDE CLAANLPQRxLxxxxxxWHYRSRHESLIAFSNxHYYxGxLVTFPSPVTDDxRAVRLxxVxD GLYERGxxRVNRPEARALVAEVVxRLxDPxxxxxxxxxxAFAxExRSLGIVTENGEQQRLIE -continued

```
NLLDxERRxxxxPELExFFDxxxWxEPVFVKNLExVQGDERDAILFSVAxGPxxDxTGRxx xxISSLNREGGHxxxRRLNVAITRARRELVVFASMRxDQVDLGRxxARGVRDFKHFLxF AExxGAxALxxAxAPTGGDIESPFExAVMAxxxxxxxxxALxARGWxIxxQVGVSxFRIDLGI VHPDAPGRYLAGVECDGATYxxxHxAATARDRDRLRExVLTDLGWRIxRVWSTDWW xDxQGALxRLDxxLRxDLDADRAKxxxxxxxxxxxxxxxxxxxxxxxxxxxxxxxxxxxxxxxx xxxxxxxxxxxxxxPxxxxxxxxxxxxxPxxxxxxxQxxxxPxxxxxxxxxxxxxxxxxxYxxADLSxxGxxxD xxRFHDxxYxxxLAAMxAxVVxxEGPVFxDILxxRLxRAHGxxRITxxLRQxxLxxVDPxxxx TxExxRIVLWPxGxxPxxxxxxFRPAxxxxxxxxxxRAxxxDxPLxELxGLARxLxxxxxxxxxxx MAxRLxxxxxxxxxxGLxRMxxAxxxxxxxxxxxxxxxxxxxxxxxxxxxxxxRARFAEAxAxLxAR EXxxxxxxxxxxxxxxxxxxxxxxxxxxxxxxxxxxxxxxxxxxxxxxxxxxxxxxxxxxxxxxxxxx xxxxxxxxxx
```

```
                                                        SEQ ID NO: 21
xxxxxxxxxxxxxxxxxxxxxxxxxxxxxxxxxxxxxxxxxxxxxxxxxxxxxxxxxxxxxxxxxx xxxxxxxxxxMQTILYARVSTADQTIAHQRxQAEAAGFKIxDxVVADEGVSGVSTxLxDRP QGRRLFDxxMLRRGDVLxxxxxxxxVVRWVDRLGRNYAxxxxxxxxxxxxxxxxxxxxxxxxxx xxxxxxxxxxxxDVTETIREFMRxxxxxxxxRGVIVRTVINNxxxxxxxxxxMTFDGATTDPMQxA VRDALxxxIGFMAATAQAQAEATxKEAQKAGIEHAKxRxxExDxxAYRGRKPSYTREQ xxxDxVRxxLxQGxxxVSAIAKATGLSRQxTVYRIRDNPAEAEAALARxxxxxxxxxxxxxxx WAAxxxxxxxxxxxxxxxxxxxxxxxxx
```

```
                                                        SEQ ID NO: 22
MxxxxxxxxxxxxxxxxxxxxYDDxxxADAAAGEERDAIMRALAEDMxEASxxxxRxxxxxGxF VRAERPADLxxxxxxxxxxxxxxxxxxxxxxxxxxxxxxxxxxxxxxxxxxxxxxxxxxxxxxxRAL GRxxxxxDRRxxQxxxxxxxxxxxxxxxxRxASxxxxxxxxxxxxxxxxxxxxxxxxxxxxxxxxxx
```

```
                                                        SEQ ID NO: 23
xxxxxxxxxxxxxxxxxxMPVxxGIGIGRGDPLRPAVTRTxRFSGPEGFHxxPGALWLAAAAP
```

```
LLATxLLLLxxRLAA
```

Representative amino acid sequences for proteins correlated with enhancing growth of rice seedlings from specific *Methylobacterium* strains are provided below as SEQ ID NO: 24 through SEQ ID NO: 30. The strain from which a representative sequence was obtained is referenced below.

LGP2022

```
                                                        SEQ ID NO: 24
MPTAIPIRPAPERCLSWPDTARLLILVARVRILDLEMHTVVRHGSGFADDRLLHLMR

RWLAQHEAISALLPGVAEPRHVAEVRAILQVPNSRPEPEDRRAL*
```

LGP2021

```
                                                        SEQ ID NO: 25
MPQRRTIQVTEDGRMNLPADIRRVLGLNGAGRIVLMQDEDGIHLTTAEDPLRRVREL

AAPFRRGSGSVVDEFIAERRADSGED*
```

LGP2021

```
                                                        SEQ ID NO: 26
MPLDYALQITAIAFGLSVLGLGGAFIASRVYDRNTRRYDEAAQLHKAD*
```

LGP2021

```
                                                        SEQ ID NO: 27
VQDGIQITCSVTEHVSLAYHENAVPVIREVVVENTSEQELSDVRVRIESRPAVVQPLT

LRIDRIPAGSNHHIELPDVRLDAALLAGFTEASRLELTVIVEDAAGERARHLEELRVLP

PSHWGGGRSAPELLAAFVRPNDPAVDVVLRDAATKLGEAGRETGLNGYYTAKKSR

AWELAEAIWAAIADRRIAYVLPPASFERAGQKVRGPSDVLERKVGTCLDLSLLYAAC
```

-continued

LEQAGLNPVLVLTVGHAFVGVWLQDDDFASATVDDMQLLRKRRDLQDLVFVETTL

LTPEPPATFKVATTQGGVQVEDEAPAALEIAIDVRRCRRRGIRPMDLGDGKPTGIAPA

PTIPLNQTLSAPPSFEEEARAPVDEAPETPVGRVERWKRKLLDLTLRNKLLNFKPGKG

SVSLECASPGALEDGLAAGTEYRLKPLSDVLTGSDERSADLYARRHHDDGRRSYLE

AALARKEIYTTSTEADLDRRLLDLYRLARNGFEEGGANILFLAVGELSWTKKEGEAA

YRAPLLLVPVTLKRSSVRAGFKLALHDDEVRINPTLLEMLREDFKLRMPELEGDLPR

DGSGYDVDGIFRIVRQHVKELRGWEVVPDVVLSAFSFTKYLMWKDLVDRAEVLKR

NPVVRHLIDTPKHSYGDGTPFPEPTRLDREHPPETVFAPLSADSSQLSAVLAAAGGKD

FVLFGPPGTGKSQTIGNMIAQCLAQGRTVLFVSQKTAALEVVQRRLQEIGLGDYCLE

VHSTKAQKSAVLGQLRRAWHERSTPSQGTWDAATSELASLREELNGLVNALHRRRE

NGLSAYEAFGRVIASGGEAPLVLTWPDHLAHNETTLANLRAACRELRPVLASVGSL

VDHPLQGVEATQWSPVWRDDMGAAIRAVEQTLGALRVSGQAFAEAIGLPSLLATY

AGTRGLVVLGNYLVRSEARCGAAFLADGAGDLRRAVAARERFQTTKVQLLGRLTG

RYRPGILDQNLGALLAEWVAAQGANFLVKGGKLKKVSAQVQPYAEGPLPPDLGPD

LTGLIEVARHVKAGCLEELILARLGLPWSNPDCPASEFASAITWAEKVEQLLDILGPL

SLGIDGLRDHLVHLVERQGRALADGGRIAQTYAAFAQDRARANEAMKALGVLAGR

PDPEEPLAAEADWIERSCTIARRLSSGLSRAQGWCAWQAAAQSALKTGLAPLIDALE

DGRIAPDRAEIAFEIAYARWWIDRVVSDDPVLRRFLPARHEDAIQRFRAADARVTEL

SKQVVRSRLGGGIPGATAFGADPEWGTLSHELTKKTAHMPLRKLFGKMPTALTKLT

PCVMMSPLSIAQYLPPDKEPFDVVIFDEASQISPWDAIGALARAKQVVIVGDPEQLPP

TNVGDRGVDDIEDGSDVTDQESILDECLAANIPRRNLDWHYRSRHESLIAFSNSRYY

GGRLVTFPSPVTDDRAVRLTLVPDGVYKRGSGRVNRPEARAVVADIVRRLRDPSFSE

ERRSLGVVTFNGEQQRLIENLLDEQRRSYPELEPFFDRDRWHEPVFVKNLENVQGDE

RDAIIFSVAVGPDQTGRPVSTVSSLNKDGGHRRLNVAITRARRELVVFASMRPEQIDL

GRTRARGVRDFKHFLEFAERGARALAEAFAPTGGDVESPFEAAVMAGLEARGWTV

HTQIGVSGFRIDLGIVHPDAPGRYLAGVECDGATYHSSATARDRDRLREHVLTDLG

WRIRRVWSTEWWMDAEGALTKLDQRLIEDLEADRAKAAAAAAEAPRDVAVEPEA

VEQEHDEPTGEPEVTPPVDTGPSEPANDLEPVTDLIPQRLYADQALPVTPPAPKPEVY

DDVRAYRIVDLNDLGRSVEPGRFYDASYQQALSAMVDHVLAVEGPIYEELLIKRIAR

AHDIQRVGPLVREAIADRIDASVARTEDDGRPVLWPRGEEPRASYPHRPASAAIRSHT

DTPMPELVGIAMTLPSNASEAERARMIGQRLGLSRIEASARARFERASELARQAAVA*

LGP2022

SEQ ID NO: 28

MSVVLYARVSTAEQTLEHQQTQAEAAGFVFDAVVADHGESGRKPLRDRPEGRRLY

DMLRTGDVLVVRWINRLGRSYEDVTGVMRELMQRGVIVRTIISNMTFDGATKDPM

QRAIRDALIAFMAAAGEAELEATREAQKAGIEHARKQADQTAYRGRKPSYTRDQLT

VISGMLGRGAGVSAIAAETGLSRQTIYRVQADPVEAEAALARWA*

LGP2016

SEQ ID NO: 29

MLSLDDIAAAAAGEERDALWRSLVEDMEEAAGRRRGGRGLVQADRPADLARALGR

DRRVQPSRLARSAS*

-continued

LGP2022

MPVGIGIGRGDPLRPAVTRTARFSGPEGFHPGALWLAAASPLLATLLLLVRLAA*

SEQ ID NO: 30

Example 2 *Methylobacterium* Inoculation Effect on Nitrogen Utilization in Rice

*Methylobacterium* isolates were tested for their ability to enhance shoot nitrogen content and/or concentration in rice. A randomized complete block design was used, with 12 treatments in each run; five *Methylobacterium* isolates and a control at two nitrogen levels. The untreated control sample (UTC) was *Methylobacterium* growth medium applied in the same amount as used for the *Methylobacterium* isolates. Each treatment level had an n of 10. All 10 blocks were grown in the same growth chamber and on the same shelf.

Procedure:

Media:

0.5× Murashige and Skoog MS medium with high or low nitrogen

High nitrogen media—10400 uM

Low nitrogen media—250 uM

Pre-Planting:

Rice seeds were de-husked. Average 100 seed count is 2018 mg with approximately 21 g of husked rice per run.

Agar plates containing high or low nitrogen media were prepared.

Planting:

Seeds were sterilized in ~3% sodium hypochlorite+0.05% Tween 20.

Seeds were washed to remove bleach solution and placed on a sterile plate lid to begin drying.

Seeds were plated using a randomized complete block design with each complete block having similarly sized seeds.

Using sterile techniques 8 sterile seeds were evenly spaced in a horizontal line (~40% above the bottom of the plate, using a pre-marked lid as a guide). Seeds were placed with the embryo toward the bottom of the plate and gently pushed into media.

Inoculation:

Each *Methylobacterium* isolate or the culture medium control was applied as an 80 uL streak to the bottom portion of the plate (one isolate per plate) and spread by gently tilting the plate back and forth. A target concentration of $1 \times 10^6$ CFU per seed was applied.

Plates were allowed to dry for at least on hour and placed in a randomized layout in a Percival growth chamber set to 25° C. and 16 hour days.

Seeds were allowed to grow undisturbed for 8 days.

Harvest:

At 8 days after plating the plates were removed from the growth chambers, and the plants were measured as follows.

Plants that were not impeded from growing normally (by physical surroundings unrelated to presence of *Methylobacterium*) were removed from plates, and the number of seedlings for that plate recorded.

Seedlings were scanned using WinRhizo and the images analyzed to determine root and shoot area for each plant.

Seedlings were rinsed to remove any remaining plate media and the shoots separated from the seedlings and dried in a drying oven for at least 3 days.

Dried shoots were combined for each treatment and the mass measured. The plant material was then ground to a powder to be used for nitrogen testing.

Nitrogen analysis was conducted on the powdered samples by Atlantic Microlab (Norcross, GA).

Results of the analyses are shown below. In all tables, pairwise results are presented separately for the High N and Low N treatments. Data was analyzed using Student's t-test and different letters indicate a significant difference between treatments at $p < 0.05$.

TABLE 4

| Exp 1 | | | | | |
| Shoot Area Measurements | | | | | |
| 4A Low Nitrogen Treatment | | | 4B High Nitrogen Treatment | | |
| Treatment | | Mean Shoot Area per Plant (cm²) | Treatment | | Mean Shoot Area per Plant (cm²) |
| --- | --- | --- | --- | --- | --- |
| LGP2033 | A | 0.30 | LGP2020 | A | 0.51 |
| UTC | A | 0.30 | LGP2033 | B | 0.42 |
| LGP2009 | A | 0.29 | LGP2022 | BC | 0.40 |
| LGP2020 | A | 0.29 | LGP2003 | BC | 0.40 |
| LGP2022 | A | 0.28 | UTC | BC | 0.36 |
| LGP2003 | A | 0.28 | LGP2009 | C | 0.34 |

TABLE 5

| Exp 1 | | | | | |
| Root Area Measurements | | | | | |
| 5A Low Nitrogen Treatment | | | 5B High Nitrogen Treatment | | |
| Treatment | | Mean Root Area per Plant (cm²) | Treatment | | Mean Root Area per Plant (cm²) |
| --- | --- | --- | --- | --- | --- |
| LGP2020 | A | 0.93 | LGP2020 | A | 0.99 |
| LGP2022 | A | 0.88 | LGP2022 | B | 0.85 |
| LGP2033 | AB | 0.85 | LGP2033 | B | 0.83 |
| LGP2009 | B | 0.79 | LGP2003 | C | 0.67 |
| LGP2003 | B | 0.77 | LGP2009 | C | 0.62 |
| UTC | C | 0.64 | UTC | C | 0.59 |

TABLE 6

| Exp 1 | | | | | |
| Shoot Nitrogen Concentration | | | | | |
| 6A Low Nitrogen Treatment | | | 6B High Nitrogen Treatment | | |
| Treatment | | Mean % Dry Wt Nitrogen | Treatment | | Mean % Dry Wt Nitrogen |
| --- | --- | --- | --- | --- | --- |
| UTC | A | 2.73 | LGP2020 | A | 4.92 |
| LGP2020 | B | 2.59 | LGP2022 | B | 4.38 |
| LGP2022 | C | 2.48 | LGP2033 | C | 4.02 |
| LGP2033 | C | 2.49 | UTC | D | 3.23 |

TABLE 6-continued

| | Exp 1 Shoot Nitrogen Concentration | | | | |
| --- | --- | --- | --- | --- | --- |
| 6A Low Nitrogen Treatment | | | 6B High Nitrogen Treatment | | |
| Treatment | | Mean % Dry Wt Nitrogen | Treatment | | Mean % Dry Wt Nitrogen |
| LGP2009 | D | 2.35 | LGP2009 | D | 3.27 |
| LGP2003 | D | 2.30 | LGP2003 | D | 3.26 |

Significant and substantial shoot growth promotion was observed for some isolates at high nitrogen. Shoot growth promotion was not observed for the *Methylobacterium* treatments at low nitrogen, consistent with some literature reports which indicate that growth promotion effects from plant-beneficial microbes may not be observed when nutrient availability is too low. Root growth promotion was evident at both nitrogen levels and Root/Shoot ratios are higher under low N than under high N. As expected, plants grown on high N media showed substantially greater shoot N concentration than those grown on low N media. Several *Methylobacterium* isolates demonstrated significantly enhanced shoot nitrogen concentration under high nitrogen growth conditions. Three isolates, LGP2020, LGP2022, and LGP2033, demonstrated the greatest enhancements of shoot growth, root growth and shoot nitrogen concentration.

The above experiment was repeated using four of the same *Methylobacterium* isolates and one additional isolate. Results were similar to those observed in the first assay and are shown in the tables below. LGP2020 (NRRL-B-67892), LGP2022 (NRRL-B-68033), and LGP2033, again demonstrated enhancements of shoot growth, root growth and shoot nitrogen concentration.

TABLE 7

| | Exp 2 Shoot Area Measurements | | | | |
| --- | --- | --- | --- | --- | --- |
| 7A Low Nitrogen Treatment | | | 7B High Nitrogen Treatment | | |
| Treatment | | Mean Shoot Area per Plant (cm²) | Treatment | | Mean Shoot Area per Plant (cm²) |
| LGP2022 | A | 0.18 | LGP2022 | A | 0.30 |
| LGP2033 | A | 0.19 | LGP2033 | AB | 0.30 |
| LGP2020 | A | 0.17 | LGP2020 | AB | 0.29 |
| UTC | A | 0.19 | UTC | AB | 0.26 |

TABLE 7-continued

| | Exp 2 Shoot Area Measurements | | | | |
| --- | --- | --- | --- | --- | --- |
| 7A Low Nitrogen Treatment | | | 7B High Nitrogen Treatment | | |
| Treatment | | Mean Shoot Area per Plant (cm²) | Treatment | | Mean Shoot Area per Plant (cm²) |
| LGP2003 | A | 0.18 | LGP2003 | AB | 0.25 |
| LGP2019 | A | 0.18 | LGP2019 | B | 0.25 |

TABLE 8

| | Exp 2 Root Area Measurements | | | | |
| --- | --- | --- | --- | --- | --- |
| 8A Low Nitrogen Treatment | | | 8B High Nitrogen Treatment | | |
| Treatment | | Mean Root Area per Plant (cm²) | Treatment | | Mean Root Area per Plant (cm²) |
| LGP2033 | AB | 0.57 | LGP2033 | A | 0.67 |
| LGP2022 | AB | 0.53 | LGP2022 | A | 0.66 |
| LGP2020 | A | 0.59 | LGP2020 | A | 0.64 |
| LGP2019 | AB | 0.56 | LGP2019 | B | 0.54 |
| LGP2003 | AB | 0.52 | LGP2003 | B | 0.49 |
| UTC | B | 0.50 | UTC | B | 0.47 |

TABLE 9

| | Exp 2 Shoot Nitrogen Concentration | | | | |
| --- | --- | --- | --- | --- | --- |
| 9A Low Nitrogen Treatment | | | 9B High Nitrogen Treatment | | |
| Treatment | | Mean % Dry Wt Nitrogen | Treatment | | Mean % Dry Wt Nitrogen |
| LGP2020 | AB | 2.36 | LGP2020 | A | 4.28 |
| LGP2022 | AB | 2.30 | LGP2022 | A | 4.06 |
| LGP2033 | AB | 2.38 | LGP2033 | B | 3.68 |
| UTC | A | 2.51 | UTC | BC | 3.45 |
| LGP2003 | B | 2.25 | LGP2003 | C | 3.37 |
| LGP2019 | B | 2.21 | LGP2019 | C | 3.23 |

Percent difference between *Methylobacterium* treatments and UTC at high and low N for 3 different variables: projected root area, projected shoot area and foliar nitrogen concentration, are shown for each experiment. Bold italics are used to denote a statistically significant difference from UTC at p<0.05 using Student's M-est.

TABLE 10

| | | Percent Differences | | | | | |
| --- | --- | --- | --- | --- | --- | --- | --- |
| N Level | Treatment | % Root GP Exp 1 | % Root GP Exp 2 | % Shoot GP Exp 1 | % Shoot GP Exp 2 | % N Enhancement Exp 1 | % N Enhancement Exp 2 |
| High N | LGP2003 | +15.1% | +2.8% | +10.6% | −1.7% | −0.8% | −2.2% |
| | LGP2020 | *+68.5%* | *+35.0%* | *+42.0%* | +14.0% | *+49.7%* | *+23.9%* |
| | LGP2033 | *+41.6%* | *+42.2%* | +16.2% | +15.5% | *+22.4%* | +6.8% |
| | LGP2022 | *+45.4%* | *+40.1%* | +10.8% | +15.8% | *+33.3%* | *+17.7%* |
| Low N | LGP2003 | *+19.4%* | +4.5% | −8.9% | −8.6% | *−15.8%* | *−10.2%* |
| | LGP2020 | *+43.5%* | *+18.3%* | −3.2% | −11.5% | *−5.3%* | −6.1% |
| | LGP2033 | *+31.8%* | +13.8% | +0.7% | −2.5% | *−9.1%* | −5.0% |
| | LGP2022 | *+37.0%* | +6.1% | −8.6% | −8.5% | *−9.0%* | −8.3% |

Example 3 Evaluation of Optimal Nitrogen Dose
for Testing *Methylobacterium* Effect The high nitrogen dose in the experiments described above is the amount in 0.5× MS media, a general plant growth medium, and provides the optimal amount of nitrogen for plant growth. To evaluate plant response to *Methylobacterium* treatment under various reduced nitrogen levels, including a nitrogen level that approximates the amount of nitrogen in a field treated with a 25-30% reduction of optimal nitrogen level, two low nitrogen dose experiments were conducted.

Nitrogen doses used for evaluation of effect of *Methylobacterium* treatment on plant growth were: 5200 uM nitrogen (5000 of rice optimal nitrogen level), 7280 uM nitrogen (700% of rice optimal nitrogen level) and 10400 uM nitrogen (100% of rice optimal nitrogen level). Results are shown in Tables 11-13 below. Data was analyzed using Student's t-test and different letters indicate a significant difference between treatments at $p<0.05$.

TABLE 11

| | Exp 3 Shoot Area Measurements | | | | | |
|---|---|---|---|---|---|---|
| Treatment | 5200 µM N Treatment Mean Shoot Area per Plant (cm$^2$) | | 7280 µM N Treatment Mean Shoot Area per Plant (cm$^2$) | | 10400 µM N Treatment Mean Shoot Area per Plant (cm$^2$) | |
| LGP2020 | A | 0.41 | A | 0.36 | A | 0.41 |
| LGP2033 | B | 0.33 | A | 0.34 | B | 0.34 |
| Control | C | 0.28 | B | 0.25 | BC | 0.30 |
| LGP2019 | C | 0.27 | B | 0.28 | C | 0.28 |

TABLE 12

| | Exp 3 Root Area Measurements | | | | | |
|---|---|---|---|---|---|---|
| Treatment | 5200 µM N Treatment Mean Root Area per Plant (cm$^2$) | | 7280 µM N Treatment Mean Root Area per Plant (cm$^2$) | | 10400 µM N Treatment Mean Root Area per Plant (cm$^2$) | |
| LGP2020 | A | 0.82 | A | 0.78 | A | 0.79 |
| LGP2033 | B | 0.70 | A | 0.77 | B | 0.71 |
| LGP2019 | B | 0.62 | B | 0.64 | C | 0.57 |
| Control | C | 0.47 | C | 0.45 | D | 0.49 |

TABLE 13

| | Exp 3 Shoot Nitrogen Concentration | | | | | |
|---|---|---|---|---|---|---|
| Treatment | 5200 µM N Treatment Mean % Dry Wt Nitrogen | | 7280 µM N Treatment Mean % Dry Wt Nitrogen | | 10400 µM N Treatment Mean % Dry Wt Nitrogen | |
| LGP2020 | A | 4.70 | A | 4.40 | A | 4.61 |
| LGP2033 | B | 3.77 | B | 4.02 | B | 3.96 |
| LGP2019 | C | 3.14 | C | 3.42 | C | 3.41 |
| Control | C | 3.13 | C | 3.22 | C | 3.34 |

Nitrogen doses used for evaluation of effect of *Methylobacterium* treatment on plant growth were: 1560 uM nitrogen (15% of rice optimal nitrogen level), 2600 uM nitrogen (25% of rice optimal nitrogen level) and 5200 uM nitrogen. (50% of rice optimal nitrogen level). Results are shown in Tables 14-16 below.

TABLE 14

| | Exp 4 Shoot Area Measurements | | | | | |
|---|---|---|---|---|---|---|
| Treatment | 1560 µM N Treatment Mean Shoot Area per Plant (cm$^2$) | | 2600 µM N Treatment Mean Shoot Area per Plant (cm$^2$) | | 5200 µM N Treatment Mean Shoot Area per Plant (cm$^2$) | |
| LGP2020 | A | 0.28 | A | 0.32 | A | 0.38 |
| LGP2017 | A | 0.27 | AB | 0.28 | AB | 0.31 |
| LGP2019 | AB | 0.26 | B | 0.26 | B | 0.26 |
| Control | B | 0.23 | C | 0.22 | B | 0.25 |

TABLE 15

| | Exp 4 Root Area Measurements | | | | | |
|---|---|---|---|---|---|---|
| Treatment | 1560 µM N Treatment Mean Root Area per Plant (cm$^2$) | | 2600 µM N Treatment Mean Root Area per Plant (cm$^2$) | | 5200 µM N Treatment Mean Root Area per Plant (cm$^2$) | |
| LGP2020 | A | 0.75 | A | 0.73 | A | 0.71 |
| LGP2017 | AB | 0.72 | B | 0.65 | AB | 0.66 |
| LGP2019 | B | 0.65 | B | 0.63 | B | 0.61 |
| Control | C | 0.45 | C | 0.44 | C | 0.45 |

TABLE 16

| | Exp 4 Shoot Nitrogen Concentration | | | | | |
|---|---|---|---|---|---|---|
| Treatment | 1560 µM N Treatment Mean % Dry Wt Nitrogen | | 2600 µM N Treatment Mean % Dry Wt Nitrogen | | 5200 µM N Treatment Mean % Dry Wt Nitrogen | |
| LGP2020 | A | 3.03 | A | 3.65 | A | 4.67 |
| LGP2017 | A | 3.00 | B | 3.51 | B | 4.22 |
| LGP2019 | AB | 2.86 | C | 3.30 | C | 3.25 |
| Control | B | 2.73 | D | 2.90 | C | 3.15 |

Results again demonstrate significant and substantial shoot and root growth promotion and increased levels of shoot nitrogen levels resulting from treatment with *Methylobacterium* isolates. Shoot area correlated closely to nitrogen levels measured in shoots. Although root area measurements were not observed to be in proportion to increased nitrogen uptake as measured in shoots, additional observations noted that numbers of root tips were increased in line with enhanced nitrogen uptake as measured in shoot nitrogen concentration.

Experiments to identify additional *Methylobacterium* strains that can enhance plant growth and development under reduced nitrogen levels are conducted using a 7280 µM nitrogen treatment, representing 70% of the optimal N level for rice, or a 30% reduction in nitrogen fertilizer application for rice cultivation. Analysis of NLS0693 in this manner demonstrated that this strain resulted in increased shoot nitrogen concentration and increased shoot area in the rice plate assay when the concentration of nitrogen in the media is 70% of the standard nitrogen concentration.

Example 4. Increases in Rice Yield by Application
of *Methylobacterium*

Rice field trials were conducted at three locations, all near Humphrey, AR, for the purpose of evaluating the effects of three *Methylobacterium* isolates applied as a seed treatment. Treatments included each *Methylobacterium* isolate and an untreated control applied to rice seeds with and without a base treatment of insecticide only (active ingredient Clothianidin). The trial was conducted using a Randomized Complete Block Design (RCBD) with 4 reps per location. LGP2016 (NRRL B-67341), LGP2019 (NRRL B-67743) and LGP2017 (NRRL B-67741) were applied to rice seeds at a target concentration of $10^6$ CFU/seed.

The *Methylobacterium* isolates increased yield in rice field trials as compared to the untreated control both with and without insecticide treatment as shown in the Table below.

TABLE 17

Mean yield (Bu/A) Increase over control and percent increase shown (Bold italics indicates a significant difference at p < 0.05 using Fisher's LSD test.)

| Treatment | UTC | LGP2016 | | LGP2019 | | LGP2017 | |
|---|---|---|---|---|---|---|---|
| Without insecticide treatment | 143.8 | 150.1 | +6.3 (4.3%) | *156.2* | *+12.4* *(8.6%)* | 152.4 | +8.6 (6.0%) |
| With insecticide treatment | 151.8 | *164.3* | *+12.5* *(8.2%)* | 155.4 | +3.6 (2.4%) | 158.2 | +6.4 (4.2%) |

Also provided herein are methods of improving growth and yield of rice plants by treating rice plants, plant parts or seeds with one or more *Methylobacterium* isolates. In some embodiments, harvested seed yield and/or nutrient content of rice plants is improved. In some embodiments, rice seeds are treated and such treatment provides for increased rice seed yield. In some embodiments, the *Methylobacterium* isolate is selected from the group consisting of LGP2016 (NRRL B-67341), LGP2017 (NRRL B-67741), LGP2019 (NRRL B-67743) and variants of these isolates. Rice plants, plant parts or seeds coated with *Methylobacterium* isolates and/or compositions are also provided herein. In certain embodiments, the *Methylobacterium* has chromosomal genomic DNA having at least 99%, 99.9, 99.8, 99.7, 99.6%, or 99.5% sequence identity to chromosomal genomic DNA of LGP2016, LGP2017, or LGP2019

Example 5. Procedure to Test *Methylobacterium* Inoculation Effect on Nitrogen Utilization in Rice Additional *Methylobacterium* strains, including *Methylobacterium* strains that caused increased root length during early rice growth from Example 1, are tested for *Methylobacterium* inoculation effect on nitrogen utilization in rice. The experiment is conducted replacing the high and low nitrogen conditions with using 7280 uM nitrogen (70% of rice optimal nitrogen level). Data can be analyzed using Student's t-test to determine significant differences between strains at p<0.05 to determine strains that have increased nitrogen uptake compared to untreated control samples.

Results shown in Table 18 below provide percent differences in foliar N concentration in treated rice plants compared to N levels in untreated seedlings. Foliar tissue was harvested, dried, and assayed for nitrogen concentration via elemental combustion analysis.

TABLE 18

| *Methylobacterium* Strain | Percent difference from Untreated in Foliar N concentration (% by mass) | Number of times tested |
|---|---|---|
| LGP2020 | +45.2% | 9 |
| LGP2023 | +47.6% | 1 |
| LGP2031 | +38.2% | 3 |
| LGP2034 | +43.9% | 1 |
| LGP2029 | +35.7% | 3 |
| LGP2021 | +41.0% | 1 |
| LGP2167 | +40.5% | 1 |
| LGP2030 | +32.0% | 3 |
| LGP2002 | +42.8% | 1 |
| LGP2018 | +37.5% | 1 |
| LGP2001 | +29.2% | 1 |
| LGP2015 | +27.9% | 1 |
| LGP2188 | +3.0% | 1 |
| LGP2189 | −4.8% | 1 |
| LGP2005 | −4.9% | 1 |
| LGP2004 | −4.7% | 1 |
| LGP2032 | +30.0% | 1 |
| LGP2024 | +31.3% | 1 |
| NLS0681 | +27.2% | 1 |
| NLS0594 | +24.2% | 1 |
| NLS0479 | +43.2% | 1 |
| NLS1310 | +44.2% | 1 |
| NLS0612 | +38.1% | 1 |
| NLS1312 | +36.5% | 1 |
| NLS0473 | +32.6% | 1 |
| NLS0706 | +34.5% | 1 |
| NLS0725 | +34.9% | 1 |
| NLS0159 | +5.1% | 1 |
| NLS0229 | −1.5% | 1 |

Example 6: Growth of *Methylobacterium* Isolates Containing Methane Monooxygenase (sMMO) Genes Using Methane as Sole Carbon Source

*Methylobacterium* strains and positive and negative controls are grown on ammonium mineral salts (AMS) media plates, and serial dilutions conducted to determine the appropriate dilution for a target range of 30-300 colonies per plate. For the initial sample tube, 20 ml of 0.9% saline was added, and the mixtures was vortexed for 5 minutes individually using a standard test tube adaptor or up to 6 at a time using a horizontal tube adaptor (SI-V506 for vertical holder). A 1:10 dilution series was created from the initial tube (10E0) to 10E-6. The first time a sample was analyzed, all dilutions were plated to identify the target range of 30-300 colonies per plate. A pure *Methylobacterium* positive control sample was plated so there would be 50-100 colonies per plate.

After completion of the dilution series, the appropriate dilutions were plated onto AMS agar plates in triplicate, and a spreader was used to spread the cells around the plate. A new sterile plastic spreader was used for each dilution or a glass spreader was flamed between dilutions. When finished plates were placed upside down in the acrylic vacuum chamber. A vacuum was applied to create a partial vacuum in the gas-tight vessel (typically −15 psig). High-purity methane (99.999%) was added to create an internal vessel pressure of 0 psig. This creates a methane:air ratio of ~1:2.

After 10 days the number of colony forming units per sample was counted and recorded. Any plates that have no colonies were placed back in the incubator and checked at 14 days and then 2 days if necessary. Growth of *Methylobacterium* strains containing sMMO genes and positive control strains is observed, whereas no growth is observed on negative control plates.

Example 7: Sequences of sMMO Protein Components and Genes Encoding Same

Sequences of genes from representative *Methylobacterium* strains that encode sMMO protein components and the encoded protein sequences are provided in the accompanying sequence listing as noted in the Tables below.

TABLE 19

| Strains | SEQ ID NO | sMMO Component |
|---|---|---|
| NLS0737 NLS0770 | 1 | Regulatory B component amino acid sequence |
| NLS0737 NLS0770 | 2 | Hydroxylase beta chain amino acid sequence |
| NLS0737 NLS0770 | 3 | Reductase C component amino acid sequence |
| NLS0737 NLS0770 | 4 | Hydroxylase alpha chain amino acid sequence |
| NLS5278 NLS5334 NLS5480 NLS5549 | 5 | Regulatory B component amino acid sequence |
| NLS5278 NLS5334 NLS5480 NLS5549 | 6 | Hydroxylase beta chain amino acid sequence |
| NLS5278 NLS5334 NLS5480 NLS5549 | 7 | Reductase C component amino acid sequence |
| NLS5278 NLS5334 NLS5480 NLS5549 | 8 | Hydroxylase alpha chain amino acid sequence |

TABLE 20

| Strains | SEQ ID NO | sMMO Component |
|---|---|---|
| NLS0737 NLS0770 | 9 | Regulatory B component nucleotide encoding sequence |
| NLS0737 NLS0770 | 10 | Hydroxylase beta chain nucleotide encoding sequence |
| NLS0737 NLS0770 | 11 | Reductase C component nucleotide encoding sequence |
| NLS0737 NLS0770 | 12 | Hydroxylase alpha chain nucleotide encoding sequence |
| NLS5278 NLS5334 NLS5480 NLS5549 | 13 | Regulatory B component nucleotide encoding sequence |
| NLS5278 NLS5334 NLS5480 NLS5549 | 14 | Hydroxylase beta chain nucleotide encoding sequence |
| NLS5278 NLS5334 NLS5480 NLS5549 | 15 | Reductase C component nucleotide encoding sequence |
| NLS5278 NLS5334 NLS5480 NLS5549 | 16 | Hydroxylase alpha chain nucleotide encoding sequence |

Example 8 Rice Field Evaluation

Mitigation of methane ($CH_4$) emission from the rice crop-soil system was evaluated following the application of NLS0737 and NLS0770 to rice seeds and evaluation of methane levels during the crop season. Two sites near Ita Ibate and Mercedes were used in the testing program. Both locations were in the main rice growing areas in the Corrientes province of Argentina. The plots were installed and cultivated using conventional rice farming operations. Trial layouts are provided below.

TABLE 21

Macro plots with replicates. RCBD with 5 true replicates. 2 locations.

| Location | Width m | Length m | Area m² | Reps | # Trt | Plots/ location | Area/ location m² |
|---|---|---|---|---|---|---|---|
| Ita Ibate | 5.78* | 20 | 115.6 | 5 | 7 | 35 | 4046 |
| Mercedes | 1.95** | 15 | 29.25 | 5 | 7 | 35 | 1024 |

*33 rows × 17.5 cm
**11 rows × 17.5 cm

TABLE 22

Treatments: Yield + Methane

| Trt | Name | Rate | Target |
|---|---|---|---|
| T1 | Untreated control | | Control |
| T2 | Rizoderma | 200 mL Premax T + 600 mL Rizoderma | Control |
| T3 | NLS0737.05 | 62 g/100 kg | Methane |
| T4 | NLS0770.05 | 62 g/100 kg | Methane |

Seed Treatment and Planting Process

Rice seeds were treated in rotating drums in small batches. A photographic record of the process and final seed appearance for each treated batch were collected. Seed was treated with base fungicide+insecticide for all treatments ((Acronis (BASF)–thiophanate methyl 36.9%+pyraclostrobin 4.1% or Thiram+Carbendazim+Imacloprid). NLS0737 and NLS0770 were applied at a rate of 62.5 g in 600 ml of water/100 kg of seed for a target of $10^6$ CFU per seed. Seed was enumerated for CFU of viable PPFMs and planted within seven days of seed treatment. Both locations were planted using conventional methods on a commonly farmed varietal, IRGA 424 RI seed, at 100 Kg/ha. Fertilizer was applied pre-plant broadcast using 60-100 kg KCl, and 100 kg/ha MAP at planting, in the seed row. Urea was applied pre-irrigation at 100 kg/ha and post irrigation at 50 kg/ha during the spike differentiation stage.

Untreated control: includes base chemical fungicide/insecticide treatments following farmer standards. Seed included professional seed treatment—all biological treatments were added as over treatments. At Mercedes seed was treated with Thiram+Carbendazim+Imidacloprid. At Ita Ibate the seed was treated with Acronis (BASF)–thiophanate methyl 36.9%+pyraclostrobin 4.1%.

Commercial control: included a biostimulant/biofertilizer treatment on top of the base chemical treatment. Rizoderma (*Trichoderma harzianum*) was applied per recommended label rate.

Foliar Spray:

Additional treatments were applied as foliar applications using NLS0737 and NLS0770. Conventional backpack spray technologies with a 2 meter boom were used to deliver 125 g/acre of the dried powder inoculant (~$10^9$ CFU per gram) in water at nine gallons/acre and ~20 psig. Applications were made three times throughout the growing season at approximately 15, 35 and 50 days after sowing. Plots were split to allow randomized complete block analysis.

Pre-Plant Soil Sampling and Crop Measurements

Soil was analyzed (0-20 centimeteres depth) to determine % organic matter, % total nitrogen, $NO_3$, $NH_4$, pH, complete macro-micro nutrient analysis and cations+EC, and soil texture.

Crop measurements included early stand count at four and 20-days post first observed emergence in the field. Plant diseases throughout all crop stages were scouted using quantitative incidence and severity scales. Digital images for NDVI and other spectral indices for visual and quantitative assessment of treatment effects were collected using two drone flights at vegetative and reproductive stages with multispectral sensors. Weekly satellite images were analyzed from Planetscope satellite imagery at 3-m resolution for NDVI time series. GPS coordinates at each corner of trial polygons were used to digitize data and analyze statistical comparisons of treatment effects through different spectral indices associated with crop growth and health. Digital elevation models were included in the two field-scale trials to assess elevation effect on crop performance. Grain yield at plot and sub-strip scale were collected by hand. Grain samples containing one kilogram from each block were assed for grain quality: % whole grain, % broken, and % chalky grain. Complete daily weather information and irrigation scheduling and amounts were recorded.

Methane Measurements:

Greenhouse gas collections methods were designed and contracted with specialists from The USDA ARS and executed by scientists under contract from EEA. INTA. Balcarce (National Institute of Agricultural Technology, Balcarce Agricultural Experimental Station). Gas samples were collected using standard methods recognized by the ICCP following standard GC protocols. Headspace gas samples were analyzed at using dedicated gas chromatography methods on an Agilent Gas Chromatography system. Cylinder head space samples were collected between 9 am and 11 am. There were 5 samples collected per plot at 15-20-min intervals. A total of 100 samples were collected per time point, from 20 chambers installed per field. Measurements were taken six times during the crop season:

1. Early tillering. 5 days after first irrigation. approx. 20 days after emergence—expected peak
2. Mid tillering: approx. 35 days after emergence
3. Late tillering: 50 days after emergence
4. Pre flowering: 65 days after emergence six measurements across the season, a model was fit to estimate total emission in kg/ha during the entire crop cycle.

Methane Emission Results

Methane emission rates are shown in the tables below. Peak emission occurred between late tillering and flowering, as expected. Total emissions were strongly influenced by temperature fluctuations. Overall lower emission at ItaIbate vs Mercedes were most likely related to later planting which led to overall lower crop growth, both below and above ground. Average lower temperature and radiation during $CH_4$ measurements combined with significant soil texture differences (ItaIbate sandier) also contributed to the difference in both methane emissions and reduced yield.

NLS0737 and NLS0770 showed reductions in $CH_4$ emissions during peak rice growth at both locations in Argentina. At the Mercedes site NLS0737 reduced methane emissions 28% (151 kg/ha) and NLS0770 reduced emissions 23% (125 kg/ha). At the Ita Ibate site NLS0737 reduced methane emissions 7% (19 kg/ha) and NLS0770 reduced emissions 4% (11 kg/ha).

TABLE 23

| Ita Ibate | % | Kg/HA | Reduction (Kg/HA) |
|---|---|---|---|
| NLS0737 | 7.0 | 251 | 19 |
| NLS0770 | 4.1 | 259 | 11 |
| Avg. | 5.6 | 270 | 15 |

| Mercedes | % | Kg/HA | Reduction (Kg/HA) |
|---|---|---|---|
| NLS0737 | 28.1 | 386 | 151 |
| NLS0770 | 23.3 | 412 | 125 |
| Avg. | 25.7 | 537 | 138 |

TABLE 24

| Comined Locations CH4 Emission Reductions | | |
|---|---|---|
| AVG | KG/HA | 76.5 |
| AVG | % | 15.6 |

Methane measurements showing patterns across dates at the Mercedes locations are provided in Table 25 below. Different letters represent statistically significant differences between treatments at late tillering and flowering stages. The decrease in methane at pre-flowering correlates with the lowest temperature of the season.

TABLE 25

| | Methane Emission Rate (kg/ha/day) | | | | | |
|---|---|---|---|---|---|---|
| Treatment | Early tillering (4 DAF*) | Mid tillering (18 DAF) | Late tillering (39 DAF) | Pre flowering (60 DAF) | Flowering (69 DAF) | Maturity (82 DAF) |
| Control (UTC) | 1.35 | 5.50 | 12.17 B | 5.82 | 7.54 B | 0.14 |
| Rizoderma | 0.64 | 4.45 | 9.49 AB | 5.79 | 7.51 B | 0.22 |
| NLS0737 | 0.71 | 4.23 | 8.19 A | 5.01 | 5.22 A | 0.23 |
| NLS0770 | 0.32 | 4.13 | 8.28 A | 5.58 | 7.13 B | 0.12 |

*DAF—days after flooding initiation

5. Flowering: 80 days after emergence—expected peak
6. Advanced grain filling (pre-maturity): 100 days after emergence Under paddy rice conditions peak methane emissions are generally recognized between time points 5 and 6. Response variables include Methane ($CH_4$), Nitrous oxide ($N_2O$) and Carbon Dioxide ($CO_2$), expressed in kg/ha/day. Using the Rice Yield Results Rice yield at the Mercedes site was increased over the untreated control 17% by NLS0737 (+27 bu/acre) and 6% by NLS0770 (+9 bu/acre). Due to the delayed planting, the lower solar incidence and the late season rains, the yield from the Ita Ibate site was reduced 44% below the Mercedes site. No differences in yield by treatment were seen in Ita Ibate. At an alpha of 0.15 only the seed treated and sprayed yield (ST/F) from the NLS0737 blocks were considered significantly different from the untreated control. The NLS0737 and the NLS0770 seed treated (ST) yields were similar but not significantly different from each other. The NLS0770 seed treated and sprayed blocks (ST/F) were lower, but not significantly different from the untreated control. The biological control blocks were similar to the NLS0737 seed treated and sprayed (ST/F) treatments.

TABLE 26

| Mercedes | Yield (α) | % Yield (α) | Bu/Ac | lb/Ac |
|---|---|---|---|---|
| Control (UTC) | 158 a | | | |
| NLS0737ST/F (*) | 185 b | 17.1 | 27 | 1215 |
| BiolControl | 183 b | 15.8 | 25 | 1125 |
| NLS0737ST | 173 ab | 9.5 | 15 | 675 |
| NLS0770ST | 167 ab | 5.7 | 9 | 405 |
| NLS0770ST/F (*) | 154 a | −2.5 | −4 | |

(*) Seed treatment (ST) followed by three foliar (F) applications
(α) Different letters represent statistically significant differences between treatments at a = 0.15

Example 9 Identification of *Methylobacterium* Strains, Variants and Derivatives Genomic sequences that can be used to identity and distinguish NLS0737 and NLS0770 from other *Methylobacterium* strains are identified by an exact k-mer analysis of whole genome sequences of over 5000 public and propritary *Methylobacterium* isolates. NLS0737 and NLS0770 are closely related and may be, or originate from, a single *Methylobacterium* isolate. A 300 nt DNA fragment common to both isolates, but not found in other *Methylobacterium* strains analyzed is provided as SEQ ID NO:31. Genomic sequences that can be used to identity and distinguish NLS5278, NLS5334, NLS5480, and NLS5549 from other *Methylobacterium* isolates are identified in the same manner. NLS5278, NLS5334, NLS5480, and NLS5549 are closely related and may be, or originate from, a single *Methylobacterium* isolate. A 300 nt DNA fragment common to NLS5278, NLS5334, and NLS5480, but not found in other *Methylobacterium* strains analyzed is provided as SEQ ID NO:32.

```
                                    SEQ ID NO: 31
AAGGCCCCTCAATATAAGGAGAGATTCCCTACCGGAGTGACGTTTCACT

GCGCAAGTTATACAGATTGCAAAAATCACATTGGTAGCACCTACTCCCC

AAGCTACGCCAATCTCTCCAACTAACGGCCCTACCAGAACAGCAGCTAC

TCGGCCAACGCTTAGTACTGCAGTAGTAAGGAATATCGCTCTGCCATTT

CCATTTGCGAGCAATACGGCACCACATAAGCTGAAAATAGCGTTAACTG

CATAAAACGGTATTAATACTTGCACTAACGCCGTTGCTGAGACCCATTT

TTCCCC

SEQ ID NO: 32
CGCGCCAAGCGATCCTCCGGCGAGACATCCAGCGCGCGATCCTCCGACA

CGTCGAAGGGATGCCCGTTGATCGAGGATCGGGCCTTGTGGCGGATGGC

TGGGTAATCCGCCTTGATCTTCGCTAGGTCCTCCGCGCTCATAGCGCCA

TTGCGCGCCGGTACACTGTAATTGGCCGTCCGCTGGAACACCGTGAGAT
```

```
                      -continued
GGGCGGCCTTCGCCGCGATCACCGGAGCGGCTTGGATCCCGGTGGAACC

AGTCCCGATCAGGCCAACCCGCCGGCCCGTGAAATCGACATCCTCATGG

GGCCATC
```

Assays for detection or identification of specific *Methylobacterium* strains and closely related derivatives are developed using the disclosed unique genomic DNA essentially as described in WO2022076588 Example 3.

Unique genomic DNA sequences of additional *Methylobacterium* strains disclosed herein were identified by BLAST analysis of approximately 300 bp genomic DNA fragments using a sliding window of from 1-25 nucleotides and compared to whole genome sequences of over 1000 public and proprietary *Methylobacterium* isolates. Genomic DNA fragments were identified that have weak BLAST alignments, indicative of approximately 60-95% identity over the entire fragment, to corresponding fragments of a *Methylobacterium* of interest. Unique fragments from the various disclosed strains useful for assay development are provided as SEQ ID NOS: 33-75 as shown in the table below.

TABLE 27

| STRAIN | SEQ REFERENCE | SEQ ID |
|---|---|---|
| LGP2001 | ref3__25009 | SEQ ID NO: 33 |
| LGP2001 | ref3__25219 | SEQ ID NO: 34 |
| LGP2001 | ref1__4361220 | SEQ ID NO: 35 |
| LGP2001 | ref1__4602420 | SEQ ID NO: 36 |
| LGP2002 | ref4__930 | SEQ ID NO: 37 |
| LGP2002 | ref1__142021 | SEQ ID NO: 38 |
| LGP2002 | ref4__930 | SEQ ID NO: 39 |
| LGP2003 | ref1__86157 | SEQ ID NO: 40 |
| LGP2003 | ref1__142469 | SEQ ID NO: 41 |
| LGP2003 | ref1__142321 | SEQ ID NO: 42 |
| LGP2004 | ref1__194299 | SEQ ID NO: 43 |
| LGP2004 | ref1__194305 | SEQ ID NO: 44 |
| LGP2004 | ref1__194310 | SEQ ID NO: 45 |
| LGP2009 | ref1__153668 | SEQ ID NO: 46 |
| LGP2009 | ref1__3842117 | SEQ ID NO: 47 |
| LGP2009 | ref1__3842278 | SEQ ID NO: 48 |
| LGP2015 | ref1__135566 | SEQ ID NO: 49 |
| LGP2015 | ref1__135772 | SEQ ID NO: 50 |
| LGP2015 | ref1__169470 | SEQ ID NO: 51 |
| LGP2017 | ref1__1185955 | SEQ ID NO: 52 |
| LGP2017 | ref1__3282585 | SEQ ID NO: 53 |
| LGP2017 | ref1__4194637 | SEQ ID NO: 54 |
| LGP2018 | ref1__4871392 | SEQ ID NO: 55 |
| LGP2018 | ref1__1266930 | SEQ ID NO: 56 |
| LGP2018 | ref1__17614 | SEQ ID NO: 57 |
| LGP2019 | ref1__458355 | SEQ ID NO: 58 |
| LGP2019 | ref1__459688 | SEQ ID NO: 59 |
| LGP2019 | ref1__3158527 | SEQ ID NO: 60 |
| NLS0497 | ref1__46464 | SEQ ID NO: 61 |
| NLS0497 | ref1__85227 | SEQ ID NO: 62 |
| NLS0497 | ref1__98103 | SEQ ID NO: 63 |
| NLS0693 | ref1__622066 | SEQ ID NO: 64 |
| NLS0693 | ref1__2496 | SEQ ID NO: 65 |
| NLS0693 | ref1__2640477 | SEQ ID NO: 66 |
| NLS1179 | ref1__687571 | SEQ ID NO: 67 |
| NLS1179 | ref1__695522 | SEQ ID NO: 68 |
| NLS1179 | ref1__705877 | SEQ ID NO: 69 |
| LGP2167 | ref1__54084 | SEQ ID NO: 70 |
| LGP2167 | ref1__4816166 | SEQ ID NO: 71 |
| LGP2167 | ref1__2292077 | SEQ ID NO: 72 |
| LGP2020 | ref1__2810264 | SEQ ID NO: 73 |
| LGP2020 | ref1__322980 | SEQ ID NO: 74 |
| LGP2020 | ref1__2785241 | SEQ ID NO: 75 |

SEQ ID NO: 33
GCCCTTCTGTCAGGCGATATTGTATAATGGCGTTGCCCCAATAGAAGCA

GCCATTCGTGCGAGGGCAGCAGCGACGCTAGGTCGAAAGAGCATCCTAA

TCTCGATCAAGATGCGACTGAGATTTCTGATGAAAATATCTAGACACAA

GCAAAGCTGGTGAAATTACAACGATCATGGCGACAATTGCGGCCAATTC

GGCCGGAACTTGAAGGAACATAAAAATGAATATTACAAATATACCGCAA

AGCATGTAGAGTTGCTACACCAAGGGTCGGGACGTCCAAAAAAACTCAC

TGAGGA

SEQ ID NO: 34
GGAACATAAAAATGAATATTACAAATATACCGCAAAGCATGTAGAGTTG

CTACACCAAGGGTCGGGACGTCCAAAAAAACTCACTGAGGAAGTCGACT

GGAAGCACGAGGCGCCCCCCCCAGGAGCGGGGCGACCGGCAAGGGGGCC

CGCAATTGTCGCCATGATCGACCAGCTTAGGTAGGATCCTCTTTCGACC

TAACGAATGGCTGCTTCTATTGGGGCAACGCCATTATACAATATCGCCT

GACCATCTGGAACGCGGCCCGGTCCACCGGCAGGTTGGCGACGACAGCG

TCGGAG

SEQ ID NO: 35
CGGCGTCGACCAGCCGGGCGAACTGCTTGGGCATGCTCTCCCGCGACGC

CGGCCACAGCCGCGTCCCCGTCCCTCCGCACAGGATCATCGGGTGGATT

TGAAAGGCAAAACGGGACATCAGGATAGGCCGCTCAGGCGTTGGCGCTG

AGGCGCTTGATGTCGGCGTCGACCATCTCGGTGATCAGCGCCTCGAGGC

TGGTCTCGGCCTCCCAGCCGAAGGTCGCCTTGGCCTTGGCGGGGTTGCC

CAGCAGCACCTCGACCTCTGCCGGCCGGAACAGCGCCGGGTCGACGATC

AGGTGG

SEQ ID NO: 36
CTGGACATGCGCCCACCCCGGCCAAGTCCGACCGCACCGGCAACCGCTC

CTGTAGTCGTCGTCATCGTTCTCACCCCTGAGGCGGAGACCGTCCGCTA

ACGGGGTGTCTCAAGCAACCGTGGGGCGGAGGAACACGCACGTAGTCGC

GTTTCAAGGTTCGCACGAACGCCTCGGCCATGCCGTTGCTCTGCGGGCT

CTCCAGCGGCGTCGTTTTTGGCACCAAACCAAGGTCGCGGGCGAAGCGG

CGCGTGTCGCGGGGACTGTCAGGAATTTCGTGTGGGGGCGGCCATAGTG

GATCCG

SEQ ID NO: 37
GCAAAACGACCTAATAGTTCTACAGCGGCCATGCGCCAAGTCAGCGCGGT

GAACAGTATACCTGGGAGCAACTTGTCCTCCGAAACCCACATAAAACAA

ATTACTCCTGGCAGTGCCCAGTCCATCAAAATCGAATACAATATTTCTC

GAGGAGGCATCTGTAATAGCCTGCCAAAGCAACAAAGCTATGGCGCCGT

TATGACTTTCATTGCTTCTGGTAGACATAAAATAATATGCCGATTTGTG

ATCCCAAATGTAGAATATTGCCGCATCAATTGCGCCAAGTTTATTTCGG

ATCGAT

SEQ ID NO: 38
GGCGCCAACGGTATGATCGCATGATTTTCCTGCGGCATAGCTTGCGGGA

ATGGCGTATTTGGCGCTCTCCTCAGGAATTTCTAAGGGCATACGCAGGA

ACTCTACAGCACTTTTACTGGTATTTTGTAGTGACAGCGGAGGAGGCTG

GTGCTCAAGGTAATCGTGATGAAGTGATCCGGGCCATTCGGGGCGCGTT

TCTAGTCTTTCCAATCCGCGCCCTGTACCACGTATTACGCCGGACCGGT

CTGCGCCGCGCCGCCCTCTTGACCGCCCTAAATGTCTAAGAGCGTCTAA

CAAAGC

SEQ ID NO: 39
GACGATATCGCTCATCTTCACTGCATTGAAGCTGGTGCCGTACTGCATA

GGGATGAAAAAGTGATGCGGATAGACGGCTGACGGGAAAGCGCCTGGTC

GATCGAAGACTTTGCTGACGAGGTTGTGGTAGCCCCGGATATAGGCATC

GAAGGCCGGGACGTTGATCCCATCCTTTGCCTTATCTTGACTGGCGTCG

TCGCGTGCCGTCAGAACGGGCACGTCGCAGGTCATCGAGGCCAGCACCT

TGCGGAACACCTGCGTTCCGCCGTTGGGATTATCGACGGCGAACGCGGT

GGCCGC

SEQ ID NO: 40
AGCCCACAAGCCTGATGCACTTAACTACATCCTCTAATGTCGCGCCAAT

TTGCTTGGCGGCAGGGGATGTTGTATCGTCATAGGCTTGTCTAACCGGA

ACTTGTTTGCCAATCTCTTTGGCGATCGCAACCGCCATCTCGTGTTCGT

CAACCATGTGCGCGTTCCTCTAATTGCACTCATGGTGCCACGTGCACCT

CCGATCGTCTCGTGTCTAGAATGAAGGTGGGAACAACCTTACACAGGCT

TTCGCGACGCGCGAATTTCTGGTTTCTCCGCCTCGGATGTGGGTTTGAG

CGCTTC

SEQ ID NO: 41
CTTTTCATTTGTCATGATCTCGACCAAGGTATTCACGGCAAGCTCGGTC

TGTTGCTTAGCAAGTGCCTGAACTTCGCGAACGATCGGCTCTCGACCCT

TCGGGTTCGAGACCTGTCCCTTTTGAAAACCACGTGCCCTACACTTTTC

GGGATCAAGGTGCGGGTTGGCTTTGGTCAAAATTCTCTGGCGTCCCATT

ACACGCCCTCCGCATCATCGTTCCCGCGAACGATCTGACCCCCGACTTC

CGCGAGGAAGCGTGTGGCGTGATCCTCGAAGCGGAATGCCACCTCGAAC

TGTTCC

SEQ ID NO: 42
CAGCAGCAAGCAGATCGTTGAAAACCGCTTGAACCGCATCTTGATCGGG

ACCGGAACCAATCAGGTCATCTAGGTAAACCGAGACGTAAACTCGTTTG

CGCTCGGCATCTTTCAGAACGTCCGTGATGCCAGACCGCATTAGTACCA

TCGTCGCCAAGGCGGGCGACTGAACGAAGCCGATCGGCAGAGAGTAACG

GGGACCGCCCCTAATCGGGTTGCGAACGCAAGACCACTTAGCAAAGGTT

CGAGCACGGCCGAACTTCGCATGGTGGAGAGCCGCGGCAACACGGTTCC

GTGATA

SEQ ID NO: 43
GGAAATCGGCTTCAAGTACGACGTCACGCCGGCCATGCAGGTCACGGGT

GCACTGTTCAATCTCGAGCGCGACAACCAGCCGTTCCCCTCGAACGTGG

AGTCCGGCCTCGTCCTTGGCGCAGGTCAGACACGCACCCAGGGCGCGGA

-continued

AATCGGCCTGGCCGGCTATCTAACCGATTGGTGGCAGGTCTTTGGCGGC

TACGCTTATACCGAGGCACGCGTACTCTCGCCACTGGAAGACGATGGAG

ACGTGATCGCAGCAGGTAATCTCGTCGGCAACGTTCCGCTAAATACTTT

CAGTCT

SEQ ID NO: 44

CGGCCTGGCCGGCTATCTAACCGATTGGTGGCAGGTCTTTGGCGGCTAC

GCTTATACCGAGGCACGCGTACTCTCGCCACTGGAAGACGATGGAGACG

TGATCGCAGCAGGTAATCTCGTCGGCAACGTTCCGCTAAATACTTTCAG

TCTGTTCAACAAGTTCGATATCAACGAGAATTTCTCCGTTGCTCTGGGC

TATTACTATCAGGATGCCAGCTTTGCCTCCTCAGACAATGCAGTGCGTT

TGCCAAGTTATTCGCGGTTCGATGGCGGGTTGTTCTATCGATTCGACGA

GTTGAC

SEQ ID NO: 45

ACGTTCCGCTAAATACTTTCAGTCTGTTCAACAAGTTCGATATCAACGA

GAATTTCTCCGTTGCTCTGGGCTATTACTATCAGGATGCCAGCTTTGCC

TCCTCAGACAATGCAGTGCGTTTGCCAAGTTATTCGCGGTTCGATGGCG

GGTTGTTCTATCGATTCGACGAGTTGACACGCGTTCAGCTTAGCGTCGA

GAACATTTTCGACAGGCGTTACATCATCAACTCCAACAACAACAACAAC

CTCACGCCTGGCGCGCCGAGAACAGTCCGCGTGCAATTGATCGCTCGGT

TCTAAA

SEQ ID NO: 46

TAGACATTCCAACAAACCGGCAAGAGGCTCGTCCTCACTCGAGGATTTG

TTGGGACTTGCATGATGTCGAAGCGGAGCCGTTATGACCTGGGTGCGAT

CATGCGCCGAGCATGGGAGATGGCTCGGGAGGCGGCATTCGCGGTTGGC

GAGCGGGCACGGACTCACCTTGCTGCCGCGATGCGCAGCGCGTGGGCCG

AAGCCAAGTTGGCACTCGCGCCCACGAAGACGGAGCAGGATCGTCTCTC

TCCGAGCGACATGATCGGACATGAGGACGCCTACCAAGGCCGGGTTCTA

AAATAT

SEQ ID NO: 47

AAGATGGATACGACAAGCGCGATTACATTATTTGCGAAATAGATGGACA

AATAAAAGACAAAGGACTGATGTATTTCCTTAAATCTGGACAAGTTGAC

CTCTTTCACATAGAAGTCACCACTCCCTTTGGGCAATTTGGTGTCACG

AAAACATAGAGGCCGAACTTCTTAGCTGAATTATCGCGCTCCGGGTTCT

TATGCGGCTGAGTGAAGCGCGGGACAGCTTGCGAGCAGGGCCGCCAATG

GCAGCCGGGATGACACAATGCTCGGTCTCCCGACGCTTCTTCAATCGGG

AGCGCT

SEQ ID NO: 48

AGCTGAATTATCGCGCTCCGGGTTCTTATGCGGCTGAGTGAAGCGCGGG

ACAGCTTGCGAGCAGGGCCGCCAATGGCAGCCGGGATGACACAATGCTC

GGTCTCCCGACGCTTCTTCAATCGGGAGCGCTTCGCAGCCCGGGGCGGC

GCGCTCATGCGTCACGACCTGGGCCCTGCGCACCTTCGCGGCCCCGCCG

-continued

TCCCGGCAGATCCCTGATGCCCCAAGTGGGCGGCCACTCCATCAAAGAA

CCCCGGCCTGTGGCAGATCTCGTAGGCATACCGAGGTTCCGCAGTGCCC

CCACC

SEQ ID NO: 49

ACGGTCACCCCACGGACTGGGCGAGTACCTCACCGGTGTTCTATCATAA

CGCCGAGTTAGTTTTCGACCGTCCCTTATGCGATGTACCACCGGTGTCG

GCAGCCGATTTCGTCCCACCGGGAGCTGGCGTTCCGGTTCAGACCACCA

TCATCGGTCACGATGTCTGGATTGGACACGGGGCCTTCATCTCCCCCGG

CGTGACTATAGGAAACGGCGCGATCGTCGGGGCCCAGGCGGTCGTCACA

AGAGATGTCCCACCCTATGCGGTAGTTGCTGGCGTCCCCGCGACCGTAC

GACGAT

SEQ ID NO: 50

CCAATAAAAGCGTTGGCCGCCTGGGCAACCCGATCCGAGCCTAAGACTC

AAAGCGCAAGCGAACACTTGGTAGAGACAGCCCGCCGACTACGGCGTTC

CAGCACTCTCCGGCTTTGATCGGATAGGCATTGGTCAAGGTGCCGGTGG

TGATGACCTCGCCCGCCGCAAGCGGCGAATTACTCGGATCAGCGGCCAG

CACCTCGACCAAGTGTCGGAGCGCGACCAAAGGGCCACGTTCGAGGACG

TTTGAGGCGCGACCAGTCTCGATAGTCTCATCGTCGCGGCGAAGCTGCA

CCTCGA

SEQ ID NO: 51

CGATGGCACCGACCTGCCATGCCTCTGCCGTCCGCGCCAGAATGGTAAA

GAGGACGAAGGGGGTAAGGATCGTCGCTGCAGTGTTGAGCAGCGACCAG

AGAAGGGGGCCGAACATCGGCATCAAACCTCGATTGCCACTCGGACGCG

AAGCGCGTCTTGAAGGAGGGATGGAAGCGAAACGGCCGCAGAGTAACCG

CCGACGAAAGATTGCACCCCTCATCGAGCAGGATCGGAGGTGAAGGCAA

GCGTGGGTTATTGGTAAGTGCAAAAAATATAATGGTAGCGTCAGATCTA

GCGTTC

SEQ ID NO: 52

AGTCATTGATCAAGCAACCCCTATTGAGTTGGATATCGAAGGATCAAGG

TCGCGTCAATAGATGCATCTATCAGGCCAAATGTCGCTTTTCAAGAATG

GCTCTTTCGAAGCTATCTTTATAATCGCTCGCCATTCTCTCATTACCAA

AATCGACCTTAACTAGCTCGACATTGATGCGAGCAGCTCCGGCAAACGA

GGAGAGATTGACCTTAAAGGAATTGAACGCCTCAAGCAATTCAGACACA

TTACCAGGAGTGCTATAGCAACAACCAGACCCATATCGGTCAATAACCT

CTTTTA

SEQ ID NO: 53

CGCAAAACGATTTATCACTGCCATCTTGTTGTTTGATAACCCTTTTTTA

CCAGACGTTATGCTGGGCGAGAAAGAGGACTAGCAGATCGGAGCGGTAT

CGCGATTTTTCGGTAGTTCGCGCCTACAACAGGATAAGATCCGATAGTG

AAGCAACATGGCTGTTTTTTGATTTGTAAGTCAGCAACTTAAGCAGCCA

-continued

GCCTATCTGCCGTCGCAGACGCTTGAGGCATCGGGCAGCATCTTAGAAA

AGGTGGCAGTAATTGCCACAGCGGAACGTAGCGGCACGGATAAGCACGC

AGGGTC

SEQ ID NO: 54
CCCATCTGGACCCAATATCCCCTTCATCGACAATTCCCGAGTAAGTGTG

GGTTCGAGGATTTCGCGAAACAGCCTTGTTCGTTCCTCCGGCCTTAAAA

TTGGCGTGCCGTCGGGAGATCGATAGGCATCCCTTACCTGCCTTTCGAC

CGCCGGCACACGCGCGCCGGTCGTCGTGTTCACGGCCACGGAATGGACG

AAGGTGCGCCGCTCATTTCGCTCGTTTGCCGTCTCCACCATCCAGGAGG

CCAGCAGGACGGTTTCGTCTCGACCGCCGGTCACACACACCGCAAGGGA

CTCAGG

SEQ ID NO: 55
ACCTGCTAAAATCACGTCCTCTCAGATTGAAAAATCATTGAAGAAACGT

GTCGAACGATTGCCGGGGATTATGACGTTAGATCAATTGAAAAATACAA

GCTTTGAAATTGAGTTACAGCCAAAAGATGCCCCGGATCCGGACCCATC

AGACTTCGGTGGCTAGTTCGAGCCAAACTCGAACGTCGCCATGGCGCGC

AAGTCGCAATACCATTTCACAGCGCAGCGGTTATTTCGTTGTACACTGT

AGCAATGCGTCGGCTTGCGCGCTTCCGCTGGCGATCAAAGGTCCGCCGA

TTTACG

SEQ ID NO: 56
TCCCGAACATACAATGGAGGAAGCGTGTGGTAGGCCAATTTGTAACGAA

ATATGGCATCGGTCACGGCTCTCTCAATAAATTCGATCTCAAGTCTTCT

GAACGAGCATGCCTCATCCTTATCCTGAGCGAACGCCTGCCAGTTTGCA

GTCATTCCAACATACATAGCCAAAAAGGCGAGGTAGACCTTCATACGGG

CACCTCAATCGTCCCCATTCGTTCAAGCTCCTTCAAGATAACAGCCGCA

CCACATTGCTGAGATCGAAGATTCGGATCAAATATTCCATCAAATTTAT

ACTTTC

SEQ ID NO: 57
GCATCCTTTGCGCTCGCAGGCCTAAGGTCAAGCCCGGTTACTTCGTTTG

GTAGAACGAGGTAGACGATGCCTAGTCTTAAGGTGGCCCATGTTAACCA

ACAGGGCCAGAACATGATTATAGTTCCGTTAGATGCCAACTTCGGTTAC

AAAACCGATGGTGAGCAGTCCGACATCATGTTCGAAATACAGGACGCGG

CGCGGTCCGCCGGTCTTGCGGGTGCCGTAGTAGCGTTCTGGCAGTCAGG

TGGACAAACCCGTTTCCGGGGCCCGGCTCCGTGGCACCCATTCCTTCGC

AGCCTC

SEQ ID NO: 58
CAACTATGTAGACCCGACGGTGCGATTTCACTTCGCAAAGCCGCAGGGC

AGCACCCTTGCGCTCAATGTTGACGCCAGCGTGATCTATACTATTACCG

TCACGCACACGCAGGGCGGCGTACAGATTCATCGCGAGAGTAAGAACCA

CCATCAGACCATCACGCGCAGCGACCTGAGCAAGCAGTTCGGCGTTGGT

GTGGCCGACCAGCTGACGCGCGATCAGGTCATGAAGGTGATCGAGTCGG

CATTTCGCGACGCTACCCGCTAAGATCGGCGCCCACGAAACGCTACGAG

ACTAGG

-continued

SEQ ID NO: 59
AGCCGGCATCTTGTTCAAGGCGCTCACCTCGACGCCGACGCTGTAGGCG

ACTTGAGAGGGCGTCTCATATGAACGAAGCATCTTCGCGTAGAGAACCT

TCTTGTTCTCCTGCGTGATGTTCGCTTTGCAGACGTTGACTGCCGCCAT

GAACGCCGAAGCCTTGCGCGCTTCATCGTAATCGCCTGCGAAGGCGGGT

AGTGAAAAGCTTAGTGCAATGGCAAACACAGCCGCCGAACGTCGCATGG

TATCCGTCCCCGATTGACGGCAGTGCCGCCATATCTCGGCTTTAGCAGA

GCTGAT

SEQ ID NO: 60
AACCTGCGCCGGCCGAGGTTTCGCGAGCCGTCGCCACGGGCAACGCCTC

GCCCGCGATGTGCAAAAAAGTCCCCGGCACTTCGCGCCGTCGTCCGATC

CACGACCGCGAATTTCTCAACGAGTACAAGGTGCTTATGGGAGATCCGA

GCGTCCGTCCCGGAGCCCGAGACCGCGCGGCCCGAGTAATAGGCGAAAA

AGACTCCTACTCCTCGGGCTTCTCGGGCCCCCTCAGCAACATCTACGCT

TGCCGCCCATCACCCTGGCGGGAGATCAGCGACGAGACACAGGCCCACT

TCGCCC

SEQ ID NO: 61
CTCAACGTTGCCGCCTTAACCGAAGACTAACTAACATAAATTTCAGTTA

GCCGCGAAACAGAATATGATACTTGGTCTTATACGACGCATAGAGGCGC

ATTCCGTCAAGTCGCGCATTGCAGAGTCCCCCCGAAAATTCGTTTTCTG

GGAGCGAGCAGAAACGTGTGCACGTGTTCTGTCACTCTATTTTCTGGTT

TAGAGCAATCATCTCGCGGCTCAGATCCCGTCGTTCCATAGAGTGGTTT

CCGGTTCAGTATGAATTGTGAGCAGCCCCTGCGGCTATATCTACTTCGA

CGTATA

SEQ ID NO: 62
ACCAACAGGCAGAAGAGGCTTACAAAAATGCTCTAGATATCTATAATCG

CGCCGGTCTGGATAATAGGCGGGAAAAGTCAAATATTCTTATCGGACTT

GGCGATGCAGCTAGCGCACTGAGCAAATTTATAGACGCGAAAAATTTCT

ACAGTGAAGGTTTAGCAGTCCGAGCGCGGTCATGACGGTGCTTGCGGAC

TAGTGTCTGCTCGCAATTCAGAGCAGCCGCTTCGGCTGGTTCAGTTTGG

GTATGCCCTTTCTGTACCAGCCTGTGACTGGTCTGGTATGTAGCCCTTG

ACCAAT

SEQ ID NO: 63
ATGAAGCTCCGTCGTGTTTATGTAAAGAACGTTCGCAGTTTCTACGATG

CTGAAGAACTCATTCTGGACGGAGATATTTCTATTATTATAGGCCCAAA

TGGTGGAGGAAAAACAAATCTACTTGATGCGACGATACACTTGTTGAGA

AGACATTTATTGCAATCGTGGGCTGTCGTTCGCCATACATACACGCCAA

TAAACTATTCCGATCACTTCCAACCAAATGATCAAATCACAAACTATGC

GCTGGAGAAGTACAGCGGTCGCGAAAGCGAAGACCAAGTCGTTGAGTTC

GATATC

SEQ ID NO: 64
CGGGGGCGGTCTCCTCATATATGGAGGGAATTAATCTGAAGGGTCGGAG

CCCCCGCTACGGCACACACACGGCGGCGGGCGGTGGGCTCCTTCCTCAT

ATACGCTTCCTGATAATTTCGACCGTAATCGCCCGCCGGCCGAGCGGCC

-continued

```
AGACCTTATTAGTCCAGCATCACACGGTGCATCGTATCGTGGAGGGCGA

ACAACCGCCTAAGGTTCGCCACGTAGCCATCCACATCCGCCCTTGCCGC

TCGCGCAAGGGAAGCAGAATGCTTGATAGCGACTTCGCGGGCGTCTTTG

GTAGCC
```

SEQ ID NO: 65
```
TGTGGGCGCTCATGGAAACGGGGGACGTGCTTTTTTGATCTCTAGCCAT

TGTCATCATCCATCGGTCCGGGTGACAGGCCTTTACGCACATAACAACG

GTTATTTCGATCAGCCCCCTCCTGATCGCACAAGTCAGCTATACAGATG

CTTCTGAAAGCCAACAAAGGCGTTACGTATCTGCGTGACCCCACCGAGC

TGCGCTGCGGCATCGCTGACAGCTCTGTATTTTAATTCGAGGAGGTGGG

GCAATTTAGCCTGGTCAAGCTCGCCAACGTCTTCCTTCACATATTGAGA

CAGGAC
```

SEQ ID NO: 66
```
AGAGTGTATTTCCCCAAGACTTTATCTCTTTGCTCATCACAAAACAGCC

CGCTCAAGATGATATGCGCTGGGATTTGTGCCGCGACCCGTTGTAATTG

TATTTACCTCTCGGCTCATGTTCCCTGTCGCCGGAGCGATTGGAGGTAA

AGTAATCTCAACTTTGCGGCCCATGGCTGATGCTAGCTCAGCTACGCGA

CCTAAGGTAATATCTTTGTGTCCGCGGAGTTCGCGATGAATGACCGAGC

GATTGACGCCGATGGTGCGGGCAATATCGGCTTGAGTTAGACCGTTCTT

GGCTTC
```

SEQ ID NO: 67
```
ACCTGTCTCGACATCGGGGGCAGCCACGAGGCGTCGGCCGTGGTAGATC

TCGGCGAAGCGGTAGTAGTGGGCGAGGTCCCCATCGGGATCGATGGGGG

AGTCCGGCGTACCTTCTCCCTCTTCTGCGATTAGCGACAGGGCTCGCAT

GGCGCTGGGTGCGTCAGTGATGGCGAACAACCTACTATCGGGGAACCAC

CGCCTGTCGACGAGCTGGCGGTCCGGGTTTCCTTTGAAGACAGCGTCAC

CCAGCGCTTCGATCTTCTCAATCAAGGCTGCGTAGAACTGCCCGATGGT

CGCGAA
```

SEQ ID NO: 68
```
GACGTGGTGACGGTGGCACCAGTCGCCCAGCGAAGCGGCTACTGTACTG

AGCCCGCAGTCATGTCGGCTGAAGAAATGGTCGATATGCCCCAGGGAGG

TCGGGCGTAGGTCGTACCTCAAATTCACCGGCAGGATCTTGTCCAGCAA

GGCGTCCGAATTCGCATCGACCTGACTTAGGAAATTACCGAGGTAATCG

CTCGGTCCGTTCGCGTCGGCGGCCTGCATCGCCAGCAGCGCCTTATGCT

CGGTCGTCAACTCACGAGCGAATATTGTCCAGGACAGGTTGTCGACCTC

GGCGAC
```

SEQ ID NO: 69
```
GAGCATGGCAGGCCACCACGCATCGCTTCTTCATCACCTTGCTCGGACG

ACTTGCTGCTTTGTCGGTCTCTCTCTCAAGGACGAGACGCTGCGACACT

TGCTTCGTCAGAGTGCCAGGATTAATCCCGGTCAATACCACTACTACGT

CAGCTGGCGTGCGCCGGGCGGCACGAGGGACGTCGACGCGGAACGATTG
```

-continued

```
ATTCGAGACGCTAACTTTGACGTGTACAATTTAGTCACGCTTTTCCTTA

GCGACGCCGAGATAGCCTCGTTGGGCCGCTTGCTCACCGCCGATGCAGC

CGAGTT
```

SEQ ID NO: 70
```
AACGCGATGGGAGCAGCACGTAATGGGCGTCATACAAGATATAAAAGAA

GGACTTGAAGGTAGAATAGATAACCTTAAGGAAAATATTGATAATATCA

GTTCCAGTATCACATGCACAATACAAGGAGTGCCGAAGGTCGAGTCAGA

AAGAATTTTGGGATGTGCAAACGCTTCGTTTGACCAAATACAGAAAATG

TGGATGAATGGTCCTACGGATAGGGCTGCATTTCTCGACGCCGTGAAAA

GTTTGATAGACCGCAACGCAAGTAATGGAAAATTCGGAGTTCCAGGATC

ATATTG
```

SEQ ID NO: 71
```
TTTTCCTTTCGCGCCTATGACCTGAGTGCGGCCGAAGCTGTCCGCTTAT

TAGAGTTTTACAACCAGATGCGAGCGGCTTAGCTCTTCCTCCGTTATTA

AGCAGGGCGCCTCTTCTTAGGGGCGCCCCTTCATATTTAATCTTGTCTG

ATGTCTGGCGCCATATCAGACAAACATCAGCGTTGACCTTGATTTTGCA

TCTACATTAGGGTTGCTCCCAGAATGGAGCCGCCGATGTCCGTCCCGTA

CCTCAAGCGAGAGATGTGGGGTGTGTATTACATCCATTGGCGCGAGGGC

GGCCGC
```

SEQ ID NO: 72
```
GTTGGAGATGGTGCCGTTTGCAACCGTCAGATCGCCTACTGTGAATCCG

GTGACCTCCCGAGAGAACGTGAAGGTAACTGTCGTAGTCTCGCCAACTG

CCAAAGAGGTGTCCGCAACGGCGATGGTCGCTGTCGGGGCGCTTGTTTG

GACATCAACGGTGAGACCCGCCGAGGCAGGCCCCGTGTTACCAGCGGTA

TCGACGGCCCTAGCGGTGACCGTGTGCGATCCAGCCGTTAGCGTCGAAC

TGGTGATGCTATAGGTCCCGCCGATCGCCACTGCCGAGCCCAGAATGGT

CGTGCC
```

SEQ ID NO: 73
```
ACCGAAGGCGTCCCCGGACACGAAGGCCTGAAACACCATATCTGTGGCG

ATCAGGCCGACGTGGTCGCGGACTTCAACTGGCAGAGAATGCCAGGCCG

CTTCGATTTCAGATGATACTGGTACGGACATAGGAGCGGCTTAGCTTTC

TCAGTGCAAATGTGATTGATTCCGGCTCAAAAATGATCTTGATCGGACG

AGACGTTTTCAATCCATGTCGTGTTGCCATCGCCGATCGGTGCGTCAAG

AGACAGATGGCGCCGACCGTAGATACGCGTTCGGGTTGCCCGCACCGCT

TCTCCA
```

SEQ ID NO: 74
```
GGAGGTGTGATCTGATGATGTGCTGGATGAAATTGGCGGTCGAGCACTT

GTTCAGCTTGGCCAGCTCGACGAGATCGGCGTGATGCTCGGCGTCGATC

AGGATGTTCAGCGAGACCGGACGTACGCAGGACTTGGTATTAGCGCCGT

TGCGCATCAGCTTGCAGCCTTGCTCTGCTTCTCAGCGTGCCGCGTCAGG

ATGACCCTGATGTAGCTGTTGAGGTTGATGCCGTAATAGCCTGCGGACT

CTGTGAGATCCCGGCGAAGATCGTCGGCGAGGGTCAGGCGGATGGTGCT

GGTCGG
```

-continued

SEQ ID NO: 75

```
AAGTAACCGCTCAACATGATCTTCAGCATGTTGTCCAACAGCAGGAGAA

TACATGTAATTCACCATGACCGGCAAGCTGCGACTGGCCATTGCTTCCA

CCGCTTGAATGTAGCGATCGAATTTCGCAAAATCAGGGTGGAATGAAAA

TATCGAACCAAACTGCGAGCCTTGAATCCGTTCTGCAAAATTATCGAAA

AATTTTCTTGGCCGACTGCCGTTCGAAAACATTCTTACGTTTACATGCG

GCCCGCCTGAAACAAGACAGTCTACCAGCTCTGGGAAATGGGGGTGAAG

GGTCGG
```

REFERENCES

Green, P. N. 2005. *Methylobacterium*. In Brenner, D. J., N. R. Krieg, and J. T. Staley (eds.). "Bergey's Manual of Systematic Bacteriology. Volume two, The Proteobacteria. Part C, The alpha-, beta-, delta-, and epsilonproteobacteria." Second edition. Springer, New York. Pages 567-571.

Green, P. N. and Ardley, J. K. 2018. Review of the genus *Methylobacterium* and closely related organisms: a proposal that some *Methylobacterium* species be reclassified into a new genus, *Methylorubrum* gen. nov. Int J Syst Evol Microbiol. 2018 September; 68(9):2727-2748. doi: 10.1099/ijsem.0.002856.

Konstantinidis K. T., Ramette A., Tiedje J. M.: (2006). The bacterial species definition in the genomic era. Philos Trans R Soc Lond B Biol Sci 361: 1929-1940.

Lidstrom, M. E. 2006. Aerobic methylotrophic prokaryotes. In Dworkin, M., S. Falkow, E. Rosenberg, K.-H. Schleifer, and E. Stackebrandt (eds.). "The Prokaryotes. A Handbook on the Biology of Bacteria. Volume 2. Ecophysiology and biochemistry." Third edition. Springer, New York. Pages 618-634.

Sy, A., Giraud, E., Jourand, P., Garcia, N., Willems, A., De Lajudie, P., Prin, Y., Neyra, M., Gillis, M., Boivin-Masson, C., and Dreyfus, B. 2001. Methylotrophic *Methylobacterium* Bacteria Nodulate and Fix Nitrogen in Symbiosis with Legumes. Jour. Bacteriol. 183(1):214-220.

The breadth and scope of the present disclosure should not be limited by any of the above-described embodiments, but should be defined only in accordance with the following claims and their equivalents.

What is claimed is:

1. A method for mitigating methane gas in an agricultural field that comprises:
(a) applying a composition to a field, plant, plant part or seed, wherein the composition comprises at least one *Methylobacterium* comprising a soluble methane monooxygenase enzyme selected from the group consisting of NLS0737, NLS0770, NLS5278, NLS5334, NLS5480, NLS5549, and variants thereof; and,
(b) growing the *Methylobacterium* whereby the *Methylobacterium* uses methane as a carbon source;
wherein the use of the methane as the carbon source oxidizes methane and reduces methane emissions in the field.

2. The method of claim 1, wherein the plant, plant part, or seed is rice.

3. The method of claim 1, where the composition is applied to a flooded or irrigated rice field.

4. The method of claim 1, wherein application of the composition provides for increased yield of a crop grown in the agricultural field.

5. A method of claim 1, wherein the composition further comprises one or more second biological.

6. The method of claim 1, wherein the composition further comprises one or more obligate methanotroph.

7. The method of claim 1, wherein the composition further comprises a second Methylobacteria wherein the second Methylobacteria enhances growth, yield, nutrient update, or nitrogen use efficiency.

8. The method of claim 7 wherein the second Methylobacteria is selected from the group consisting of LGP2000 (NRRL B-50929), LGP2001 (NRRL B-50930), LGP2002 (NRRL B-50931), LGP2003 (NRRL B-50932), LGP2004 (NRRL B-50933), LGP2005 (NRRL B-50934), LGP2006 (NRRL B-50935), LGP2007 (NRRL B-50936), LGP2008 (NRRL B-50937), LGP2009 (NRRL B-50938), LGP2010 (NRRL B-50939), LGP2011 (NRRL B-50940), LGP2012 (NRRL B-50941), LGP2013 (NRRL B-50942), LGP2014 (NRRL B-67339), LGP2015 (NRRL B-67340), LGP2016 (NRRL B-67341), LGP2017 (NRRL B-67741), LGP2018 (NRRL B-67742), LGP2019 (NRRL B-67743), LGP2020 (NRRL B-67892), LGP2022 (NRRL B-68033), LGP2167 (NRRL B-67927), LGP2029 (NRRL B-68065), LGP2030 (NRRL B-68066), LGP2031 (NRRL B-68067), LGP2033 (NRRL B-68068), LGP2034 (NRRL B-68069), variants thereof, or a combination thereof.

9. A method for mitigating methane that comprises:
(a) treating pasture, wasteland, a landfill or waste, or land with livestock feed, with a composition comprising at least one *Methylobacterium* isolate; and
(b) growing the *Methylobacterium* in the pasture, wasteland, a landfill or waste, or land with livestock feed, thereby mitigating methane,
Wherein the *Methylobacterium* is selected from the group consisting of NLS0737, NLS0770, NLS5278, NLS5334, NLS5480, NLS5549, and variants thereof.

10. The method of claim 1, wherein the *Methylobacterium* is present in the composition at a concentration of from about $1\times10^3$ CFU to about $6\times10^{10}$ CFU.

11. A composition comprising a fermentation product comprising a *Methylobacterium* strain, wherein said fermentation product is essentially free of contaminating microorganisms, and wherein the *Methylobacterium* strain is selected from the group consisting of NLS0770, NLS0737, NLS5278, NLS5334, NLS5480, NLS5549, and variants thereof.

12. The composition of claim 11, wherein said composition further comprises a *Methylobacterium* selected from the group consisting of LGP2000 (NRRL B-50929), LGP2001 (NRRL B-50930), LGP2002 (NRRL B-50931), LGP2003

(NRRL B-50932), LGP2004 (NRRL B-50933), LGP2005
(NRRL B-50934), LGP2006 (NRRL B-50935), LGP2007
(NRRL B-50936), LGP2008 (NRRL B-50937), LGP2009
(NRRL B-50938), LGP2010 (NRRL B-50939), LGP2011
(NRRL B-50940), LGP2012 (NRRL B-50941), LGP2013
(NRRL B-50942), LGP2014 (NRRL B-67339), LGP2015
(NRRL B-67340), LGP2016 (NRRL B-67341), LGP2017
(NRRL B-67741), LGP2018 (NRRL B-67742), LGP2019
(NRRL B-67743), NLS0497 (NRRL B-67925), NLS0693
(NRRL B-67926), NLS1179 (NRRL B-67929), LGP2167
(NRRL B-67927), LGP2020 (NRRL-B-67892), LGP2021
(NRRL-B-68032), LGP2022 (NRRL-B-68033), LGP2023
(NRRL-B-68034), LGP2029 (NRRL B-68065), LGP2030
(NRRL B-68066), LGP2031 (NRRL B-68067), LGP2033
(NRRL B-68068), LGP2034 (NRRL B-68069), and variants
thereof.

13. The composition of claim 11, wherein said composition further comprises at least one additional component selected from the group consisting of an additional active ingredient, an agriculturally acceptable adjuvant, and an agriculturally acceptable excipient.

14. The composition of claim 11, wherein said *Methylobacterium* comprises a soluble methane monooxygenase.

15. The composition of claim 14, wherein the *Methylobacterium* comprises NLS0737 or NLS0770.

16. A plant, plant part or seed at least partially coated with the composition of claim 11.

17. The plant of claim 16, wherein said plant is a rice plant.

18. The composition of claim 11, which further comprises an obligate methanotroph.

\* \* \* \* \*

SEQUENCE LISTING

```
Sequence total quantity: 75
SEQ ID NO: 1            moltype = AA   length = 122
FEATURE                 Location/Qualifiers
source                  1..122
                        mol_type = protein
                        organism = Methylobacterium sp.
SEQUENCE: 1
MSTSQPTSQN TIFQKMDTMK FERTISHQCG VTMNDSVEAR AIAEYMSEKP DVTVTYQPAL  60
IRIDGVGKLT FLMDEISEIL GREMTAELFE VNASTHYGRM IRIDDNTVAL FGSMEEALEY  120
IE                                                                 122

SEQ ID NO: 2            moltype = AA   length = 356
FEATURE                 Location/Qualifiers
source                  1..356
                        mol_type = protein
                        organism = Methylobacterium sp.
SEQUENCE: 2
MSEQQTEVVK SGAAGSAVFA DSDSRKYRYF EPRGKRATHY EDVTVDVQPD PERYLKQDWI  60
ISFANGDGAY TKQSTAVKSS NWHAFRAPDQ EWERTHYQRQ SKIETMVQSV IANGRRAGAP  120
KAYDKAWVKV LQNHLGAWKH AEFGLGTSMM QAQRYGYTQM INNATLTNSS YKLRLAQDIT  180
LYLSEIGMDI QGFDDEAGKI RWLEDPIWQD TRLAIETIMG SSDYLEQYFA TNIVFEPLIG  240
ELFRSGFLMQ AASPNSDFIT PSVISAAEAD YERNLANTID LFHLLITDGE FASQNGALFQ  300
DWVTKHAALA HKAANTLQPI WSQPHAKPVQ FSDARASSLE RFSKILGELG LETPKE      356

SEQ ID NO: 3            moltype = AA   length = 126
FEATURE                 Location/Qualifiers
source                  1..126
                        mol_type = protein
                        organism = Methylobacterium sp.
SEQUENCE: 3
MSPLWSILHD FLSSGEDARD IHFFYGARTE KDLFYIDKFA AITAEYPRFK FIPVLSNADE  60
DTEWQGETGF VHQVVGTHLK RLDLGDDLDV YACGPTPMID ALTPVLFMND VDTDRIYYDR  120
FTPAPA                                                             126

SEQ ID NO: 4            moltype = AA   length = 556
FEATURE                 Location/Qualifiers
source                  1..556
                        mol_type = protein
                        organism = Methylobacterium sp.
SEQUENCE: 4
MSGALTLNKI TNQRGMPVGE AAKRIADLGW NPSYVQEAMT FPTDYKITKA PKDPMKQVLR  60
SYFPMQEEKD NRVYGALDAA LRGDMFRNVQ PRWVEWMKLF LAIIPFPEIS AARAMAMVGR  120
LAPGEELRTG FTMQMVDEFR HSTIQMNLKK WYMENYIDPA GFDITEEAFG KCYATTIGRQ  180
FGEGFITGDA ITSANMYLTV VAETAFTNTL FVAMPSEAAR NGDYALPTVF LSVQSDESRH  240
VGNGHSMLMA MLKEPDNHLL LERDLRYAFW QNHAIVDAAV GTFIEYGTTN RDKNKESYAE  300
MWHRWIFEDY YRTYMLPLEK YGIKVHHDDV QAAWDRLTKK FYVHAVAQFF SVGWPVNFWR  360
IEAQTEKDFE WFEHKYPGWY AQFGEYWKWY EKLSHKGQKV LLFNEDVGYV YPHRCWSSLV  420
```

-continued

```
PCLIREDIVV DEIDGKLHTF AHEIDRWTAV EAFSGEYQGR PTPAMGRFSG RREWEDCYHG    480
WDLADAIKDL GFVRTDGKTL VPQPHLRFDN KEMWTLDDVR GHTLQSPLQM LRAMTPSERD    540
AHLTQYRAGF SINPCN                                                    556

SEQ ID NO: 5               moltype = AA   length = 123
FEATURE                    Location/Qualifiers
source                     1..123
                           mol_type = protein
                           organism = Methylobacterium sp.
SEQUENCE: 5
MSVNARNASN QNIFQKMGDL SFDQTISHQC GVTMNDSVEA RAIAEFMGQK PGVTITHQPA    60
LIRIDGNGEL VFKMDEISEI LGKEMTAEIF EVNTSTHYGR MIRIDDNTVT LFGDMEAALQ    120
YIE                                                                  123

SEQ ID NO: 6               moltype = AA   length = 355
FEATURE                    Location/Qualifiers
source                     1..355
                           mol_type = protein
                           organism = Methylobacterium sp.
SEQUENCE: 6
MTLEAATRKS GAAGSAIFAD SDSRKYRYFE PKGKRATHYE DMTVDVQPDP ERYLLQNWII    60
SFADGKGAYS KENTAALSSD WHAFRAPDQE WERTHYQRQS KIEAMVQSVI ANGRKAGAPA    120
AFDKAWVKIL QNHLGAWKHV EFGLGTALMQ AQRYGYTQMI NNATLTNSSY KLRLAQDITL    180
YLAEIGMDIA GFDDTAGKRH WLEDGTWQGT REAVEAIMGS TDYLEQYFAT NIVFEPLVGE    240
LFRSGFLMQV ASSNGDFITP PVISAAEADY ERNLANAIDL FHLLATDAAH AEHNRTLFRS    300
WVDRHVALAR KAAADLQPIW SQPHSKPAQF ADAKAASTER VTKILGELGL DLPQE         355

SEQ ID NO: 7               moltype = AA   length = 345
FEATURE                    Location/Qualifiers
source                     1..345
                           mol_type = protein
                           organism = Methylobacterium sp.
SEQUENCE: 7
MSEVYTVKLN PVGVEFEVEE DETVLDAAFR QGIALPHGCK EGRCAACKCI VTDGEVEMLP    60
YSTFALNETE RDQNHVLLCR SLISSDIEVD LLNYDEELLS KSIPVRDLQG RVSRVSSLTH    120
DIRLLEIELD QPLKFWAGQY VDITLPGAEE ITRSFSMANP PSETQKLSFI IKKYPGGRFS    180
SRLDGELDVG TPVGVKGPYG TCFRRENRGG ALILVGGGSG MSPLWSILHD HIASGEERPV    240
HFFYGARTQT DLFYLDLFAE VARSNPRFTF IPVLSHASDD AAWQGERGFV HEVVNDHLRR    300
LAYGEDLDVY ACGPEPMIEA LTPVLQMNDV SSERIFFDKF TPART                    345

SEQ ID NO: 8               moltype = AA   length = 556
FEATURE                    Location/Qualifiers
source                     1..556
                           mol_type = protein
                           organism = Methylobacterium sp.
SEQUENCE: 8
MSGTLTLNKI TAQKGISVGE AAKKIADLGW NPSYVQEAMT FPTDYKITKA PKDPMKQVLR    60
SYFPMQEEKD NRVYGALDAA LRGDMFRNVE PRWVEWMKLF LAIIPFPEIS AARSMAMVGR    120
LAPGEELRTG FTMQMVDEFR HSTIQMNLKK WYMENYIDPA GFDITEEAFG KCYATTIGRQ    180
FGEGFITGDA ITSANIYLTV VAETAFTNTL FVAMPSEAAR NGDYALPTVF LSVQSDESRH    240
VGNGHSMLMS ILKEPENHLL LERDLRYAFW QNHAIVDAAI GTFIEYGTTN RDKDKESYAE    300
MWHRWIFEDY YRTYMLPLEK YGIKIHHDDV QTAWKRITEK HYVHKIAQFF SVGWPVNFWR    360
IEAQTEKDFE WFEHKYPGWY AQFGEYWKWY GKLSRPGQKI VTFNEDVGYV YPHRCWSSLV    420
PCVVREDLVT DEIDGQLHTF AHEIDRWTAV EAFANEYEGR PTPAMGRFSG RREWESVYHN    480
WDLADAYIKDL GFVRTDGKTL VPQPHLRFDN KDMWTLDDVR GYTLKSPLIT LREMSPEARE    540
AHLAEYRAGF TINPCN                                                    556

SEQ ID NO: 9               moltype = DNA   length = 369
FEATURE                    Location/Qualifiers
source                     1..369
                           mol_type = genomic DNA
                           organism = Methylobacterium sp.
SEQUENCE: 9
atgtcgacat cacaacccac atctcaaaat accatcttcc aaaagatgga caccatgaag    60
ttcgagcgga cgatctcgca tcagtgcggg gtcacaatga acgatagtgt tgaagctcgg    120
gcgatcgccg aatacatgtc ggagaagcca gatgtcactg tgacttatca acctgcgctc    180
atccgcatcg acggggttgg gaagcttacg ttcctgatgg acgagatcag tgagatcctc    240
ggccgagaga tgactgcgga gctttttcgag gtaaacgctt ctacgcacta cggtcgcatg    300
atccgcattg atgacaacac agttgcactg tttggcagca tggaagaggc gctcgaatac    360
atcgagtaa                                                            369

SEQ ID NO: 10              moltype = DNA   length = 1071
FEATURE                    Location/Qualifiers
source                     1..1071
                           mol_type = genomic DNA
                           organism = Methylobacterium sp.
SEQUENCE: 10
gtgagcgaac aacagaccga agtggtgaag tcaggagctg ccggctcagc cgtattcgca    60
gactctgaca gccgcaagta tcgttacttc gaaccgcgcg gcaagcgggc gacgcactat    120
```

```
gaagatgtga cagtcgatgt ccaacctgat cccgagcggt atctaaaaca ggattggatc    180
atctcctttg ccaatggcga cggagccttat acgaaacagt ctaccgccgt gaaaagttcc    240
aactggcatg cgttccgggc gccgaccaa gagtgggagc ggacccacta tcagcgtcag     300
tccaagatcg agacgatggt ccaatccgtt atcgccaacg gtcgaagagc tggagccccc    360
aaggcttacg acaaggcctg ggtgaaggtt ctgcagaacc atttgggtgc gtggaagcac    420
gccgaattcg gcctgggcac ctcgatgatg caggcccagc gctacggcta cactcaaatg    480
attaacaacg cgacgttgac gaactcgtcg tacaagcttc gtcttgcaca ggacatcacg    540
ctttacctct cggaaatcgg tatggatatc caggggtttg atgatgaggc cggcaagatt    600
aggtggctgg aggatccgat ctggcaggac acgcgcctcg ccatcgaaac tattatgggt    660
tcttccgact atttagagca gtactttgcg acgaacattg tcttcgaacc actaattgga    720
gagcttttcc gatcaggttt ccttatgcag gccgcatccc caaatagtga cttcattacc    780
ccgtcggtga tctcggccgc agaggccgat tacgagcgca atctcgccaa caccattgac    840
ctattccatc tgctcataac ggacggtgaa ttcgcatccc agaatggtgc gctgttccaa    900
gactgggtca cgaagcatgc ggcgctcgcg cacaaagctg ccaacacgct ccaacccatc    960
tggtcgcaac cccacgcgaa accggtccag ttttccgatg ccagggccag ctcattggag    1020
cggttcagca agatcctcgg cgaacttggc ctcgaaaccc ccaaggagtg a            1071
```

SEQ ID NO: 11        moltype = DNA    length = 381
FEATURE               Location/Qualifiers
source                1..381
                       mol_type = genomic DNA
                       organism = Methylobacterium sp.
SEQUENCE: 11

```
atgtcgccgc tgtggtcaat cctgcacgac ttcctctcgt ctggtgagga cgcgcgcgat    60
atccacttct tctatggcgc gcgcacggag aaagacctat tttacatcga taagttcgca    120
gcgatcacag ccgaataccc tcggttcaaa ttcatacccg tgctctctaa cgccggatgg    180
gacaccgagt ggcaagggga dacgggcttc gtccatcaag tcgttggaac acacctcaaa    240
cgccttgatc tcgcgatga tttagacgtc tacgcctgcg gtccgacacc gatgatcgac     300
gcgctaacac cggtgttgtt catgaacgac gttgacaccg accggatcta ctatgaccgg    360
tttacccctg cgccggcctg a                                              381
```

SEQ ID NO: 12        moltype = DNA    length = 1671
FEATURE               Location/Qualifiers
source                1..1671
                       mol_type = genomic DNA
                       organism = Methylobacterium sp.
SEQUENCE: 12

```
atgtcgggag cactaactct caacaagata acgaaccaac gtggcatgcc ggtgggcgag    60
gctgcgaagc gtattgcgga tcttgggtgg aacccgtcgt acgtccagga agccatgacg    120
tttcccacgg actacaagat cacgaaggcg ccgaaggacc cgatgaagca ggtccttcgg    180
tcatacttcc cgatgcaaga agagaaggac aaccgcgtat acggcgcact cgacgccgct    240
ttgcgcggcg acatgttccg caacgtgcag ccgcgttggg tcgagtggat gaagctgttc    300
ctggccatca tcccgttccc agagatctcg gctgcgcgcg cgatggccat ggtggggcgg    360
cttgctccgg gcgaagaact gcgtaccggc ttcaccatgc agatggtcga tgaattccgc    420
cattcgacca tccagatgaa cctcaaaaaa tggtatatgg agaattatat cgatccggcg    480
ggcttcgata ttaccgagga agcattcggc aagtgctacg ccacaactat cgggcgccag    540
ttcggtgagg gcttcatcac cggcgacgcg atcacctcag cgaacatgta cctgaccgtc    600
gtggccgaga cagcgttcac caacacgctg ttcgtcgcca tgccgtcgga ggccgctcgt    660
aacggagatt acgctctgcc gacggtgttc ctatccgtgc agtccgatga gagccggcac    720
gtgggtaacg gccactcgat gctgatggcg atgctcaagg agcccgacaa ccacctgctg    780
cttgagcgcg acctccgtta cgccttctgg cagaaccacg ccatcgtcga tgccggcgtt    840
ggcacgttca tcgagtacgg gaccacgaac cgcgataaga acaaagagtc ttacgcggaa    900
atgtggcacc gctggatctt cgaggactac taccgcacat acatgttgcc gctcgagaag    960
tacggcatca aggttcatca cgacgatgtt caggctgctt gggatcgctt gaccaagaag    1020
ttctacgtcc acgccgtcgc acagttcttt tccgtcggct ggccggtcaa tttctggcgc    1080
atcgaagccc agacggaaaa agacttcgag tggttcgagc ataagtaccc cggctggtac    1140
gcgcagtttg gcgagtactg gaagtggtac gagaagctgt cccacaaggg tcagaaggtt    1200
ctcctgttca atgaggatgt cggatacgtc tatccgcacc ggtgctggag ttctctggtg    1260
ccatgcctca tccgtgagga catcgtcgtc gacgagatcg atggcaagct gcacaccttc    1320
gctcatgaga tcgaccgttg gactgcagtg aagcccttct cgggcgaata ccaaggtagg    1380
ccgacacctg cgatgggccg cttcagcgga cgccgcgagt gggaagactg ctaccacggc    1440
tgggatcttg ccgacgcgat caaggatctc ggcttcgttc ggactgacgg caagacactc    1500
gtgccgcagc cgcatctgcg cttcgacaac aaggagatgt ggaccctcga cgatgttcgc    1560
gggcacaccc tccagagccc gttgcagatg ctgcgtgcga tgacgccatc cgagcgtgac    1620
gcacacctta cccaataccg ggctgggttc tcgatcaatc cttgcaactg a            1671
```

SEQ ID NO: 13        moltype = DNA    length = 372
FEATURE               Location/Qualifiers
source                1..372
                       mol_type = genomic DNA
                       organism = Methylobacterium sp.
SEQUENCE: 13

```
atgtctgtga atgcacgcaa tgcgtcgaac cagaacatct tccaaaagat gggggatctt    60
tctttcgatc agacgatctc acaccagtgc ggtgttacca tgaacgacag cgtcgaggcg    120
cgcgcgatcg ctgaattcat gggccagaag ccgggcgtca ccatcaccca ccagcctgcg    180
ctgatccgca tcgatggaaa cggcgaactc gtcttcaaga tggacgagat cagcgaaatt    240
ctcggcaaga agatgaccgc ggagatcttc gaggtcaaca cttcgacgca ctacggcagg    300
atgatccgca tcgacgacaa tacggtcacg ttgttcggcg atatggaagc tgctctgcag    360
tacatcgagt aa                                                        372
```

-continued

```
SEQ ID NO: 14            moltype = DNA   length = 1068
FEATURE                  Location/Qualifiers
source                   1..1068
                         mol_type = genomic DNA
                         organism = Methylobacterium sp.
SEQUENCE: 14
atgacgttgg aagccgccac acggaagtcg ggcgcagccg gctccgcgat tttcgcggac    60
tcggatagcc gcaagtaccg gtatttcgaa cccaagggca aacgtgcgac ccactacgaa   120
gacatgacgg tcgacgtaca gcccgatccc gagcgttacc tactccagaa ctggatcatt   180
tcgttcgcgg acgggaaggg cgcgtactcg aaggagaata cggcggccct gagctccgac   240
tggcacgctt ccgcgcgcc tgatcaggag tgggagcgca cgcattatca gcgacagtcg    300
aagatcgagg cgatggtgca atccgtgatc gccaatggtc gcaaggccgg cgctccggcc    360
gccttcgaca aggcctgggt gaagatcctc cagaaccatc tcggcgcatg gaagcatgtg   420
gaattcgggc tgggcaccgc gctcatgcag cgcgcagcgct acggctacac gcagatgatc    480
aacaacgcga ccctgacgaa ctcgtcctac aagctgcgcc tcgcccagga catcacgctc    540
tacctcgcgg agatcgggat ggacatcgcc gggttcgacg acacggcggg taagcggcac    600
tggctcgagg acggaacttg gcagggcacc cgggaagcgg tggaggccat catgggctcg    660
accgactacc tggagcagta cttcgcgacg aacatcgtct tcgagccgct ggtgggcgag    720
ctgtttcgca gcgcgcttcct gatgcaggtc gcgtcctcga acggggactt catcacgccg    780
ccggtgatct ccgcggccga ggcggactac gagcgcaacc tcgccaacgc gatcgacctg    840
tttcacctgc tcgccacgga cgccgcgcac gccgagcaca accggaccct gttccggagc    900
tgggtcgacc ggcacgtcgc tttggctcgc aaggcagctg ccgatctcca gccgatctgg    960
tcacagcctc attcgaagcc ggcccagttc gccgacgcga aagcggcgtc caccgaacgt   1020
gtcaccaaga tcctcggcga gctcggcctc gatcttcctc aggagtaa              1068

SEQ ID NO: 15            moltype = DNA   length = 1038
FEATURE                  Location/Qualifiers
source                   1..1038
                         mol_type = genomic DNA
                         organism = Methylobacterium sp.
SEQUENCE: 15
atgagcgagg tatacaccgt caaactcaac ccggtgggcg tcgagttcga ggtcgaggaa    60
gacgagaccg tcctcgacgc ggccttccgg cagggcattg cgctcccaca cggttgcaaa   120
gaggggcgtt gcgcggcttg caaatgcatc gtcaccgacg gcgaagtcga gatgctgccc    180
tattccacgt tcgcgctgaa cgagacggag cgtgaccaga accatgttct tctctgccgg    240
agccttatat cgagcgatat cgaggtcgac ctcctcaact acgacgagga gctgctctca    300
aaatcgatcc cggtccggga cctccaaggg cgtgtcagcc gcgtctcgag tctgacgcac    360
gacattcgcc tgcttgaaat cgaacttgat caacctctga agttctgggc tggacagtat   420
gtcgacatca cacttccggg agcagaggag attacgcgct cgtttttccat ggcaaatccg    480
ccgagcgaaa cgcaaaaact ctcgttcatc atcaaaaaat atcccggcgg ccgattctcc    540
tcccgcctcg acgagagct cgacgtcgga acccccgtcg gcgtcaaagg accctacgga    600
acctgcttcc gccgtgaaaa cagaggagga gccctaatcc tcgttggggg tggttcgggg    660
atgtcaccgc tctggtccat ccttcacgac cacatcgcga gcggagaaga acgcccagtc    720
catttcttct atggcgcgcg cacgcaaacg gatctgttct atctggatct gttcgccgag    780
gtggcgcggt ccaatccgcg cttcaccttc ataccggtcc tctcccacgc ttcggacgac    840
gccgcgtggc agggtgagcg ggggttcgtc cacgaggtcg tcaacgacca tctacgtcgt    900
ctcgcttacg gggaagatct cgacgtgtac gcctgcgggtc cggagccgat gatcgaggca    960
ctcacccccag tgctgcagat gaacgacgta tcttcggagc ggattttctt cgacaagttc   1020
acaccggcac ggacgtaa                                               1038

SEQ ID NO: 16            moltype = DNA   length = 1671
FEATURE                  Location/Qualifiers
source                   1..1671
                         mol_type = genomic DNA
                         organism = Methylobacterium sp.
SEQUENCE: 16
atgtctggaa cactgacact caacaagata acagcccaga aagggatctc cgtcggagag    60
gcggccaaga agatcgccga tctcggctgg aacccctcgt acgtccagga ggctatgacc   120
ttcccaacgg actacaagat caccaaggcc cccaaagatc cgatgaagca ggttctgcgg   180
tcctatttcc caatgcagga ggagaaggac aatcgggtct acggggcgct cgatgcggcg   240
ctgcgcggcg acatgttccg aaacgtcgag ccgcggtggg tcgagtggat gaagctcttc   300
ctggctatca ttccgtttcc cgagatttcg gccgcccgtt cgatgcgcat ggtcggtcgg   360
ttggcgcccg gcgaggagct gcgtaccggg tttaccatgc agatggtgca gcagttccgc   420
cactcgacca tccaaatgaa cctcaagaaa tggtacatgg agaactatat cgacccggcg   480
ggcttcgaca tcaccgaaga ggcgttcggc aaatgctatg cgacgacgat cggtcgtcaa   540
ttcggcgaag gtttcatcac cggcgacgcg atcacctcgg ccaacattta cctgaccgtg   600
gtcgccgaga ccgccttcac gaacacgctg ttcgtggcca tgccgtccga ggcgcgccgt   660
aacggcgact atgctctgcc gaccgtgttc ctgtcggtgc agtccgacga gagccggcac   720
gtcggcaacg ggcattcgat gctgatgtcg atcctgaaag agccggaaaa ccacctcctg   780
ctcgagcgcg acctcgcgcta cgccttctgg cagaaccacg ccatcgtcga tgccgcgatt   840
ggcacgttca tcgagtacgg caccacgaac cgtgacaagg acaaggagtc ctacgcggag   900
atgtggcacc gctggatttt cgaggactac tatcgcacct acatgctccc gctggagaaa   960
tacggcatca aaattcacca cgacgcgtt cagacggcat caccgagaaa              1020
cattacgttc acaagatcgc acagttcttc tccgtcggct ggccggtgaa tttctggcgg   1080
attgaggcgc agaccgagaa agacttcgag tggtttgagc acaaatatcc gggttggtac   1140
gctcagttcg gcgagtactg gaagtggtac ggaaagctga gccggcccgg ccagaagatc   1200
gtcaccttca cgaggatgt cggttacgtc tatccgcacc gctgctggag ttcgctggtg   1260
ccgtgcgtcg tgcgcgagga tctcgtcact gacgagatcg acggccagct gcacaccttc   1320
```

```
gcgcacgaga tcgatcgttg gaccgcggtc gaagccttcg ccaacgaata cgagggacgt   1380
cccacaccgg ccatggggcg gttcagcggc cgtcgtgaat gggagagtgt ataccacaac   1440
tgggatctgg cagatgccat caaggatctc ggcttcgtcc gcacagacgg caagaccctc   1500
gttcctcaac cgcatctgcg cttcgacaac aaggatatgt ggacgctcga cgatgtgcgt   1560
ggatacacgt gaagagccc gctgatcacc ttgcgcgaaa tgtcgccgga ggcgcgcgag   1620
gcgcatctcg ccgaatatcg cgcgggcttc acgatcaatc cctgcaactg a            1671
```

```
SEQ ID NO: 17           moltype = AA  length = 279
FEATURE                 Location/Qualifiers
source                  1..279
                        mol_type = protein
                        organism = synthetic construct
VARIANT                 1..63
                        note = X can be any amino acid or can be absent.
VARIANT                 70..77
                        note = X can be any amino acid or can be absent.
VARIANT                 79..80
                        note = X can be any amino acid or can be absent.
VARIANT                 105..135
                        note = X can be any amino acid or can be absent.
VARIANT                 141..151
                        note = X can be any amino acid or can be absent.
VARIANT                 153
                        note = X can be any amino acid or can be absent.
VARIANT                 155
                        note = X can be any amino acid or can be absent.
VARIANT                 158..159
                        note = X can be any amino acid or can be absent.
VARIANT                 163
                        note = X can be any amino acid or can be absent.
VARIANT                 166
                        note = X can be any amino acid or can be absent.
VARIANT                 174
                        note = X can be any amino acid or can be absent.
VARIANT                 179
                        note = X can be any amino acid or can be absent.
VARIANT                 189
                        note = X can be any amino acid or can be absent.
VARIANT                 195..216
                        note = X can be any amino acid or can be absent.
VARIANT                 222..230
                        note = X can be any amino acid or can be absent.
VARIANT                 233
                        note = X can be any amino acid or can be absent.
VARIANT                 236..240
                        note = X can be any amino acid or can be absent.
VARIANT                 242..279
                        note = X can be any amino acid or can be absent.
VARIANT                 67
                        note = X can be any amino acid or can be absent.
SEQUENCE: 17
XXXXXXXXXX XXXXXXXXX XXXXXXXXXX XXXXXXXXXX XXXXXXXXXX XXXXXXXXXX   60
XXXMPTXLPX XXXXXXXRXX PVRRLSWPDT ARFLILVARV RLLDXXXXXX XXXXXXXXXX   120
XXXXXXXXXX XXXXXLRLHA XXXXXXXXXX XVXRXGSXXA GDXLLXLMRR WLAXHEAIXA   180
LLPGVPEPXH VAQVXXXXXX XXXXXXXXXX XXXXXRAIL QXXXXXXXXX VPXSRXXXXX   240
PXXXXXXXXX XXXXXXXXXX XXXXXXXXXX XXXXXXXXX                          279
```

```
SEQ ID NO: 18           moltype = AA  length = 154
FEATURE                 Location/Qualifiers
source                  1..154
                        mol_type = protein
                        organism = synthetic construct
VARIANT                 1..7
                        note = X can be any amino acid or can be absent.
VARIANT                 9..10
                        note = X can be any amino acid or can be absent.
VARIANT                 19
                        note = X can be any amino acid or can be absent.
VARIANT                 52
                        note = X can be any amino acid or can be absent.
VARIANT                 71
                        note = X can be any amino acid or can be absent.
VARIANT                 74
                        note = X can be any amino acid or can be absent.
VARIANT                 94
                        note = X can be any amino acid or can be absent.
VARIANT                 96..154
                        note = X can be any amino acid or can be absent.
SEQUENCE: 18
```

-continued

```
XXXXXXXXMXX PLRRTVQVXE DGRMNLPADM RRVLGLTGAG RVILTQDEDG IXITTAEQAL  60
KRVRSLAAPF XRGXGSVVDE FIAERRADAA REDXEXXXXX XXXXXXXXXX XXXXXXXXXX  120
XXXXXXXXXX XXXXXXXXXX XXXXXXXXXX XXXX                              154

SEQ ID NO: 19          moltype = AA   length = 103
FEATURE                Location/Qualifiers
source                 1..103
                       mol_type = protein
                       organism = synthetic construct
VARIANT                2..29
                       note = X can be any amino acid or can be absent.
VARIANT                42
                       note = X can be any amino acid or can be absent.
VARIANT                69..72
                       note = X can be any amino acid or can be absent.
VARIANT                77..103
                       note = X can be any amino acid or can be absent.
SEQUENCE: 19
MXXXXXXXXX XXXXXXXXXX XXXXXXXXXP QSYALQILAI AXAMSVLGLG GVWIASRIYD  60
RNTRRLEAXX XXRRGDXXXX XXXXXXXXXX XXXXXXXXXX XXX                    103

SEQ ID NO: 20          moltype = AA   length = 2503
FEATURE                Location/Qualifiers
source                 1..2503
                       mol_type = protein
                       organism = synthetic construct
VARIANT                1..7
                       note = X can be any amino acid or can be absent.
VARIANT                12..27
                       note = X can be any amino acid or can be absent.
VARIANT                29..33
                       note = X can be any amino acid or can be absent.
VARIANT                39
                       note = X can be any amino acid or can be absent.
VARIANT                42
                       note = X can be any amino acid or can be absent.
VARIANT                46..47
                       note = X can be any amino acid or can be absent.
VARIANT                50
                       note = X can be any amino acid or can be absent.
VARIANT                58
                       note = X can be any amino acid or can be absent.
VARIANT                60
                       note = X can be any amino acid or can be absent.
VARIANT                62..63
                       note = X can be any amino acid or can be absent.
VARIANT                65
                       note = X can be any amino acid or can be absent.
VARIANT                71
                       note = X can be any amino acid or can be absent.
VARIANT                73
                       note = X can be any amino acid or can be absent.
VARIANT                75
                       note = X can be any amino acid or can be absent.
VARIANT                77
                       note = X can be any amino acid or can be absent.
VARIANT                79
                       note = X can be any amino acid or can be absent.
VARIANT                81
                       note = X can be any amino acid or can be absent.
VARIANT                87
                       note = X can be any amino acid or can be absent.
VARIANT                89
                       note = X can be any amino acid or can be absent.
VARIANT                92
                       note = X can be any amino acid or can be absent.
VARIANT                95..98
                       note = X can be any amino acid or can be absent.
VARIANT                101
                       note = X can be any amino acid or can be absent.
VARIANT                108
                       note = X can be any amino acid or can be absent.
VARIANT                112..116
                       note = X can be any amino acid or can be absent.
VARIANT                119..120
                       note = X can be any amino acid or can be absent.
VARIANT                123..126
                       note = X can be any amino acid or can be absent.
VARIANT                130
```

| | | |
|---|---|---|
| | | note = X can be any amino acid or can be absent. |
| VARIANT | 132..133 | |
| | | note = X can be any amino acid or can be absent. |
| VARIANT | 135..142 | |
| | | note = X can be any amino acid or can be absent. |
| VARIANT | 144 | |
| | | note = X can be any amino acid or can be absent. |
| VARIANT | 148..149 | |
| | | note = X can be any amino acid or can be absent. |
| VARIANT | 162..163 | |
| | | note = X can be any amino acid or can be absent. |
| VARIANT | 182 | |
| | | note = X can be any amino acid or can be absent. |
| VARIANT | 186 | |
| | | note = X can be any amino acid or can be absent. |
| VARIANT | 189 | |
| | | note = X can be any amino acid or can be absent. |
| VARIANT | 192 | |
| | | note = X can be any amino acid or can be absent. |
| VARIANT | 195 | |
| | | note = X can be any amino acid or can be absent. |
| VARIANT | 197 | |
| | | note = X can be any amino acid or can be absent. |
| VARIANT | 200..201 | |
| | | note = X can be any amino acid or can be absent. |
| VARIANT | 205 | |
| | | note = X can be any amino acid or can be absent. |
| VARIANT | 220 | |
| | | note = X can be any amino acid or can be absent. |
| VARIANT | 222..226 | |
| | | note = X can be any amino acid or can be absent. |
| VARIANT | 230..241 | |
| | | note = X can be any amino acid or can be absent. |
| VARIANT | 244..249 | |
| | | note = X can be any amino acid or can be absent. |
| VARIANT | 266 | |
| | | note = X can be any amino acid or can be absent. |
| VARIANT | 268..269 | |
| | | note = X can be any amino acid or can be absent. |
| VARIANT | 276 | |
| | | note = X can be any amino acid or can be absent. |
| VARIANT | 289 | |
| | | note = X can be any amino acid or can be absent. |
| VARIANT | 302..303 | |
| | | note = X can be any amino acid or can be absent. |
| VARIANT | 306 | |
| | | note = X can be any amino acid or can be absent. |
| VARIANT | 312 | |
| | | note = X can be any amino acid or can be absent. |
| VARIANT | 315..321 | |
| | | note = X can be any amino acid or can be absent. |
| VARIANT | 324 | |
| | | note = X can be any amino acid or can be absent. |
| VARIANT | 326 | |
| | | note = X can be any amino acid or can be absent. |
| VARIANT | 336..347 | |
| | | note = X can be any amino acid or can be absent. |
| VARIANT | 358..366 | |
| | | note = X can be any amino acid or can be absent. |
| VARIANT | 370..371 | |
| | | note = X can be any amino acid or can be absent. |
| VARIANT | 373..374 | |
| | | note = X can be any amino acid or can be absent. |
| VARIANT | 376..378 | |
| | | note = X can be any amino acid or can be absent. |
| VARIANT | 381..382 | |
| | | note = X can be any amino acid or can be absent. |
| VARIANT | 385 | |
| | | note = X can be any amino acid or can be absent. |
| VARIANT | 388 | |
| | | note = X can be any amino acid or can be absent. |
| VARIANT | 390 | |
| | | note = X can be any amino acid or can be absent. |
| VARIANT | 394 | |
| | | note = X can be any amino acid or can be absent. |
| VARIANT | 400 | |
| | | note = X can be any amino acid or can be absent. |
| VARIANT | 402..403 | |
| | | note = X can be any amino acid or can be absent. |

-continued

| VARIANT | 406 |
| | note = X can be any amino acid or can be absent. |
| VARIANT | 410 |
| | note = X can be any amino acid or can be absent. |
| VARIANT | 413..420 |
| | note = X can be any amino acid or can be absent. |
| VARIANT | 423..430 |
| | note = X can be any amino acid or can be absent. |
| VARIANT | 432..434 |
| | note = X can be any amino acid or can be absent. |
| VARIANT | 436 |
| | note = X can be any amino acid or can be absent. |
| VARIANT | 438..446 |
| | note = X can be any amino acid or can be absent. |
| VARIANT | 452 |
| | note = X can be any amino acid or can be absent. |
| VARIANT | 455..459 |
| | note = X can be any amino acid or can be absent. |
| VARIANT | 462..467 |
| | note = X can be any amino acid or can be absent. |
| VARIANT | 469..470 |
| | note = X can be any amino acid or can be absent. |
| VARIANT | 474 |
| | note = X can be any amino acid or can be absent. |
| VARIANT | 477 |
| | note = X can be any amino acid or can be absent. |
| VARIANT | 503 |
| | note = X can be any amino acid or can be absent. |
| VARIANT | 508 |
| | note = X can be any amino acid or can be absent. |
| VARIANT | 511 |
| | note = X can be any amino acid or can be absent. |
| VARIANT | 513 |
| | note = X can be any amino acid or can be absent. |
| VARIANT | 516..517 |
| | note = X can be any amino acid or can be absent. |
| VARIANT | 521..522 |
| | note = X can be any amino acid or can be absent. |
| VARIANT | 525..529 |
| | note = X can be any amino acid or can be absent. |
| VARIANT | 531..557 |
| | note = X can be any amino acid or can be absent. |
| VARIANT | 559..561 |
| | note = X can be any amino acid or can be absent. |
| VARIANT | 563 |
| | note = X can be any amino acid or can be absent. |
| VARIANT | 566..583 |
| | note = X can be any amino acid or can be absent. |
| VARIANT | 587 |
| | note = X can be any amino acid or can be absent. |
| VARIANT | 590 |
| | note = X can be any amino acid or can be absent. |
| VARIANT | 598..599 |
| | note = X can be any amino acid or can be absent. |
| VARIANT | 612 |
| | note = X can be any amino acid or can be absent. |
| VARIANT | 620..621 |
| | note = X can be any amino acid or can be absent. |
| VARIANT | 623..627 |
| | note = X can be any amino acid or can be absent. |
| VARIANT | 636 |
| | note = X can be any amino acid or can be absent. |
| VARIANT | 639 |
| | note = X can be any amino acid or can be absent. |
| VARIANT | 650..651 |
| | note = X can be any amino acid or can be absent. |
| VARIANT | 656 |
| | note = X can be any amino acid or can be absent. |
| VARIANT | 671 |
| | note = X can be any amino acid or can be absent. |
| VARIANT | 673 |
| | note = X can be any amino acid or can be absent. |
| VARIANT | 677..680 |
| | note = X can be any amino acid or can be absent. |
| VARIANT | 683 |
| | note = X can be any amino acid or can be absent. |
| VARIANT | 685 |
| | note = X can be any amino acid or can be absent. |
| VARIANT | 692 |

-continued

| | | |
|---|---|---|
| | | note = X can be any amino acid or can be absent. |
| VARIANT | 710..711 | |
| | | note = X can be any amino acid or can be absent. |
| VARIANT | 730 | |
| | | note = X can be any amino acid or can be absent. |
| VARIANT | 733 | |
| | | note = X can be any amino acid or can be absent. |
| VARIANT | 751 | |
| | | note = X can be any amino acid or can be absent. |
| VARIANT | 757..759 | |
| | | note = X can be any amino acid or can be absent. |
| VARIANT | 761 | |
| | | note = X can be any amino acid or can be absent. |
| VARIANT | 764 | |
| | | note = X can be any amino acid or can be absent. |
| VARIANT | 766 | |
| | | note = X can be any amino acid or can be absent. |
| VARIANT | 770 | |
| | | note = X can be any amino acid or can be absent. |
| VARIANT | 775..776 | |
| | | note = X can be any amino acid or can be absent. |
| VARIANT | 779..783 | |
| | | note = X can be any amino acid or can be absent. |
| VARIANT | 786 | |
| | | note = X can be any amino acid or can be absent. |
| VARIANT | 816..825 | |
| | | note = X can be any amino acid or can be absent. |
| VARIANT | 829 | |
| | | note = X can be any amino acid or can be absent. |
| VARIANT | 838..839 | |
| | | note = X can be any amino acid or can be absent. |
| VARIANT | 857..858 | |
| | | note = X can be any amino acid or can be absent. |
| VARIANT | 863..864 | |
| | | note = X can be any amino acid or can be absent. |
| VARIANT | 869..870 | |
| | | note = X can be any amino acid or can be absent. |
| VARIANT | 877 | |
| | | note = X can be any amino acid or can be absent. |
| VARIANT | 883 | |
| | | note = X can be any amino acid or can be absent. |
| VARIANT | 886 | |
| | | note = X can be any amino acid or can be absent. |
| VARIANT | 893..894 | |
| | | note = X can be any amino acid or can be absent. |
| VARIANT | 896..902 | |
| | | note = X can be any amino acid or can be absent. |
| VARIANT | 905 | |
| | | note = X can be any amino acid or can be absent. |
| VARIANT | 907..908 | |
| | | note = X can be any amino acid or can be absent. |
| VARIANT | 911..913 | |
| | | note = X can be any amino acid or can be absent. |
| VARIANT | 916 | |
| | | note = X can be any amino acid or can be absent. |
| VARIANT | 922 | |
| | | note = X can be any amino acid or can be absent. |
| VARIANT | 926..927 | |
| | | note = X can be any amino acid or can be absent. |
| VARIANT | 929 | |
| | | note = X can be any amino acid or can be absent. |
| VARIANT | 936 | |
| | | note = X can be any amino acid or can be absent. |
| VARIANT | 938 | |
| | | note = X can be any amino acid or can be absent. |
| VARIANT | 944..947 | |
| | | note = X can be any amino acid or can be absent. |
| VARIANT | 949..952 | |
| | | note = X can be any amino acid or can be absent. |
| VARIANT | 959..970 | |
| | | note = X can be any amino acid or can be absent. |
| VARIANT | 973..977 | |
| | | note = X can be any amino acid or can be absent. |
| VARIANT | 980 | |
| | | note = X can be any amino acid or can be absent. |
| VARIANT | 982 | |
| | | note = X can be any amino acid or can be absent. |
| VARIANT | 985..989 | |
| | | note = X can be any amino acid or can be absent. |

-continued

| VARIANT | 991..993 |
| | note = X can be any amino acid or can be absent. |
| VARIANT | 1006 |
| | note = X can be any amino acid or can be absent. |
| VARIANT | 1008..1009 |
| | note = X can be any amino acid or can be absent. |
| VARIANT | 1016 |
| | note = X can be any amino acid or can be absent. |
| VARIANT | 1019..1020 |
| | note = X can be any amino acid or can be absent. |
| VARIANT | 1023..1024 |
| | note = X can be any amino acid or can be absent. |
| VARIANT | 1026 |
| | note = X can be any amino acid or can be absent. |
| VARIANT | 1030..1034 |
| | note = X can be any amino acid or can be absent. |
| VARIANT | 1038..1039 |
| | note = X can be any amino acid or can be absent. |
| VARIANT | 1046..1047 |
| | note = X can be any amino acid or can be absent. |
| VARIANT | 1049..1050 |
| | note = X can be any amino acid or can be absent. |
| VARIANT | 1053 |
| | note = X can be any amino acid or can be absent. |
| VARIANT | 1055..1056 |
| | note = X can be any amino acid or can be absent. |
| VARIANT | 1058 |
| | note = X can be any amino acid or can be absent. |
| VARIANT | 1060..1061 |
| | note = X can be any amino acid or can be absent. |
| VARIANT | 1063..1065 |
| | note = X can be any amino acid or can be absent. |
| VARIANT | 1067 |
| | note = X can be any amino acid or can be absent. |
| VARIANT | 1069 |
| | note = X can be any amino acid or can be absent. |
| VARIANT | 1073 |
| | note = X can be any amino acid or can be absent. |
| VARIANT | 1076 |
| | note = X can be any amino acid or can be absent. |
| VARIANT | 1079..1080 |
| | note = X can be any amino acid or can be absent. |
| VARIANT | 1082..1084 |
| | note = X can be any amino acid or can be absent. |
| VARIANT | 1090 |
| | note = X can be any amino acid or can be absent. |
| VARIANT | 1093..1095 |
| | note = X can be any amino acid or can be absent. |
| VARIANT | 1097..1099 |
| | note = X can be any amino acid or can be absent. |
| VARIANT | 1103..1104 |
| | note = X can be any amino acid or can be absent. |
| VARIANT | 1107..1109 |
| | note = X can be any amino acid or can be absent. |
| VARIANT | 1111..1112 |
| | note = X can be any amino acid or can be absent. |
| VARIANT | 1114 |
| | note = X can be any amino acid or can be absent. |
| VARIANT | 1116..1118 |
| | note = X can be any amino acid or can be absent. |
| VARIANT | 1121..1122 |
| | note = X can be any amino acid or can be absent. |
| VARIANT | 1128..1129 |
| | note = X can be any amino acid or can be absent. |
| VARIANT | 1132 |
| | note = X can be any amino acid or can be absent. |
| VARIANT | 1136 |
| | note = X can be any amino acid or can be absent. |
| VARIANT | 1140 |
| | note = X can be any amino acid or can be absent. |
| VARIANT | 1143 |
| | note = X can be any amino acid or can be absent. |
| VARIANT | 1146..1148 |
| | note = X can be any amino acid or can be absent. |
| VARIANT | 1150 |
| | note = X can be any amino acid or can be absent. |
| VARIANT | 1156..1157 |
| | note = X can be any amino acid or can be absent. |
| VARIANT | 1159 |

-continued

```
                          note = X can be any amino acid or can be absent.
VARIANT                   1166..1167
                          note = X can be any amino acid or can be absent.
VARIANT                   1169
                          note = X can be any amino acid or can be absent.
VARIANT                   1172..1191
                          note = X can be any amino acid or can be absent.
VARIANT                   1193
                          note = X can be any amino acid or can be absent.
VARIANT                   1195..1197
                          note = X can be any amino acid or can be absent.
VARIANT                   1199
                          note = X can be any amino acid or can be absent.
VARIANT                   1202..1204
                          note = X can be any amino acid or can be absent.
VARIANT                   1206..1209
                          note = X can be any amino acid or can be absent.
VARIANT                   1214..1215
                          note = X can be any amino acid or can be absent.
VARIANT                   1218..1219
                          note = X can be any amino acid or can be absent.
VARIANT                   1221
                          note = X can be any amino acid or can be absent.
VARIANT                   1223
                          note = X can be any amino acid or can be absent.
VARIANT                   1228
                          note = X can be any amino acid or can be absent.
VARIANT                   1231..1232
                          note = X can be any amino acid or can be absent.
VARIANT                   1235..1236
                          note = X can be any amino acid or can be absent.
VARIANT                   1238
                          note = X can be any amino acid or can be absent.
VARIANT                   1241..1243
                          note = X can be any amino acid or can be absent.
VARIANT                   1245
                          note = X can be any amino acid or can be absent.
VARIANT                   1247
                          note = X can be any amino acid or can be absent.
VARIANT                   1250..1251
                          note = X can be any amino acid or can be absent.
VARIANT                   1253..1258
                          note = X can be any amino acid or can be absent.
VARIANT                   1261
                          note = X can be any amino acid or can be absent.
VARIANT                   1263..1265
                          note = X can be any amino acid or can be absent.
VARIANT                   1267..1277
                          note = X can be any amino acid or can be absent.
VARIANT                   1280
                          note = X can be any amino acid or can be absent.
VARIANT                   1283
                          note = X can be any amino acid or can be absent.
VARIANT                   1285..1287
                          note = X can be any amino acid or can be absent.
VARIANT                   1289..1291
                          note = X can be any amino acid or can be absent.
VARIANT                   1293..1294
                          note = X can be any amino acid or can be absent.
VARIANT                   1301
                          note = X can be any amino acid or can be absent.
VARIANT                   1305..1313
                          note = X can be any amino acid or can be absent.
VARIANT                   1319
                          note = X can be any amino acid or can be absent.
VARIANT                   1322..1325
                          note = X can be any amino acid or can be absent.
VARIANT                   1328..1329
                          note = X can be any amino acid or can be absent.
VARIANT                   1331..1452
                          note = X can be any amino acid or can be absent.
VARIANT                   1454
                          note = X can be any amino acid or can be absent.
VARIANT                   1457..1458
                          note = X can be any amino acid or can be absent.
VARIANT                   1464
                          note = X can be any amino acid or can be absent.
VARIANT                   1467..1469
                          note = X can be any amino acid or can be absent.
```

-continued

| | |
|---|---|
| VARIANT | 1471..1472 |
| | note = X can be any amino acid or can be absent. |
| VARIANT | 1476 |
| | note = X can be any amino acid or can be absent. |
| VARIANT | 1478 |
| | note = X can be any amino acid or can be absent. |
| VARIANT | 1482 |
| | note = X can be any amino acid or can be absent. |
| VARIANT | 1485..1486 |
| | note = X can be any amino acid or can be absent. |
| VARIANT | 1488 |
| | note = X can be any amino acid or can be absent. |
| VARIANT | 1493 |
| | note = X can be any amino acid or can be absent. |
| VARIANT | 1497 |
| | note = X can be any amino acid or can be absent. |
| VARIANT | 1501 |
| | note = X can be any amino acid or can be absent. |
| VARIANT | 1503 |
| | note = X can be any amino acid or can be absent. |
| VARIANT | 1505..1506 |
| | note = X can be any amino acid or can be absent. |
| VARIANT | 1508..1511 |
| | note = X can be any amino acid or can be absent. |
| VARIANT | 1515 |
| | note = X can be any amino acid or can be absent. |
| VARIANT | 1524..1526 |
| | note = X can be any amino acid or can be absent. |
| VARIANT | 1530..1531 |
| | note = X can be any amino acid or can be absent. |
| VARIANT | 1534..1538 |
| | note = X can be any amino acid or can be absent. |
| VARIANT | 1541 |
| | note = X can be any amino acid or can be absent. |
| VARIANT | 1550 |
| | note = X can be any amino acid or can be absent. |
| VARIANT | 1552..1553 |
| | note = X can be any amino acid or can be absent. |
| VARIANT | 1560 |
| | note = X can be any amino acid or can be absent. |
| VARIANT | 1563..1565 |
| | note = X can be any amino acid or can be absent. |
| VARIANT | 1570..1576 |
| | note = X can be any amino acid or can be absent. |
| VARIANT | 1583..1589 |
| | note = X can be any amino acid or can be absent. |
| VARIANT | 1591 |
| | note = X can be any amino acid or can be absent. |
| VARIANT | 1595 |
| | note = X can be any amino acid or can be absent. |
| VARIANT | 1604 |
| | note = X can be any amino acid or can be absent. |
| VARIANT | 1607..1611 |
| | note = X can be any amino acid or can be absent. |
| VARIANT | 1615 |
| | note = X can be any amino acid or can be absent. |
| VARIANT | 1625 |
| | note = X can be any amino acid or can be absent. |
| VARIANT | 1635..1637 |
| | note = X can be any amino acid or can be absent. |
| VARIANT | 1652 |
| | note = X can be any amino acid or can be absent. |
| VARIANT | 1654 |
| | note = X can be any amino acid or can be absent. |
| VARIANT | 1656 |
| | note = X can be any amino acid or can be absent. |
| VARIANT | 1708..1711 |
| | note = X can be any amino acid or can be absent. |
| VARIANT | 1714 |
| | note = X can be any amino acid or can be absent. |
| VARIANT | 1735 |
| | note = X can be any amino acid or can be absent. |
| VARIANT | 1737..1741 |
| | note = X can be any amino acid or can be absent. |
| VARIANT | 1757 |
| | note = X can be any amino acid or can be absent. |
| VARIANT | 1761 |
| | note = X can be any amino acid or can be absent. |
| VARIANT | 1763 |

-continued

```
                          note = X can be any amino acid or can be absent.
VARIANT                   1775
                          note = X can be any amino acid or can be absent.
VARIANT                   1781..1782
                          note = X can be any amino acid or can be absent.
VARIANT                   1784
                          note = X can be any amino acid or can be absent.
VARIANT                   1792..1793
                          note = X can be any amino acid or can be absent.
VARIANT                   1809
                          note = X can be any amino acid or can be absent.
VARIANT                   1812
                          note = X can be any amino acid or can be absent.
VARIANT                   1815..1823
                          note = X can be any amino acid or can be absent.
VARIANT                   1827
                          note = X can be any amino acid or can be absent.
VARIANT                   1829
                          note = X can be any amino acid or can be absent.
VARIANT                   1851
                          note = X can be any amino acid or can be absent.
VARIANT                   1855..1858
                          note = X can be any amino acid or can be absent.
VARIANT                   1863
                          note = X can be any amino acid or can be absent.
VARIANT                   1867..1869
                          note = X can be any amino acid or can be absent.
VARIANT                   1871
                          note = X can be any amino acid or can be absent.
VARIANT                   1881
                          note = X can be any amino acid or can be absent.
VARIANT                   1896
                          note = X can be any amino acid or can be absent.
VARIANT                   1899..1900
                          note = X can be any amino acid or can be absent.
VARIANT                   1902
                          note = X can be any amino acid or can be absent.
VARIANT                   1906..1909
                          note = X can be any amino acid or can be absent.
VARIANT                   1920..1922
                          note = X can be any amino acid or can be absent.
VARIANT                   1944
                          note = X can be any amino acid or can be absent.
VARIANT                   1952..1953
                          note = X can be any amino acid or can be absent.
VARIANT                   1965
                          note = X can be any amino acid or can be absent.
VARIANT                   1969..1970
                          note = X can be any amino acid or can be absent.
VARIANT                   1973
                          note = X can be any amino acid or can be absent.
VARIANT                   1976..1977
                          note = X can be any amino acid or can be absent.
VARIANT                   1979
                          note = X can be any amino acid or can be absent.
VARIANT                   1992
                          note = X can be any amino acid or can be absent.
VARIANT                   1997..2004
                          note = X can be any amino acid or can be absent.
VARIANT                   2007
                          note = X can be any amino acid or can be absent.
VARIANT                   2012
                          note = X can be any amino acid or can be absent.
VARIANT                   2014..2015
                          note = X can be any amino acid or can be absent.
VARIANT                   2021
                          note = X can be any amino acid or can be absent.
VARIANT                   2049..2051
                          note = X can be any amino acid or can be absent.
VARIANT                   2053
                          note = X can be any amino acid or can be absent.
VARIANT                   2066
                          note = X can be any amino acid or can be absent.
VARIANT                   2076
                          note = X can be any amino acid or can be absent.
VARIANT                   2085
                          note = X can be any amino acid or can be absent.
VARIANT                   2087
                          note = X can be any amino acid or can be absent.
```

-continued

| VARIANT | 2092 |
| | note = X can be any amino acid or can be absent. |
| VARIANT | 2096..2097 |
| | note = X can be any amino acid or can be absent. |
| VARIANT | 2100 |
| | note = X can be any amino acid or can be absent. |
| VARIANT | 2109..2165 |
| | note = X can be any amino acid or can be absent. |
| VARIANT | 2167..2178 |
| | note = X can be any amino acid or can be absent. |
| VARIANT | 2180..2186 |
| | note = X can be any amino acid or can be absent. |
| VARIANT | 2188..2191 |
| | note = X can be any amino acid or can be absent. |
| VARIANT | 2193..2209 |
| | note = X can be any amino acid or can be absent. |
| VARIANT | 2211..2212 |
| | note = X can be any amino acid or can be absent. |
| VARIANT | 2217..2218 |
| | note = X can be any amino acid or can be absent. |
| VARIANT | 2220..2222 |
| | note = X can be any amino acid or can be absent. |
| VARIANT | 2224..2225 |
| | note = X can be any amino acid or can be absent. |
| VARIANT | 2230..2231 |
| | note = X can be any amino acid or can be absent. |
| VARIANT | 2233..2235 |
| | note = X can be any amino acid or can be absent. |
| VARIANT | 2240 |
| | note = X can be any amino acid or can be absent. |
| VARIANT | 2242 |
| | note = X can be any amino acid or can be absent. |
| VARIANT | 2245..2246 |
| | note = X can be any amino acid or can be absent. |
| VARIANT | 2252 |
| | note = X can be any amino acid or can be absent. |
| VARIANT | 2256..2257 |
| | note = X can be any amino acid or can be absent. |
| VARIANT | 2260 |
| | note = X can be any amino acid or can be absent. |
| VARIANT | 2265..2266 |
| | note = X can be any amino acid or can be absent. |
| VARIANT | 2270..2271 |
| | note = X can be any amino acid or can be absent. |
| VARIANT | 2275..2276 |
| | note = X can be any amino acid or can be absent. |
| VARIANT | 2278..2279 |
| | note = X can be any amino acid or can be absent. |
| VARIANT | 2283..2286 |
| | note = X can be any amino acid or can be absent. |
| VARIANT | 2288 |
| | note = X can be any amino acid or can be absent. |
| VARIANT | 2290..2291 |
| | note = X can be any amino acid or can be absent. |
| VARIANT | 2298 |
| | note = X can be any amino acid or can be absent. |
| VARIANT | 2300..2301 |
| | note = X can be any amino acid or can be absent. |
| VARIANT | 2303..2308 |
| | note = X can be any amino acid or can be absent. |
| VARIANT | 2313..2322 |
| | note = X can be any amino acid or can be absent. |
| VARIANT | 2325..2327 |
| | note = X can be any amino acid or can be absent. |
| VARIANT | 2329 |
| | note = X can be any amino acid or can be absent. |
| VARIANT | 2332 |
| | note = X can be any amino acid or can be absent. |
| VARIANT | 2335 |
| | note = X can be any amino acid or can be absent. |
| VARIANT | 2340 |
| | note = X can be any amino acid or can be absent. |
| VARIANT | 2342..2353 |
| | note = X can be any amino acid or can be absent. |
| VARIANT | 2356 |
| | note = X can be any amino acid or can be absent. |
| VARIANT | 2359..2367 |
| | note = X can be any amino acid or can be absent. |
| VARIANT | 2370 |

```
                          note = X can be any amino acid or can be absent.
VARIANT                   2373..2374
                          note = X can be any amino acid or can be absent.
VARIANT                   2376..2406
                          note = X can be any amino acid or can be absent.
VARIANT                   2414
                          note = X can be any amino acid or can be absent.
VARIANT                   2416
                          note = X can be any amino acid or can be absent.
VARIANT                   2418
                          note = X can be any amino acid or can be absent.
VARIANT                   2423..2503
                          note = X can be any amino acid or can be absent.
VARIANT                   954
                          note = X can be any amino acid or can be absent.
VARIANT                   956
                          note = X can be any amino acid or can be absent.
VARIANT                   996
                          note = X can be any amino acid or can be absent.
VARIANT                   998
                          note = X can be any amino acid or can be absent.
SEQUENCE: 20
XXXXXXXDTL EXXXXXXXXX XXXXXXXRXX XXXLACTVXD HXSIAXXQNX VPIIRDIXLX    60
NXXDXDLADV XLXIXAXPXL XRPLTLXIXR IXAGXXXXID XPDLRIDXAI LXXXXXAGXX   120
ESXXXXVTLX LXXSXXXXXX XXEXAREXXD LRLLPPSHWG GXXAAPELLA AFVRPNDPAV   180
DXILRXAAXI LXRAXRXTAX XDGYXSGRKA RAWEMAEAIX AXXXXXAMAX XXXXXXXXXX   240
XRIXXXXXXY VLPPASFERS GQKVRXPXXI VERRLXTCLD LTLLWAACXE QAGLNPLLVL   300
TXXHAXLGLW LXDEXXXXXX XDDXQXLRKR RDLQEXXXXX XXXXXXXLIL IETTILTXXX   360
XXXXXXDPPX XFXXAXXXGA XXIDXDAXAX LEMXLDLRRX RXXGIXPLDX GEXXXXXXXX   420
APXXXXXXXX LXXXQXLXXX XXXXXXAPPS FXEDXXXXXI DXXXXXXPXX RLEXWKXRLL   480
DLTLRNKLLN FKPGKGSLTL DCXEPGAXED XLXAGXXFRL XXRPXXXXXD XXXXXXXXXX   540
XXXXXXXXXX XXXXXXAXX XRXEIXXXXX XXXXXXXXXX XXXELEXRLX DLFRLARXXF   600
EEGGANVLFL AXGFLTWTRX XGXXXXXRAP LLLVPXALXR ASVRAGFRLX XHDEEXRLNP   660
TLLEMLRQDF XLXMPDXXXX LPXDXSGIDV EXIWRIVRTH IRDLKGWEVX XEVVLSAFSF   720
TKFLMWKDLX ERXDLLKRSP VVRHLLDTPK XAYGDGXXXT XFPXPXRLDX EHPPXXIFXX   780
XXXPLXADSS QLSAILAAAS GKDFVLFGPP GTGKSXXXXX XXXXXQTIXN MIAQCLAXXG   840
RTVLFVSQKS AALEVVXXRR RLXXVGLGXX CLEVHAXKAQ KTXVIXQLRE AWXXRXXXXX   900
XXWDXAXXDL XXXREXLNGV VXSLHXXRXN GLSAHXAXGR VIAXXXXGXX XXLXLXWPXX   960
XXXXXXXXXX SLXXXXXRAX CXELXXXXXL XXXVGXIXDH PLRGIXAXXW SPLWRXEMXX  1020
AIXXLXRTLX XXXXSGQXXA EAMGLXXLXX TYXGXXRXLX XLXXXLXRXE ARXGLXFLXX  1080
GXXXLRQAVX ARXXXQXXXA RLXXRLXXXY XXPXVXXXDL XXLLAEWXXA KXSNFXLRGX  1140
RLXRVXXXLX PFAQGXXPXD IGPDLXXLXE IXXXXXXXXX XXXXXXXXXX XVXEXXXAXL  1200
GXXXPXXXXW SDPXXPAXXF XAXMAWAXRL XXVIXXMXPL XXXGXDXVRX XLXXXXXXLD  1260
XEXXXLXXXX XXXXXXXGGX LAXAXXXFXX XRXXAVKAIE XLGRXXXXXX XXXLAGRAXP  1320
DXXXXPVXXE XXXXXXXXXX XXXXXXXXXX XXXXXXXXXX XXXXXXXXXX XXXXXXXXXX  1380
XXXXXXXXXX XXXXXXXXXX XXXXXXXXX XXXXXXXXXX XXXXXXXXXX XXXXXXXXXX  1440
XXXXXXXXXX XXDXWVXXTL AVAXRWXXXL XXKAQXWXAW QXAAXXAXKA GLXPLVXAIE  1500
XGXIXXDXXX XAFEXAYARW WIDXXXTDDX XLRXXXXXFM XQRHEEAIRX FXXADSRLSX  1560
LAXXXVRARX XXXXXXIGGG VPXXXXXXXA XAFGXDPEWG TLAXEIXXXX XTKRXRHMPL  1620
RQLFXRMPNA LTRLXXXTPC LMMSPLSIAQ YXPXEXKPFD IVIFDEASQI APWDAIGAIA  1680
RGRQVVIVGD PEQLPPTNVG DRGVDEIXXX XDGXDVADQE SILDECLAAN LPQRXLXXXX  1740
XWHYRSRHES LIAFSNXHYY XGXLVTFPSP VTDDXRAVRL XXVXDGLYER GXXRVNRPEA  1800
RALVAEVVXR LXDPXXXXXX XXXAFAXEXR SLGIVTFNGE QQRLIENLLD XERRXXXXPE  1860
LEXFFDXXXW XEPVFVKNLE XVQGDERDAI LFSVAXGPXX DXTGRXXXXI SSLNREGGHX  1920
XXRRLNVAIT RARRELVVFA SMRXDQVDLG RXXARGVRDF KHFLXFAEXX GAXALXXAXA  1980
PTGGDIESPF EXAVMAXXXX XXXXALXARG WXIXXQVGVS XFRIDLGIVH PDAPGRYLAG  2040
VECDGATYXX XHXAATARDR DRLREXVLTD LGWRIXRVWS TDWWXDXQGA LXRLDXXLRX  2100
DLDADRAKXX XXXXXXXXXX XXXXXXXXXX XXXXXXXXXX XXXXXXXXXX XXXXXXXXXX  2160
XXXXXPXXXX XXXXXXXXPX XXXXXXQXXX XPXXXXXXXX XXXXXXXXXY XXADLSXXGX  2220
XXDXXRFHDX XYXXXLAAMX AXVVXXEGPV FXDILXXRLX RAHGXXRITX XLRQXXLXXV  2280
DPXXXXTXEX XRIVLWPXGX XPXXXXXXFR PAXXXXXXXX XXRAXXXDXP LXELXGLARX  2340
LXXXXXXXXX XXXMAXRLXX XXXXXXXGLX RMXXAXXXXX XXXXXXXXXX XXXXXXXXXX  2400
XXXXXXRARF AEAXAXLXAR ESXXXXXXXX XXXXXXXXXX XXXXXXXXXX XXXXXXXXXX  2460
XXXXXXXXXX XXXXXXXXXX XXXXXXXXX XXXXXXXXXX XXX                    2503

SEQ ID NO: 21            moltype = AA  length = 409
FEATURE                  Location/Qualifiers
source                   1..409
                         mol_type = protein
                         organism = synthetic construct
VARIANT                  1..84
                         note = X can be any amino acid or can be absent.
VARIANT                  105
                         note = X can be any amino acid or can be absent.
VARIANT                  115
                         note = X can be any amino acid or can be absent.
VARIANT                  130
                         note = X can be any amino acid or can be absent.
VARIANT                  132
```

-continued

```
                         note = X can be any amino acid or can be absent.
VARIANT                  143..144
                         note = X can be any amino acid or can be absent.
VARIANT                  153..159
                         note = X can be any amino acid or can be absent.
VARIANT                  173..208
                         note = X can be any amino acid or can be absent.
VARIANT                  220..226
                         note = X can be any amino acid or can be absent.
VARIANT                  238..247
                         note = X can be any amino acid or can be absent.
VARIANT                  260
                         note = X can be any amino acid or can be absent.
VARIANT                  267..269
                         note = X can be any amino acid or can be absent.
VARIANT                  285
                         note = X can be any amino acid or can be absent.
VARIANT                  298
                         note = X can be any amino acid or can be absent.
VARIANT                  300..301
                         note = X can be any amino acid or can be absent.
VARIANT                  303
                         note = X can be any amino acid or can be absent.
VARIANT                  305..306
                         note = X can be any amino acid or can be absent.
VARIANT                  320..322
                         note = X can be any amino acid or can be absent.
VARIANT                  324
                         note = X can be any amino acid or can be absent.
VARIANT                  327..328
                         note = X can be any amino acid or can be absent.
VARIANT                  330
                         note = X can be any amino acid or can be absent.
VARIANT                  333..335
                         note = X can be any amino acid or can be absent.
VARIANT                  349
                         note = X can be any amino acid or can be absent.
VARIANT                  368..382
                         note = X can be any amino acid or can be absent.
VARIANT                  386..409
                         note = X can be any amino acid or can be absent.
VARIANT                  117
                         note = X can be any amino acid or can be absent.
SEQUENCE: 21
XXXXXXXXX XXXXXXXXX XXXXXXXXX XXXXXXXXX XXXXXXXXX XXXXXXXXX    60
XXXXXXXXXX XXXXXXXXX XXXXMQTILY ARVSTADQTI AHQRXQAEAA GFKIXDXVVA   120
DEGVSGVSTX LXDRPQGRRL FDXXMLRRGD VLXXXXXXXV VRWVDRLGRN YAXXXXXXXX   180
XXXXXXXXXX XXXXXXXXX XXXXXXXXDV TETIREFMRX XXXXXXRGVI VRTVINNXXX   240
XXXXXXXMTF DGATTDPMQX AVRDALXXXI GFMAATAQAQ AEATXKEAQK AGIEHAKXRX   300
XEXDXXAYRG RKPSYTREQX XXDXVRXXLX QGXXXVSAIA KATGLSRQXT VYRIRDNPAE   360
AEAALARXXX XXXXXXXXXX XXWAAXXXXX XXXXXXXXXX XXXXXXXXX            409

SEQ ID NO: 22            moltype = AA   length = 218
FEATURE                  Location/Qualifiers
source                   1..218
                         mol_type = protein
                         organism = synthetic construct
VARIANT                  2..19
                         note = X can be any amino acid or can be absent.
VARIANT                  23
                         note = X can be any amino acid or can be absent.
VARIANT                  25..26
                         note = X can be any amino acid or can be absent.
VARIANT                  47
                         note = X can be any amino acid or can be absent.
VARIANT                  51..54
                         note = X can be any amino acid or can be absent.
VARIANT                  56..60
                         note = X can be any amino acid or can be absent.
VARIANT                  62
                         note = X can be any amino acid or can be absent.
VARIANT                  74..130
                         note = X can be any amino acid or can be absent.
VARIANT                  136..140
                         note = X can be any amino acid or can be absent.
VARIANT                  144..145
                         note = X can be any amino acid or can be absent.
VARIANT                  147..161
                         note = X can be any amino acid or can be absent.
```

```
VARIANT                    163
                           note = X can be any amino acid or can be absent.
VARIANT                    166..218
                           note = X can be any amino acid or can be absent.
SEQUENCE: 22
MXXXXXXXXX XXXXXXXXXY DDXIXXADAA AGEERDAIMR ALAEDMXEAS XXXXRXXXXX  60
GXFVRAERPA DLAXXXXXXX XXXXXXXXXX XXXXXXXXXX XXXXXXXXXX XXXXXXXXXX  120
XXXXXXXXXX RALGRXXXXX DRRXXQXXXX XXXXXXXXXX XRXASXXXXX XXXXXXXXXX  180
XXXXXXXXXX XXXXXXXXXX XXXXXXXXXX XXXXXXXX                          218

SEQ ID NO: 23              moltype = AA  length = 77
FEATURE                    Location/Qualifiers
source                     1..77
                           mol_type = protein
                           organism = synthetic construct
VARIANT                    1..17
                           note = X can be any amino acid or can be absent.
VARIANT                    21..22
                           note = X can be any amino acid or can be absent.
VARIANT                    40
                           note = X can be any amino acid or can be absent.
VARIANT                    50..51
                           note = X can be any amino acid or can be absent.
VARIANT                    67
                           note = X can be any amino acid or can be absent.
VARIANT                    72..73
                           note = X can be any amino acid or can be absent.
SEQUENCE: 23
XXXXXXXXXX XXXXXXMPV XXGIGIGRGD PLRPAVTRTX RFSGPEGFHX XPGALWLAAA   60
APLLATXLLL LXXRLAA                                                 77

SEQ ID NO: 24              moltype = AA  length = 101
FEATURE                    Location/Qualifiers
source                     1..101
                           mol_type = protein
                           organism = Methylobacterium sp.
SEQUENCE: 24
MPTAIPIRPA PERCLSWPDT ARLLILVARV RILDLEMHTV VRHGSGFADD RLLHLMRRWL  60
AQHEAISALL PGVAEPRHVA EVRAILQVPN SRPEPEDRRA L                      101

SEQ ID NO: 25              moltype = AA  length = 83
FEATURE                    Location/Qualifiers
source                     1..83
                           mol_type = protein
                           organism = Methylobacterium sp.
SEQUENCE: 25
MPQRRTIQVT EDGRMNLPAD IRRVLGLNGA GRIVLMQDED GIHLTTAEDP LRRVRELAAP  60
FRRGSGSVVD EFIAERRADS GED                                          83

SEQ ID NO: 26              moltype = AA  length = 48
FEATURE                    Location/Qualifiers
source                     1..48
                           mol_type = protein
                           organism = Methylobacterium sp.
SEQUENCE: 26
MPLDYALQIT AIAFGLSVLG LGGAFIASRV YDRNTRRYDE AAQLHKAD               48

SEQ ID NO: 27              moltype = AA  length = 1982
FEATURE                    Location/Qualifiers
source                     1..1982
                           mol_type = protein
                           organism = Methylobacterium sp.
SEQUENCE: 27
VQDGIQITCS VTEHVSLAYH ENAVPVIREV VVENTSEQEL SDVRVRIESR PAVVQPLTLR  60
IDRIPAGSNH HIELPDVRLD AALLAGFTEA SRLELTVIVE DAAGERARHL EELRVLPPSH  120
WGGGRSAPEL LAAFVRPNDP AVDVVLRDAA TKLGEAGRET GLNGYTTAKK SRAWELAEAI  180
WAAIADRRIA YVLPPASFER AGQKVRGPSD VLERKVGTCL DLSLLYAACL EQAGLNPVLV  240
LTVGHAFVGV WLQDDDFASA TVDDMQLLRK RRDLQDLVVP ETTLLTPEPP ATFKVATTQG  300
GVQVEDEAPA ALEIAIDVRR CRRRGIRPMD LGDGKPTGIA PAPTIPLNQT LSAPPSFEEE  360
ARAPVDEAPE TPVGRVERWK RKLLDLTLRN KLLNFKPGKG SVSLECASPG ALEDGLAAGT  420
EYRLKPLSDV LTGSDERSAD LYARRHHDDG RRSYLEAALA RKEIYTTSTE ADLDRRLLDL  480
YRLARNGFEE GGANILFLAV GFLSWTKKEG EAAYRAPLLL VPVTLKRSSV RAGFKLALHD  540
DEVRINPTLL EMLREDFKLR MPELEGDLPR DGSGYDVDGI FRIVRQHVKE LRGWEVVPDV  600
VLSAFSFTKY LMWKDLVDRA EVLKRNPVVR HLIDTPKHSY GDGTPFPEPT RLDREHPPET  660
VFAPLSADSS QLSAVLAAAG GKDFVLFGPP GTGKSQTIGN MIAQCLAQGR TVLFVSQKTA  720
ALEVVQRRLQ EIGLGDYCLE VHSTKAQKSA VLGQLRRAWH ERSTPSQGTW DAATSELASL  780
REELNGLVNA LHRRRENGLS AYEAFGRVIA SGGEAPLVLT WPDHLAHNET TLANLRAACR  840
ELRPVLASVG SLVDHPLQGV EATQWSPVWR DDMGAAIRAV EQTLGALRVS GQAFAEAIGL  900
PSLLATYAGT RGLVVLGNYL VRSEARCGAA FLADGAGDLR RAVAARERFQ TTKVQLLGRL  960
```

-continued

```
TGRYRPGILD QNLGALLAEW VAAQGANFLV KGGGKLKKVSA QVQPYAEGPL PPDLGPDLTG   1020
LIEVARHVKA GCLEELILAR LGLPWSNPDC PASEFASAIT WAEKVEQLLD ILGPLSLGID   1080
GLRDHLVHLV ERQGRALADG GRIAQTYAAF AQDRARANEA MKALGVLAGR PDPEEPLAAE   1140
ADWIERSCTI ARRLSSGLSR AQGWCAWQAA AQSALKTGLA PLIDALEDGR IAPDRAEIAF   1200
EIAYARWWID RVVSDDPVLR RFLPARHEDA IQRFRAADAR VTELSKQVVR SRLGGGIPGA   1260
TAFGADPEWG TLSHELTKKT AHMPLRKLFG KMPTALTKLT PCVMMSPLSI AQYLPPDKEP   1320
FDVVIFDEAS QISPWDAIGA LARAKQVVIV GDPEQLPPTN VGDRGVDDIE DGSDVTDQES   1380
ILDECLAANI PRRNLDWHYR SRHESLIAFS NSRYYGGRLV TFPSPVTDDR AVRLTLVPDG   1440
VYKRGSGRVN RPEARAVVAD IVRRLRDPSF SEERRSLGVV TFNGEQQRLI ENLLDEQRRS   1500
YPELEPFFDR DRWHEPVFVK NLENVQGDER DAIIFSVAVG PDQTGRPVST VSSLNKDGGH   1560
RRLNVAITRA RRELVVFASM RPEQIDLGRT RARGVRDFKH FLEFAERGAR ALAEAFAPTG   1620
GDVESPFEAA VMAGLEARGW TVHTQIGVSG FRIDLGIVHP DAPGRYLAGV ECDGATYHSS   1680
ATARDRDRLR EHVLTDLGWR IRRVWSTEWW MDAEGALTKL DQRLIEDLEA DRAKAAAAAA   1740
EAPRDVAVEP EAVEQEHDEP TGEPEVTPPV DTGPSEPAND LEPVTDLIPQ RLYADQALPV   1800
TPPAPKPEVY DDVRAYRIVD LNDLGRSVEP GRFYDASYQQ ALSAMVDHVL AVEGPIYEEL   1860
LIKRIARAHD IQRVGPLVRE AIADRIDASV ARTEDDGRPV LWPRGEEPRA SYPHRPASAA   1920
IRSHTDTPMP ELVGIAMTLP SNASEAERAR MIGQRLGLSR IEASARARFE RASELARQAA   1980
VA                                                                 1982

SEQ ID NO: 28              moltype = AA   length = 210
FEATURE                    Location/Qualifiers
source                     1..210
                           mol_type = protein
                           organism = Methylobacterium sp.
SEQUENCE: 28
MSVVLYARVS TAEQTLEHQQ TQAEAAGFVF DAVVADHGES GRKPLRDRPE GRRLYDMLRT   60
GDVLVVRWIN RLGRSYEDVT GVMRELMQRG VIVRTIISNM TFDGATKDPM QRAIRDALIA   120
FMAAAGEAEL EATREAQKAG IEHARKQADQ TAYRGRKPSY TRDQLTVISG MLGRGAGVSA   180
IAAETGLSRQ TIYRVQADPV EAEAALARWA                                   210

SEQ ID NO: 29              moltype = AA   length = 69
FEATURE                    Location/Qualifiers
source                     1..69
                           mol_type = protein
                           organism = Methylobacterium sp.
SEQUENCE: 29
MLSLDDIAAA AAGEERDALW RSLVEDMEEA AGRRRGGRGL VQADRPADLA RALGRDRRVQ   60
PSRLARSAS                                                          69

SEQ ID NO: 30              moltype = AA   length = 54
FEATURE                    Location/Qualifiers
source                     1..54
                           mol_type = protein
                           organism = Methylobacterium sp.
SEQUENCE: 30
MPVGIGIGRG DPLRPAVTRT ARFSGPEGFH PGALWLAAAS PLLATLLLLV RLAA         54

SEQ ID NO: 31              moltype = DNA   length = 300
FEATURE                    Location/Qualifiers
source                     1..300
                           mol_type = genomic DNA
                           organism = Methylobacterium sp.
SEQUENCE: 31
aaggccctc aatataagga gagattccct accggagtga cgtttcactg cgcaagttat    60
acagattgca aaaatcacat tggtagcacc tactccccaa gctacgccaa tctctccaac   120
taacggccct accagaacag cagctactcg gccaacgctt agtactgcag tagtaaggaa   180
tatcgctctg ccatttccat ttgcgagcaa tacggcacca cataagctga aaatagcgtt   240
aactgcataa aacggtatta atacttgcac taacgccgtt gctgagaccc attttttcccc   300

SEQ ID NO: 32              moltype = DNA   length = 301
FEATURE                    Location/Qualifiers
source                     1..301
                           mol_type = genomic DNA
                           organism = Methylobacterium sp.
SEQUENCE: 32
cgcgccaagc gatcctccgg cgagacatcc agcgcgcgat cctccgacac gtcgaaggga    60
tgcccgttga tcgaggatcg ggccttgtgg cggatggctg ggtaatccgc cttgatcttc   120
gctaggtcct ccgcgctcat agcgccattg cgcgccggta cactgtaatt ggccgtccgc   180
tggaacaccg tgagatgggc ggccttcgcc gcgatcaccg gagcggcttg gatcccggtg   240
gaaccagtcc cgatcaggcc aacccgccgg cccgtgaaat cgacatcctc atggggccat   300
c                                                                  301

SEQ ID NO: 33              moltype = DNA   length = 300
FEATURE                    Location/Qualifiers
source                     1..300
                           mol_type = genomic DNA
                           organism = Methylobacterium sp.
SEQUENCE: 33
gcccttctgt caggcgatat tgtataatgg cgttgcccca atagaagcag ccattcgtgc    60
```

-continued

```
gagggcagca gcgacgctag gtcgaaagag catcctaatc tcgatcaaga tgcgactgag  120
atttctgatg aaaatatcta gacacaagca aagctggtga aattacaacg atcatggcga  180
caattgcggc caattcggcc ggaacttgaa ggaacataaa aatgaatatt acaaatatac  240
cgcaaagcat gtagagttgc tacaccaagg gtcgggacgt ccaaaaaaac tcactgagga  300

SEQ ID NO: 34              moltype = DNA   length = 300
FEATURE                   Location/Qualifiers
source                    1..300
                          mol_type = genomic DNA
                          organism = Methylobacterium sp.
SEQUENCE: 34
ggaacataaa aatgaatatt acaaatatac cgcaaagcat gtagagttgc tacaccaagg  60
gtcgggacgt ccaaaaaaac tcactgagga agtcgactgg aagcacgagg cgcccccccc  120
aggagcgggg cgaccggcaa gggggcccgc aattgtcgcc atgatcgacc agcttaggta  180
ggatcctctt tcgacctaac gaatggctgc ttctattggg gcaacgccat tatacaatat  240
cgcctgacca tctggaacgc ggcccggtcc accggcaggt tggcgacgac agcgtcggag  300

SEQ ID NO: 35              moltype = DNA   length = 300
FEATURE                   Location/Qualifiers
source                    1..300
                          mol_type = genomic DNA
                          organism = Methylobacterium sp.
SEQUENCE: 35
cggcgtcgac cagccgggcg aactgcttgg gcatgctctc ccgcgacgcc ggccacagcc  60
gcgtccccgt ccctccgcac aggatcatcg ggtggatttg aaaggcaaaa cgggacatca  120
ggataggccg ctcaggcgtt ggcgctgagg cgcttgatcg cggcgtcgac catctcggtg  180
atcagcgcct cgaggctggt ctcggcctcc cagccgaagg tcgccttggc cttggcgggg  240
ttgcccagca gcacctcgac ctctgccggc cggaacagcg ccggcgtcgac gatcaggtgg  300

SEQ ID NO: 36              moltype = DNA   length = 300
FEATURE                   Location/Qualifiers
source                    1..300
                          mol_type = genomic DNA
                          organism = Methylobacterium sp.
SEQUENCE: 36
ctggacatgc gcccaccccg gccaagtccg accgcaccgg caaccgctcc tgtagtcgtc  60
gtcatcgttc tcacccctga ggcggagacc gtccgctaac ggggtgtctc aagcaaccgt  120
ggggcggagg aacacgcacg tagtcgcgtt tcaaggttcg cacgaacgcc tcggccatgc  180
cgttgctctg cgggctctcc agcggcgtcg tttttggcac caaaccaagg tcgcgggcga  240
agcggcgcgt gtcgcgggga ctgtcaggaa tttcgtgtgg gggcggccat agtggatccg  300

SEQ ID NO: 37              moltype = DNA   length = 300
FEATURE                   Location/Qualifiers
source                    1..300
                          mol_type = genomic DNA
                          organism = Methylobacterium sp.
SEQUENCE: 37
gcaaaacgac ctaatagttc tacagcggca tgcgccaagt cagcgcggtg aacagtatac  60
ctgggagcaa cttgtcctcc gaaacccaca taaaacaaat tactcctggc agtgcccagt  120
ccatcaaaat cgaatacaat atttctcgag gaggcatctg taatagcctg ccaaagcaac  180
aaagctatgg cgccgttatg actttcattg cttctggtag acataaaata atatgccgat  240
ttgtgatccc aaatgtagaa tattgccgca tcaattgcgc caagtttatt tcggatcgat  300

SEQ ID NO: 38              moltype = DNA   length = 300
FEATURE                   Location/Qualifiers
source                    1..300
                          mol_type = genomic DNA
                          organism = Methylobacterium sp.
SEQUENCE: 38
ggcgccaacg gtatgatcgc atgattttcc tgcggcatag cttgcgggaa tggcgtattt  60
ggcgctctcc tcaggaattt ctaagggcat acgcaggaac tctacagcac ttttactggt  120
attttgtagt gacagcggag gaggctggtg ctcaaggtaa tcgtgatgaa gtgatccggg  180
ccattcgggg cgcgtttcta gtctttccaa tccgcgccct gtaccacgta ttacgccgga  240
ccggtctgcg ccgcgccgcc ctcttgaccg ccctaaatgt ctaagagcgt ctaacaaagc  300

SEQ ID NO: 39              moltype = DNA   length = 300
FEATURE                   Location/Qualifiers
source                    1..300
                          mol_type = genomic DNA
                          organism = Methylobacterium sp.
SEQUENCE: 39
gacgatatcg ctcatcttca ctgcattgaa gctggtgccg tactgcatag ggatgaaaaa  60
gtgatgcgga tagacggctg acgggaaagc gcctggtcga tcgaagactt tgctgacgag  120
gttgtggtag ccccggatat aggcatcgaa ggccgggacg ttgatcccat cctttgcctt  180
atcttgactg gcgtcgtcgc gtgccgtcag aacgggcacg tcgcaggtca tcgaggccag  240
caccttgcgg aacacctgcg ttccgccgtt gggattatcg acggcgaacg cggtggccgc  300

SEQ ID NO: 40              moltype = DNA   length = 300
FEATURE                   Location/Qualifiers
```

-continued

```
source                    1..300
                          mol_type = genomic DNA
                          organism = Methylobacterium sp.
SEQUENCE: 40
agcccacaag cctgatgcac ttaactacat cctctaatgt cgcgccaatt tgcttggcgg   60
caggggatgt tgtatcgtca taggcttgtc taaccggaac ttgtttgcca atctctttgg  120
cgatcgcaac cgccatctcg tgttcgtcaa ccatgtgcgc gttcctctaa ttgcactcat  180
ggtgccacgt gcacctccga tcgtctcgtg tctagaatga aggtgggaac aaccttacac  240
aggctttcgc gacgcgcgaa tttctggttt ctccgcctcg gatgtgggtt tgagcgcttc  300

SEQ ID NO: 41            moltype = DNA   length = 300
FEATURE                  Location/Qualifiers
source                    1..300
                          mol_type = genomic DNA
                          organism = Methylobacterium sp.
SEQUENCE: 41
cttttcattt gtcatgatct cgaccaaggt attcacggca agctcggtct gttgcttagc   60
aagtgcctga acttcgcgaa cgatcggctc tcgacccttc gggttcgaga cctgtccctt  120
ttgaaaacca cgtgccctac actttctcggg atcaaggtgc gggttggctt tggtcaaaat  180
tctctggcgt cccattacac gccctccgca tcatcgttcc cgcgaacgat ctgaccccg   240
acttccgcga ggaagcgtgt ggcgtgatcc tcgaagcgga atgccacctc gaactgttcc  300

SEQ ID NO: 42            moltype = DNA   length = 300
FEATURE                  Location/Qualifiers
source                    1..300
                          mol_type = genomic DNA
                          organism = Methylobacterium sp.
SEQUENCE: 42
cagcagcaag cagatcgttg aaaaccgctt gaaccgcatc ttgatcggga ccggaaccaa   60
tcaggtcatc taggtaaacc gagacgtaaa ctcgtttgcg ctcggcatct ttcagaacgt  120
ccgtgatgcc agaccgcatt agtaccatcg tcgccaaggc gggcgactga acgaagccga  180
tcggcagaga gtaacgggga ccgcccctaa tcgggttgcg aacgcaagac cacttagcaa  240
aggttcgagc acggccgaac ttcgcatggt ggagagccgc ggcaacacgg ttccgtgata  300

SEQ ID NO: 43            moltype = DNA   length = 300
FEATURE                  Location/Qualifiers
source                    1..300
                          mol_type = genomic DNA
                          organism = Methylobacterium sp.
SEQUENCE: 43
ggaaatcggc ttcaagtacg acgtcacgcc ggccatgcag gtcacgggtg cactgttcaa   60
tctcgagcgc gacaaccagc cgttccctc gaacgtggag tccggcctcg tccttggcgc  120
aggtcagaca cgcacccagg gcgcggaaat cggcctggcc ggctatctaa ccgattggtg  180
gcaggtcttt ggcggctacg cttataccga ggcacgcgta ctctcgccac tggaagacga  240
tggagacgtg atcgcagcag gtaatctcgt cggcaacgtt ccgctaaata ctttcagtct  300

SEQ ID NO: 44            moltype = DNA   length = 300
FEATURE                  Location/Qualifiers
source                    1..300
                          mol_type = genomic DNA
                          organism = Methylobacterium sp.
SEQUENCE: 44
cggcctggcc ggctatctaa ccgattggtg gcaggtcttt ggcggctacg cttataccga   60
ggcacgcgta ctctcgccac tggaagacga tggagacgtg atcgcagcag gtaatctcgt  120
cggcaacgtt ccgctaaata ctttcagtct gttcaacaag ttcgatatca acgagaattt  180
ctccgttgct ctgggctatt actatcagga tgccagcttt gcctcctcag acaatgcagt  240
gcgtttgcca agttattcgc ggttcgatgg cgggttgttc tatcgattcg acgagttgac  300

SEQ ID NO: 45            moltype = DNA   length = 300
FEATURE                  Location/Qualifiers
source                    1..300
                          mol_type = genomic DNA
                          organism = Methylobacterium sp.
SEQUENCE: 45
acgttccgct aaatactttc agtctgttca acaagttcga tatcaacgag aatttctccg   60
ttgctctggg ctattactat caggatgcca gctttgcctc ctcagacaat gcagtgcgtt  120
tgccaagtta ttcgcggttc gatggcgggt tgttctatcg attcgacgag ttgacacgcg  180
ttcagcttag cgtcgagaac attttcgaca ggcgttacat catcaactcc aacaacaaca  240
acaacctcac gcctggcgcg ccgagaacag tccgcgtgca attgatcgct cggttctaaa  300

SEQ ID NO: 46            moltype = DNA   length = 300
FEATURE                  Location/Qualifiers
source                    1..300
                          mol_type = genomic DNA
                          organism = Methylobacterium sp.
SEQUENCE: 46
tagacattcc aacaaaccgg caagaggctc gtcctcactc gaggatttgt tgggacttgc   60
atgatgtcga agcggagccg ttatgacctg ggtgcgatca tgcgccgagc atgggagatg  120
gctcgggagg cggcattcgc ggttggcgag cgggcacgga ctcaccttgc tgccgcgatg  180
```

-continued

```
cgcagcgcgt gggccgaagc caagttggca ctcgcgccca cgaagacgga gcaggatcgt   240
ctctctccga gcgacatgat cggacatgag gacgcctacc aaggccgggt tctaaaatat   300

SEQ ID NO: 47             moltype = DNA   length = 300
FEATURE                   Location/Qualifiers
source                    1..300
                          mol_type = genomic DNA
                          organism = Methylobacterium sp.
SEQUENCE: 47
aagatggata cgacaagcgc gattacatta tttgcgaaat agatggacaa ataaaagaca   60
aaggactgat gtatttcctt aaatctggac aagttgacct ctttcacata gaagtcacca   120
ctccctttgg gacaatttgg tgtcacgaaa acatagaggc cgaacttctt agctgaatta   180
tcgcgctccg ggttcttatg cggctgagtg aagcgcggga cagcttgcga gcagggccgc   240
caatggcagc cgggatgaca caatgctcgg tctcccgacg cttcttcaat cgggagcgct   300

SEQ ID NO: 48             moltype = DNA   length = 299
FEATURE                   Location/Qualifiers
source                    1..299
                          mol_type = genomic DNA
                          organism = Methylobacterium sp.
SEQUENCE: 48
agctgaatta tcgcgctccg ggttcttatg cggctgagtg aagcgcggga cagcttgcga   60
gcagggccgc caatggcagc cgggatgaca caatgctcgg tctcccgacg cttcttcaat   120
cgggagcgct tcgcagcccg gggcggcgcg ctcatgcgtc acgacctggg ccctgcgcac   180
cttcgcggcc ccgccgtccc ggcagatccc tgatgcccca agtgggcggc cactccatca   240
aagaaccccg gcctgtggca gatctcgtag gcataccgag gttccgcagt gcccccacc    299

SEQ ID NO: 49             moltype = DNA   length = 300
FEATURE                   Location/Qualifiers
source                    1..300
                          mol_type = genomic DNA
                          organism = Methylobacterium sp.
SEQUENCE: 49
acggtcaccc cacggactgg gcgagtacct caccggtgtt ctatcataac gccgagttag   60
tttttcgaccg tcccttatgc gatgtaccac cggtgtcggc agccgatttc gtccgcaccgg  120
gagctggcgt tccggttcag accaccatca tcggtcacga tgtctggatt ggacacgggg   180
ccttcatctc ccccggcgtg actataggaa acggcgcgat cgtcggggcc caggcggtcg   240
tcacaagaga tgtcccaccc tatgcggtag ttgctggcgt ccccgcgacc gtacgacgat   300

SEQ ID NO: 50             moltype = DNA   length = 300
FEATURE                   Location/Qualifiers
source                    1..300
                          mol_type = genomic DNA
                          organism = Methylobacterium sp.
SEQUENCE: 50
ccaataaaag cgttggccgc ctgggcaacc cgatccgagc ctaagactca aagcgcaagc   60
gaacacttgg tagagacagc ccgccgacta cggcgttcca gcactctccg gctttgatcg   120
gataggcatt ggtcaaggtg ccggtggtga tgacctcgcc cgccgcaagc ggcgaattac   180
tcggatcagc ggccagcacc tcgaccaagt gtcggagcgc gaccaaaggg ccacgttcga   240
ggacgtttga ggcgcgacca gtctcgatag tctcatcgtc gcggcgaagc tgcacctcga   300

SEQ ID NO: 51             moltype = DNA   length = 300
FEATURE                   Location/Qualifiers
source                    1..300
                          mol_type = genomic DNA
                          organism = Methylobacterium sp.
SEQUENCE: 51
cgatggcacc gacctgccat gcctctgccg tccgcgccag aatggtaaag aggacgaagg   60
gggtaaggat cgtcgctgca gtgttgagca gcgaccagag aaggggccg aacatcggca    120
tcaaacctcg attgccactc ggacgcgaag gcgtcttga aggagggatg gaagcgaaac    180
ggccgcagag taaccgccga cgaaagattg caccccttat cgagcaggat cggaggtgaa   240
ggcaagcgtg ggttattggt aagtgcaaaa aatataatgg tagcgtcaga tctagcgttc   300

SEQ ID NO: 52             moltype = DNA   length = 300
FEATURE                   Location/Qualifiers
source                    1..300
                          mol_type = genomic DNA
                          organism = Methylobacterium sp.
SEQUENCE: 52
agtcattgat caagcaaccc ctattgagtt ggatatcgaa ggatcaaggt cgcgtcaata   60
gatgcatcta tcaggccaaa tgtcgctttt caagaatggc tctttcgaag ctatctttat   120
aatcgctcgc cattctctca ttaccaaaat cgaccttaac tagctcgaca ttgatgcgag   180
cagctccggc aaacgaggag agattgacct taaaggaatt gaacgcctca agcaattcag   240
acacattacc aggagtgcta tagcaacaac cagacccata tcggtcaata acctctttta   300

SEQ ID NO: 53             moltype = DNA   length = 300
FEATURE                   Location/Qualifiers
source                    1..300
                          mol_type = genomic DNA
```

-continued

```
                          organism = Methylobacterium sp.
SEQUENCE: 53
cgcaaaacga tttatcactg ccatcttgtt gtttgataac ccttttttac cagacgttat   60
gctgggcgag aaagaggact agcagatcgg agcggtatcg cgattttttcg gtagttcgcg  120
cctacaacag gataagatcc gatagtgaag caacatggct gtttttttgat ttgtaagtca  180
gcaacttaag cagccagcct atctgccgtc gcagacgctt gaggcatcgg gcagcatctt  240
agaaaaggtg gcagtaattg ccacagcgga acgtagcggc acggataagc acgcagggtc  300

SEQ ID NO: 54            moltype = DNA   length = 300
FEATURE                  Location/Qualifiers
source                   1..300
                         mol_type = genomic DNA
                         organism = Methylobacterium sp.
SEQUENCE: 54
cccatctgga cccaatatcc ccttcatcga caattcccga gtaagtgtgg gttcgaggat   60
ttcgcgaaac agccttgttc gttcctccgg ccttaaaatt ggcgtgccgt cgggagatcg  120
ataggcatcc cttacctgcc tttcgaccgc cggcacacgc gcgccggtcg tcgtgttcac  180
ggccacggaa tggacgaagg tgcgccgctc atttcgctcg tttgccgtct ccaccatcca  240
ggaggccagc aggacggttt cgtctcgacc gccggtcaca cacaccgcaa gggactcagg  300

SEQ ID NO: 55            moltype = DNA   length = 300
FEATURE                  Location/Qualifiers
source                   1..300
                         mol_type = genomic DNA
                         organism = Methylobacterium sp.
SEQUENCE: 55
acctgctaaa atcacgtcct ctcagattga aaaatcattg aagaaacgtg tcgaacgatt   60
gccggggatt atgacgttag atcaattgaa aaatacaagc tttgaaattg agttacagcc  120
aaaagatgcc ccggatccgg acccatcaga cttcggtggc tagttcgagc caaactcgaa  180
cgtcgccatg gcgcgcaagt cgcaatacca tttcacagcg cagcggttat ttcgttgtac  240
actgtagcaa tgcgtcggct tgcgcgcttc cgctggcgat caaaggtccg ccgatttacg  300

SEQ ID NO: 56            moltype = DNA   length = 300
FEATURE                  Location/Qualifiers
source                   1..300
                         mol_type = genomic DNA
                         organism = Methylobacterium sp.
SEQUENCE: 56
tcccgaacat acaatggagg aagcgtgtgg taggccaatt tgtaacgaaa tatggcatcg   60
gtcacggctc tctcaataaa ttcgatctca agtcttctga acgagcatgc ctcatcctta  120
tcctgagcga acgcctgcca gtttgcagtc attccaacat acatagccaa aaaggcgagg  180
tagaccttca tacgggcacc tcaatcgtcc ccattcgttc aagctccttc aagataacag  240
ccgcaccaca ttgctgagat cgaagattcg gatcaaatat tccatcaaat ttatactttc  300

SEQ ID NO: 57            moltype = DNA   length = 300
FEATURE                  Location/Qualifiers
source                   1..300
                         mol_type = genomic DNA
                         organism = Methylobacterium sp.
SEQUENCE: 57
gcatcctttg cgctcgcagg cctaaggtca agcccggtta cttcgtttgg tagaacgagg   60
tagacgatgc ctagtcttaa ggtggcccat gttaaccaac agggccagaa catgattata  120
gttccgttag atgccaactt cggttacaaa accgatggtg agcagtccga catcatgttc  180
gaaatacagg acgcggcgcg gtccgccggt cttgcgggtg ccgtagtagc gttctggcag  240
tcaggtggac aaacccgttt ccggggcccg gctccgtggc acccattcct tcgcagcctc  300

SEQ ID NO: 58            moltype = DNA   length = 300
FEATURE                  Location/Qualifiers
source                   1..300
                         mol_type = genomic DNA
                         organism = Methylobacterium sp.
SEQUENCE: 58
caactatgta gacccgacgg tgcgatttca cttcgcaaag ccgcagggca gcacccttgc   60
gctcaatgtt gacgccagcg tgatctatac tattaccgtc acgcacacgc agggcggcgt  120
acagattcat cgcgagagta agaaccacca tcagaccatc acgcgcagcg acctgagcaa  180
gcagttcggc gttggtgtgg ccgaccagct gacgcgcgat caggtcatga aggtgatcga  240
gtcggcattt cgcgacgcta cccgctaaga tcggcgccca cgaaacgcta cgagactagg  300

SEQ ID NO: 59            moltype = DNA   length = 300
FEATURE                  Location/Qualifiers
source                   1..300
                         mol_type = genomic DNA
                         organism = Methylobacterium sp.
SEQUENCE: 59
agccggcatc ttgttcaagg cgctcacctc gacgccgacg ctgtaggcga cttgagaggg   60
cgtctcatat gaacgaagca tcttcgcgta gagaaccttc ttgttctcct gcgtgatgtt  120
cgctttgcag acgttgactg ccgccatgaa cgccgaagcc ttgcgcgctt catcgtaatc  180
gcctgcgaag gcgggtagtg aaaagcttag tgcaatggca aacacagccg ccgaacgtcg  240
catggtatcc gtccccgatt gacggcagtg ccgccatatc tcggctttag cagagctgat  300
```

-continued

```
SEQ ID NO: 60            moltype = DNA   length = 300
FEATURE                  Location/Qualifiers
source                   1..300
                         mol_type = genomic DNA
                         organism = Methylobacterium sp.
SEQUENCE: 60
aacctgcgcc ggccgaggtt tcgcgagccg tcgccacggg caacgcctcg cccgcgatgt   60
gcaaaaaagt ccccggcact tcgcgccgtc gtccgatcca cgaccgcgaa tttctcaacg   120
agtacaaggt gcttatggga gatccgagcg tccgtcccgg agcccgagac cgcgcggccc   180
gagtaatagg cgaaaaagac tcctactcct cgggcttctc gggccccctc agcaacatct   240
acgcttgccg cccatcaccc tggcgggaga tcagcgacga gacacaggcc cacttcgccc   300

SEQ ID NO: 61            moltype = DNA   length = 300
FEATURE                  Location/Qualifiers
source                   1..300
                         mol_type = genomic DNA
                         organism = Methylobacterium sp.
SEQUENCE: 61
ctcaacgttg ccgccttaac cgaagactaa ctaacataaa tttcagttag ccgcgaaaca   60
gaatatgata cttggtctta tacgacgcat agaggcgcat tccgtcaagt cgcgcattgc   120
agagtccccc cgaaaattcg ttttctggga gcgagcaaga acgtgtgcac gtgttctgtc   180
actctatttt ctggtttaga gcaatcatct cgcggctcag atcccgtcgt tccatagagt   240
ggtttccggt tcagtatgaa ttgtgagcag cccctgcggc tatatctact tcgacgtata   300

SEQ ID NO: 62            moltype = DNA   length = 300
FEATURE                  Location/Qualifiers
source                   1..300
                         mol_type = genomic DNA
                         organism = Methylobacterium sp.
SEQUENCE: 62
accaacaggc agaagaggct tacaaaaatg ctctagatat ctataatcgc gccggtctgg   60
ataataggcg ggaaaagtca aatattctta tcggacttgg cgatgcagct agcgcactga   120
gcaaatttat agacgcgaaa aatttctaca gtgaaggttt agcagtccga gcgcggtcat   180
gacggtgctt gcggactagt gtctgctcgc aattcagagc agccgcttcg gctggttcag   240
tttgggtatg ccctttctgt accagcctgt gactggtctg gtatgtagcc cttgaccaat   300

SEQ ID NO: 63            moltype = DNA   length = 300
FEATURE                  Location/Qualifiers
source                   1..300
                         mol_type = genomic DNA
                         organism = Methylobacterium sp.
SEQUENCE: 63
atgaagctcc gtcgtgttta tgtaaagaac gttcgcagtt tctacgatgc tgaagaactc   60
attctggacg gagatatttc tattattata ggcccaaatg gtggaggaaa aacaaatcta   120
cttgatgcga cgatacactt gttgagaaga catttattgc aatcgtgggc tgtcgttcgc   180
catacataca cgccaataaa ctattccgat cacttccaac caaatgatca aatcacaaac   240
tatgcgctgg agaagtacag cggtcgcgaa agcgaagacc aagtcgttga gttcgatatc   300

SEQ ID NO: 64            moltype = DNA   length = 300
FEATURE                  Location/Qualifiers
source                   1..300
                         mol_type = genomic DNA
                         organism = Methylobacterium sp.
SEQUENCE: 64
cgggggcggt ctcctcatat atggagggaa ttaatctgaa gggtcggagc ccccgctacg   60
gcacacacac ggcggcgggc ggtgggctcc ttcctcatat acgcttcctg ataatttcga   120
ccgtaatcgc ccgccggccg agcggccaga ccttattagt ccagcatcac acggtgcatc   180
gtatcgtgga gggcgaacaa ccgcctaagg ttcgccacgt agccatccac atccgccctt   240
gccgctcgcg caagggaagc agaatgcttg atagcgactt cgcgggcgtc tttggtagcc   300

SEQ ID NO: 65            moltype = DNA   length = 300
FEATURE                  Location/Qualifiers
source                   1..300
                         mol_type = genomic DNA
                         organism = Methylobacterium sp.
SEQUENCE: 65
tgtgggcgct catggaaacg ggggacgtgc tttttttgatc tctagccatt gtcatcatcc   60
atcggtccgg gtgacaggcc tttacgcaca taacaacggt tatttcgatc agccccctcc   120
tgatcgcaca agtcagctat acagatgctt ctgaaagcca acaaaggcgt tacgtatctg   180
cgtgacccca ccgagctgcg ctgcggcatc gctgacagct ctgtatttta attcgaggag   240
gtggggcaat ttagcctggt caagctcgcc aacgtcttcc ttcacatatt gagacaggac   300

SEQ ID NO: 66            moltype = DNA   length = 300
FEATURE                  Location/Qualifiers
source                   1..300
                         mol_type = genomic DNA
                         organism = Methylobacterium sp.
SEQUENCE: 66
```

```
agagtgtatt tccccaagac tttatctctt tgctcatcac aaaacagccc gctcaagatg   60
atatgcgctg ggatttgtgc cgcgacccgt tgtaattgta tttacctctc ggctcatgtt  120
ccctgtcgcc ggagcgattg gaggtaaagt aatctcaact ttgcggccca tggctgatgc  180
tagctcagct acgcgaccta aggtaatatc tttgtgtccg cggagttcgc gatgaatgac  240
cgagcgattg acgccgatgg tgcgggcaat atcggcttga gttagaccgt tcttggcttc  300

SEQ ID NO: 67            moltype = DNA   length = 300
FEATURE                  Location/Qualifiers
source                   1..300
                         mol_type = genomic DNA
                         organism = Methylobacterium sp.
SEQUENCE: 67
acctgtctcg acatcggggg cagccacgag gcgtcggccg tggtagatct cggcgaagcg   60
gtagtagtgg gcgaggtccc catcgggatc gatggggagg tccggcgtac cttctccctc  120
ttctgcgatt agcgacaggg ctcgcatggc gctgggtgcg tcagtgatgg cgaacaacct  180
actatcgggg aaccaccgcc tgtcgacgag ctggcggtcc gggtttcctt tgaagacagc  240
gtcacccagc gcttcgatct tctcaatcaa ggctgcgtag aactgcccga tggtcgcgaa  300

SEQ ID NO: 68            moltype = DNA   length = 300
FEATURE                  Location/Qualifiers
source                   1..300
                         mol_type = genomic DNA
                         organism = Methylobacterium sp.
SEQUENCE: 68
gacgtggtga cggtggcacc agtcgcccag cgaagcggct actgtactga gcccgcagtc   60
atgtcggctg aagaaatggt cgatatgccc cagggaggc gggctaggt cgtacctcaa  120
attcaccggc aggatcttgt ccagcaaggc gtccgaattc gcatcgacct gacttaggaa  180
attaccgagg taatcgctcg gtccgttcgc gtcggcggcc tgcatcgcca gcagcgcctt  240
atgctcggtc gtcaactcac gagcgaatat tgtccaggac aggttgtcga cctcggcgac  300

SEQ ID NO: 69            moltype = DNA   length = 300
FEATURE                  Location/Qualifiers
source                   1..300
                         mol_type = genomic DNA
                         organism = Methylobacterium sp.
SEQUENCE: 69
gagcatggca ggccaccacg catcgcttct tcatcacctt gctcggacga cttgctgctt   60
tgtcggtctc tctctcaagg acgagacgct gcgacacttg cttcgtcaga gtgccaggat  120
taatcccggt caataccact actacgtcag ctggcgtgcg ccgggcggca cgagggacgt  180
cgacgcggaa cgattgattc gagacgctaa ctttgacgtg tacaatttag tcacgctttt  240
ccttagcgac gccgagatag cctcgttggg ccgcttgctc accgccgatg cagccgagtt  300

SEQ ID NO: 70            moltype = DNA   length = 300
FEATURE                  Location/Qualifiers
source                   1..300
                         mol_type = genomic DNA
                         organism = Methylobacterium sp.
SEQUENCE: 70
aacgcgatgg gagcagcacg taatgggcgt catacaagat ataaagaag gacttgaagg   60
tagaatagat aaccttaagg aaaatattga taatatcagt tccagtatca catgcacaat  120
acaaggagtg ccgaaggtcg agtcagaaag aattttggga tgtgcaaacg cttcgtttga  180
ccaaatacag aaaatgtgga tgaatggtcc tacggatagg gctgcatttc tcgacgccgt  240
gaaaagtttg atagaccgca acgcaagtaa tggaaaattc ggagttccag gatcatattg  300

SEQ ID NO: 71            moltype = DNA   length = 300
FEATURE                  Location/Qualifiers
source                   1..300
                         mol_type = genomic DNA
                         organism = Methylobacterium sp.
SEQUENCE: 71
ttttcctttc gcgcctatga cctgagtgcg gccgaagctg tccgcttatt agagttttac   60
aaccagatgc gagcggctta gctcttcctc cgttattaag cagggcgcct cttcttaggg  120
gcgccccttc atatttaatc ttgtctgatg tctggcgcca tatcagacaa acatcagcgt  180
tgaccttgat tttgcatcta cattagggtt gctcccagaa tggagccgcc gatgtccgtc  240
ccgtacctca agcgagagat gtggggtgtg tattacatcc attggcgcga gggcggccgc  300

SEQ ID NO: 72            moltype = DNA   length = 300
FEATURE                  Location/Qualifiers
source                   1..300
                         mol_type = genomic DNA
                         organism = Methylobacterium sp.
SEQUENCE: 72
gttggagatg gtgccgtttg caaccgtcag atcgcctact gtgaatccgg tgacctcccg   60
agagaacgtg aagtaactg tcgtagtctc gccaactgcc aaagaggtgt ccgcaacggc  120
gatggtcgct gtcggggcgc ttgtttggac atcaacggtg agaccgccg aggcaggccc  180
cgtgttacca gcggtatcga cggccctagc ggtgaccgtg tgcgatccag ccgttagcgt  240
cgaactggtg atgctatagg tcccgccgat cgccactgcc gagcccagaa tggtcgtgcc  300

SEQ ID NO: 73            moltype = DNA   length = 300
```

-continued

```
FEATURE             Location/Qualifiers
source              1..300
                    mol_type = genomic DNA
                    organism = Methylobacterium sp.
SEQUENCE: 73
accgaaggcg tccccggaca cgaaggcctg aaacaccata tctgtggcga tcaggccgac  60
gtggtcgcgg acttcaactg gcagagaatg ccaggccgct tcgatttcag atgatactgg 120
tacggacata ggagcggctt agctttctca gtgcaaatgt gattgattcc ggctcaaaaa 180
tgatcttgat cggacgagac gttttcaatc catgtcgtgt tgccatcgcc gatcggtgcg 240
tcaagagaca gatggcgccg accgtagata cgcgttcggg ttgcccgcac cgcttctcca 300

SEQ ID NO: 74        moltype = DNA   length = 300
FEATURE             Location/Qualifiers
source              1..300
                    mol_type = genomic DNA
                    organism = Methylobacterium sp.
SEQUENCE: 74
ggaggtgtga tctgatgatg tgctggatga aattggcggt cgagcacttg ttcagcttgg  60
ccagctcgac gagatcggcg tgatgctcgg cgtcgatcag gatgttcagc gagaccggac 120
gtacgcagga cttggtatta gcgccgttgc gcatcagctt gcagccttgc tctgcttctc 180
agcgtgccgc gtcaggatga ccctgatgta gctgttgagg ttgatgccgt aatagcctgc 240
ggactctgtg agatcccggc gaagatcgtc ggcgagggtc aggcggatgg tgctggtcgg 300

SEQ ID NO: 75        moltype = DNA   length = 300
FEATURE             Location/Qualifiers
source              1..300
                    mol_type = genomic DNA
                    organism = Methylobacterium sp.
SEQUENCE: 75
aagtaaccgc tcaacatgat cttcagcatg ttgtccaaca gcaggagaat acatgtaatt  60
caccatgacc ggcaagctgc gactggccat tgcttccacc gcttgaatgt agcgatcgaa 120
tttcgcaaaa tcagggtgga atgaaaatat cgaaccaaac tgcgagcctt gaatccgttc 180
tgcaaaatta tcgaaaaatt ttcttggccg actgccgttc gaaaacattc ttacgtttac 240
atgcggcccg cctgaaacaa gacagtctac cagctctggg aaatgggggt gaagggtcgg 300
```